(12) United States Patent
Powers et al.

(10) Patent No.: US 10,625,065 B2
(45) Date of Patent: *Apr. 21, 2020

(54) ASSEMBLIES FOR IDENTIFYING A POWER INJECTABLE ACCESS PORT

(71) Applicant: Bard Peripheral Vascular, Inc., Tempe, AZ (US)

(72) Inventors: Kelly B. Powers, North Salt Lake, UT (US); Jim C. Beasley, Houston, TX (US); Guy T. Rome, Herriman, UT (US)

(73) Assignee: Bard Peripheral Vascular, Inc., Tempe, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/105,725

(22) Filed: Aug. 20, 2018

(65) Prior Publication Data

US 2019/0111243 A1 Apr. 18, 2019

Related U.S. Application Data

(63) Continuation of application No. 14/171,364, filed on Feb. 3, 2014, now Pat. No. 10,052,470, which is a
(Continued)

(51) Int. Cl.
*A61M 39/02* (2006.01)
*A61M 39/04* (2006.01)
(Continued)

(52) U.S. Cl.
CPC .......... *A61M 39/0208* (2013.01); *A61B 6/12* (2013.01); *A61B 6/481* (2013.01); *A61M 5/007* (2013.01);
(Continued)

(58) Field of Classification Search
CPC .. A61B 6/12; A61B 6/481; A61M 2005/1581; A61M 2005/325;
(Continued)

(56) References Cited

U.S. PATENT DOCUMENTS 445,896 A 2/1891 Kinsman
546,440 A 9/1895 Tufts
(Continued)

FOREIGN PATENT DOCUMENTS

AU 2008299945 A1 3/2009
CA 2663853 A1 4/2008
(Continued)

OTHER PUBLICATIONS

U.S. Appl. No. 12/917,323, filed Nov. 1, 2010 Non-Final Office Action dated Aug. 15, 2012.
(Continued)

*Primary Examiner* — Imani N Hayman
(74) *Attorney, Agent, or Firm* — Rutan & Tucker LLP

(57) ABSTRACT

A method of using a power-injectable port includes obtaining the power-injectable access port, attaching a catheter to an outlet stem of the power-injectable access port, and implanting the power-injectable access port and the catheter into a patient. The method further includes identifying the power-injectable access port following the implanting, inserting a distal end of a needle through the septum and into the reservoir, and injecting contrast media through the needle at a rate of at least one milliliter per second. The power-injectable access port includes a housing, a septum, a reservoir, and an outlet stem in fluid communication with the reservoir. The power-injectable access port is rated for injection of contrast media at a flow rate of at least 1
(Continued)

milliliter per second. The power-injectable access port is structured for operation at a pressure in the reservoir of at least 35 psi.

40 Claims, 32 Drawing Sheets

Related U.S. Application Data continuation of application No. 13/886,201, filed on May 2, 2013, now Pat. No. 8,641,688, which is a continuation of application No. 12/420,007, filed on Apr. 7, 2009, now Pat. No. 8,475,417, which is a continuation of application No. 11/380,124, filed on Apr. 25, 2006, now Pat. No. 8,545,460.

(60) Provisional application No. 60/737,466, filed on Nov. 15, 2005, provisional application No. 60/675,309, filed on Apr. 27, 2005.

(51) Int. Cl.
*A61B 6/00* (2006.01)
*A61M 5/00* (2006.01)
*A61B 6/12* (2006.01)
*A61M 5/158* (2006.01)
*A61M 5/162* (2006.01)
*A61M 5/32* (2006.01)
*A61M 39/00* (2006.01)

(52) U.S. Cl.
CPC ........ *A61M 39/0247* (2013.01); *A61M 39/04* (2013.01); *A61M 5/158* (2013.01); *A61M 5/162* (2013.01); *A61M 5/3273* (2013.01); *A61M 2005/1581* (2013.01); *A61M 2005/325* (2013.01); *A61M 2039/0009* (2013.01); *A61M 2039/0045* (2013.01); *A61M 2039/0054* (2013.01); *A61M 2039/0063* (2013.01); *A61M 2039/0072* (2013.01); *A61M 2039/0205* (2013.01); *A61M 2039/027* (2013.01); *A61M 2039/0238* (2013.01); *A61M 2039/0258* (2013.01); *A61M 2039/0282* (2013.01); *A61M 2039/0288* (2013.01); *A61M 2205/32* (2013.01); *A61M 2205/6009* (2013.01); *A61M 2205/6054* (2013.01); *A61M 2205/6081* (2013.01); *Y10T 428/139* (2015.01)

(58) Field of Classification Search
CPC .. A61M 2039/0009; A61M 2039/0045; A61M 2039/0054; A61M 2039/0063; A61M 2039/0072; A61M 2039/0205; A61M 2039/0238; A61M 2039/0258; A61M 2039/027; A61M 2039/0282; A61M 2039/0288; A61M 2205/32; A61M 2205/6009; A61M 2205/6054; A61M 2205/6081; A61M 39/0208; A61M 39/0247; A61M 39/04; A61M 5/007; A61M 5/158; A61M 5/162; A61M 5/3273; Y10T 428/139
See application file for complete search history.

(56) References Cited

U.S. PATENT DOCUMENTS

| | | | |
|---|---|---|---|
| 574,387 | A | 1/1897 | Buckler |
| 611,357 | A | 9/1898 | Dembinski |
| 966,696 | A | 8/1910 | Merrill |
| D44,302 | S | 7/1913 | Director |
| 1,713,267 | A | 5/1929 | Crowley |
| D130,852 | S | 12/1941 | Rothschild |
| 2,433,480 | A | 12/1947 | Rendich |
| 2,891,689 | A | 6/1959 | Gould |
| 3,159,175 | A | 12/1964 | Macmillan |
| 3,211,431 | A | 10/1965 | Meysembourg et al. |
| 3,293,663 | A | 12/1966 | Cronin |
| 3,341,417 | A | 9/1967 | Sinaiko |
| 3,477,438 | A | 11/1969 | Allen et al. |
| 3,518,428 | A | 6/1970 | Ring |
| 3,525,357 | A | 8/1970 | Koreski |
| 3,529,633 | A | 9/1970 | Vaillancourt |
| 3,540,670 | A | 11/1970 | Rissberger |
| 3,643,358 | A | 2/1972 | Morderosian |
| 3,669,323 | A | 6/1972 | Harker et al. |
| 3,674,183 | A | 7/1972 | Venable et al. |
| 3,811,466 | A | 5/1974 | Ohringer |
| 3,829,904 | A | 8/1974 | Ling et al. |
| 3,831,549 | A | 8/1974 | Parsons |
| 3,831,583 | A | 8/1974 | Edmunds, Jr. et al. |
| 3,840,009 | A | 10/1974 | Michaels et al. |
| 3,853,127 | A | 12/1974 | Spademan |
| 3,891,997 | A | 7/1975 | Herbert |
| 3,915,162 | A | 10/1975 | Miller |
| 3,919,724 | A | 11/1975 | Sanders et al. |
| 3,922,726 | A | 12/1975 | Trentani et al. |
| 3,951,147 | A | 4/1976 | Tucker et al. |
| 3,955,594 | A | 5/1976 | Snow |
| 3,971,376 | A | 7/1976 | Wichterle |
| 4,027,391 | A | 6/1977 | Samis |
| 4,035,653 | A | 7/1977 | Karasko |
| 4,121,108 | A | 10/1978 | Manor |
| 4,123,806 | A | 11/1978 | Amstutz et al. |
| 4,143,853 | A | 3/1979 | Abramson |
| 4,168,586 | A | 9/1979 | Samis |
| 4,181,132 | A | 1/1980 | Parks |
| 4,190,040 | A | 2/1980 | Schulte |
| 4,190,057 | A | 2/1980 | Hill et al. |
| 4,194,122 | A | 3/1980 | Mitchell et al. |
| 4,196,731 | A | 4/1980 | Laurin et al. |
| 4,202,349 | A | 5/1980 | Jones |
| 4,222,374 | A | 9/1980 | Sampson et al. |
| 4,233,964 | A | 11/1980 | Jefferts et al. |
| 4,274,006 | A | 6/1981 | Caine |
| 4,286,597 | A | 9/1981 | Gajewski et al. |
| D263,335 | S | 3/1982 | Bujan |
| 4,349,498 | A | 9/1982 | Ellis et al. |
| 4,361,153 | A | 11/1982 | Slocum et al. |
| 4,405,305 | A | 9/1983 | Stephen et al. |
| 4,406,567 | A | 9/1983 | Samis |
| 4,425,119 | A | 1/1984 | Berglund |
| 4,445,896 | A | 5/1984 | Gianturco |
| 4,447,237 | A | 5/1984 | Frisch et al. |
| 4,450,592 | A | 5/1984 | Niederer et al. |
| 4,450,985 | A | 5/1984 | Beard |
| 4,456,011 | A | 6/1984 | Warnecke |
| 4,469,483 | A | 9/1984 | Becker et al. |
| 4,479,798 | A | 10/1984 | Parks |
| 4,494,545 | A | 1/1985 | Slocum et al. |
| 4,506,676 | A | 3/1985 | Duska |
| 4,529,635 | A | 7/1985 | Sheldon |
| 4,543,088 | A | 9/1985 | Bootman et al. |
| 4,549,879 | A | 10/1985 | Groshong et al. |
| 4,559,043 | A | 12/1985 | Whitehouse et al. |
| 4,559,046 | A | 12/1985 | Groshong et al. |
| 4,560,375 | A | 12/1985 | Schulte et al. |
| 4,569,675 | A | 2/1986 | Prosl et al. |
| 4,571,749 | A | 2/1986 | Fischell |
| 4,576,595 | A | 3/1986 | Aas et al. |
| 4,610,665 | A | 9/1986 | Matsumoto et al. |
| 4,612,877 | A | 9/1986 | Hayes et al. |
| 4,626,244 | A | 12/1986 | Reinicke |
| 4,627,844 | A | 12/1986 | Schmitt |
| 4,634,427 | A | 1/1987 | Hannula et al. |
| 4,636,194 | A | 1/1987 | Schulte et al. |
| 4,636,213 | A | 1/1987 | Pakiam |
| 4,645,495 | A | 2/1987 | Vaillancourt |
| 4,653,508 | A | 3/1987 | Cosman |
| 4,655,765 | A | 4/1987 | Swift |
| 4,657,024 | A | 4/1987 | Coneys |

(56) References Cited

U.S. PATENT DOCUMENTS

| | | |
|---|---|---|
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,681,560 A | 7/1987 | Schulte et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stober et al. |
| 4,707,389 A | 11/1987 | Ward |
| 4,710,167 A | 12/1987 | Lazorthes |
| 4,710,174 A | 12/1987 | Moden et al. |
| 4,718,894 A | 1/1988 | Lazorthes |
| 4,723,947 A | 2/1988 | Konopka |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,784,646 A | 11/1988 | Feingold |
| 4,793,635 A | 12/1988 | Lovison |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,886,502 A | 12/1989 | Poirier et al. |
| 4,892,518 A | 1/1990 | Cupp et al. |
| 4,895,561 A | 1/1990 | Mahurkar |
| 4,897,081 A | 1/1990 | Poirier et al. |
| 4,904,241 A | 2/1990 | Bark |
| 4,905,709 A | 3/1990 | Bieganski et al. |
| 4,908,029 A | 3/1990 | Bark et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,961,267 A | 10/1990 | Herzog |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,006,115 A | 4/1991 | McDonald |
| 5,009,391 A | 4/1991 | Steigerwald |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,053,013 A | 10/1991 | Ensminger et al. |
| 5,059,186 A | 10/1991 | Yamamoto et al. |
| 5,069,206 A | 12/1991 | Crosbie |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,375 A | 4/1992 | Harrison et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,169,393 A | 12/1992 | Moorehead et al. |
| 5,171,228 A | 12/1992 | McDonald |
| 5,176,653 A | 1/1993 | Metals |
| 5,176,662 A | 1/1993 | Bartholomew et al. |
| 5,178,612 A | 1/1993 | Fenton, Jr. |
| 5,180,365 A | 1/1993 | Ensminger et al. |
| 5,185,003 A | 2/1993 | Brethauer |
| 5,189,690 A | 2/1993 | Samuel |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,201,722 A | 4/1993 | Moorehead et al. |
| 5,203,771 A | 4/1993 | Melker et al. |
| 5,203,777 A | 4/1993 | Lee |
| 5,205,834 A | 4/1993 | Moorehead et al. |
| 5,207,644 A | 5/1993 | Strecker |
| 5,213,574 A | 5/1993 | Tucker |
| 5,215,537 A | 6/1993 | Lynn et al. |
| 5,222,499 A | 6/1993 | Allen et al. |
| 5,222,982 A | 6/1993 | Ommaya |
| D337,637 S | 7/1993 | Tucker |
| 5,224,938 A | 7/1993 | Fenton, Jr. |
| 5,242,415 A | 9/1993 | Kantrowitz et al. |
| 5,246,462 A | 9/1993 | Bekki et al. |
| 5,249,598 A | 10/1993 | Schmidt |
| 5,263,930 A | 11/1993 | Ensminger |
| D342,134 S | 12/1993 | Mongeon |
| 5,281,199 A | 1/1994 | Ensminger et al. |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,300,048 A | 4/1994 | Drewes, Jr. et al. |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,328,480 A | 7/1994 | Melker et al. |
| 5,332,398 A | 7/1994 | Miller et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,356,381 A | 10/1994 | Ensminger et al. |
| 5,360,407 A | 11/1994 | Leonard et al. |
| 5,383,223 A | 1/1995 | Inokuchi |
| 5,383,233 A | 1/1995 | Russell |
| 5,383,585 A | 1/1995 | Weiss |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,396,925 A | 3/1995 | Poli |
| 5,397,329 A | 3/1995 | Allen |
| 5,399,168 A | 3/1995 | Wadsworth, Jr. et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |

(56) References Cited

U.S. PATENT DOCUMENTS

| | | |
|---|---|---|
| 5,453,097 A | 9/1995 | Paradis |
| 5,456,698 A | 10/1995 | Byland et al. |
| 5,476,451 A | 12/1995 | Ensminger et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,545,143 A | 8/1996 | Fischell |
| 5,554,117 A | 9/1996 | Ensminger et al. |
| 5,556,381 A | 9/1996 | Ensminger et al. |
| 5,558,641 A | 9/1996 | Glantz et al. |
| 5,558,829 A | 9/1996 | Petrick |
| 5,562,617 A | 10/1996 | Finch, Jr. et al. |
| 5,562,618 A | 10/1996 | Cai et al. |
| 5,575,770 A | 11/1996 | Melsky et al. |
| 5,593,028 A | 1/1997 | Haber et al. |
| 5,593,434 A | 1/1997 | Williams |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai |
| 5,637,102 A | 6/1997 | Tolkoff et al. |
| 5,638,832 A | 6/1997 | Singer et al. |
| 5,647,855 A | 7/1997 | Trooskin |
| RE35,601 E | 9/1997 | Eckenhoff |
| 5,662,600 A | 9/1997 | Watson et al. |
| 5,662,612 A | 9/1997 | Niehoff |
| 5,662,616 A | 9/1997 | Bousquet |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,707,357 A | 1/1998 | Mikhail et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,755,780 A | 5/1998 | Finch, Jr. et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,792,123 A | 8/1998 | Ensminger |
| 5,797,886 A | 8/1998 | Roth et al. |
| 5,810,789 A | 9/1998 | Powers et al. |
| 5,814,016 A | 9/1998 | Valley et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,848,989 A | 12/1998 | Villani |
| 5,851,221 A | 12/1998 | Rieder et al. |
| 5,853,394 A | 12/1998 | Tolkoff et al. |
| 5,868,702 A | 2/1999 | Stevens et al. |
| 5,879,322 A | 3/1999 | Lattin et al. |
| 5,882,341 A | 3/1999 | Bousquet |
| 5,882,353 A | 3/1999 | VanBeek et al. |
| 5,895,424 A | 4/1999 | Steele, Sr. et al. |
| 5,897,528 A | 4/1999 | Schultz |
| 5,899,856 A | 5/1999 | Schoendorter et al. |
| 5,904,934 A | 5/1999 | Maruyama et al. |
| 5,906,592 A | 5/1999 | Kriesel et al. |
| 5,906,596 A | 5/1999 | Tallarida |
| 5,908,413 A | 6/1999 | Lange et al. |
| 5,908,414 A | 6/1999 | Otto et al. |
| 5,911,706 A | 6/1999 | Estabrook et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,927,345 A | 7/1999 | Samson |
| 5,928,197 A | 7/1999 | Niehoff |
| 5,928,744 A | 7/1999 | Heilmann et al. |
| 5,931,829 A | 8/1999 | Burbank et al. |
| 5,941,856 A | 8/1999 | Kovacs et al. |
| 5,944,023 A | 8/1999 | Johnson et al. |
| 5,944,688 A | 8/1999 | Lois |
| 5,944,698 A | 8/1999 | Fischer et al. |
| 5,944,712 A | 8/1999 | Frassica et al. |
| D413,672 S | 9/1999 | Fogarty |
| 5,947,953 A | 9/1999 | Ash et al. |
| 5,951,512 A | 9/1999 | Dalton |
| 5,951,522 A | 9/1999 | Rosato et al. |
| 5,951,929 A | 9/1999 | Wilson |
| 5,954,687 A | 9/1999 | Baudino |
| 5,954,691 A | 9/1999 | Prosl |
| 5,957,890 A | 9/1999 | Mann et al. |
| 5,961,497 A | 10/1999 | Larkin |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,989,641 A | 11/1999 | Oulie |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,056,717 A | 5/2000 | Finch et al. |
| 6,077,756 A | 6/2000 | Lin et al. |
| 6,086,555 A | 7/2000 | Eliasen et al. |
| 6,090,066 A | 7/2000 | Schnell |
| 6,099,508 A | 8/2000 | Bousquet |
| 6,102,884 A | 8/2000 | Squitieri |
| 6,113,572 A | 9/2000 | Galley et al. |
| 6,120,492 A | 9/2000 | Finch et al. |
| 6,132,415 A | 10/2000 | Finch et al. |
| 6,152,909 A | 11/2000 | Bagaoisan et al. |
| 6,161,033 A | 12/2000 | Kuhn |
| 6,171,198 B1 | 1/2001 | Lizama Troncoso et al. |
| 6,171,298 B1 | 1/2001 | Matsuura et al. |
| 6,186,982 B1 | 2/2001 | Gross et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,200,338 B1 | 3/2001 | Solomon et al. |
| 6,203,570 B1 | 3/2001 | Baeke |
| 6,210,366 B1 | 4/2001 | Sanfilippo, II |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,261,259 B1 | 7/2001 | Bell |

(56) References Cited

U.S. PATENT DOCUMENTS

| | | |
|---|---|---|
| 6,269,148 B1 | 7/2001 | Jessop et al. |
| 6,272,370 B1 | 8/2001 | Gillies et al. |
| 6,287,293 B1 | 9/2001 | Jones et al. |
| 6,290,677 B1 | 9/2001 | Arai et al. |
| 6,305,413 B1 | 10/2001 | Fischer et al. |
| 6,306,124 B1 | 10/2001 | Jones et al. |
| D450,115 S | 11/2001 | Bertheas |
| 6,315,762 B1 | 11/2001 | Recinella et al. |
| 6,332,874 B1 | 12/2001 | Eliasen et al. |
| 6,351,513 B1 | 2/2002 | Bani-Hashemi et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,459,772 B1 | 10/2002 | Wiedenhoefer et al. |
| 6,471,674 B1 | 10/2002 | Emig et al. |
| 6,473,638 B2 | 10/2002 | Ferek-Petric |
| 6,475,516 B2 | 11/2002 | DiCosmo et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,562,023 B1 | 5/2003 | Marrs et al. |
| 6,572,583 B1 | 6/2003 | Olsen et al. |
| 6,582,418 B1 | 6/2003 | Verbeek et al. |
| 6,592,571 B1 | 7/2003 | Verbeek et al. |
| 6,610,031 B1 | 8/2003 | Chin |
| 6,613,002 B1 | 9/2003 | Clark et al. |
| 6,613,662 B2 | 9/2003 | Wark et al. |
| 6,626,936 B2 | 9/2003 | Stinson |
| D480,942 S | 10/2003 | Ishida et al. |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,663,646 B1 | 12/2003 | Shah |
| 6,676,633 B2 | 1/2004 | Smith et al. |
| 6,697,664 B2 | 2/2004 | Kienzle, III et al. |
| 6,699,219 B2 | 3/2004 | Emig et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,726,063 B2 | 4/2004 | Stull et al. |
| 6,726,678 B1 | 4/2004 | Nelson et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,808,738 B2 | 10/2004 | DiTizio et al. |
| D498,894 S | 11/2004 | Gould |
| 6,826,257 B2 | 11/2004 | Sayre et al. |
| 6,827,709 B2 | 12/2004 | Fujii |
| 6,852,106 B2 | 2/2005 | Watson et al. |
| 6,856,055 B2 | 2/2005 | Michaels et al. |
| 6,878,136 B2 | 4/2005 | Fleury et al. |
| 6,878,137 B2 | 4/2005 | Benchetrit |
| 6,929,631 B1 | 8/2005 | Brugger et al. |
| 6,949,084 B2 | 9/2005 | Marggi et al. |
| 6,953,453 B2 | 10/2005 | Recinella et al. |
| 6,962,577 B2 | 11/2005 | Tallarida et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| D518,573 S | 4/2006 | French |
| 7,033,335 B2 | 4/2006 | Haarala et al. |
| 7,033,339 B1 | 4/2006 | Lynn |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,124,570 B2 | 10/2006 | Blatter et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,186,236 B2 | 3/2007 | Gibson et al. |
| 7,191,011 B2 | 3/2007 | Cantlon |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,232,429 B2 | 6/2007 | Moreci |
| 7,235,067 B2 | 6/2007 | Morris et al. |
| D546,440 S | 7/2007 | Burnside |
| 7,242,982 B2 | 7/2007 | Singhal et al. |
| 7,248,668 B2 | 7/2007 | Galkin |
| 7,252,469 B2 | 8/2007 | Zaluzec et al. |
| 7,252,649 B2 | 8/2007 | Sherry |
| 7,261,705 B2 | 8/2007 | Edoga et al. |
| D550,355 S | 9/2007 | Racz et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside et al. |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,442 S | 2/2008 | Blateri |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| 7,485,148 B2 | 2/2009 | Wozencroft et al. |
| 7,497,850 B2 | 3/2009 | Halili |
| D590,499 S | 4/2009 | Chesnin |
| 7,552,853 B2 | 6/2009 | Mas et al. |
| 7,553,298 B2 | 6/2009 | Hunt et al. |
| D595,892 S | 7/2009 | Smith et al. |
| 7,563,025 B2 | 7/2009 | Kay |
| 7,618,411 B2 | 11/2009 | Appling |
| 7,628,776 B2 | 12/2009 | Gibson et al. |
| 7,658,196 B2 | 2/2010 | Ferreri et al. |
| D612,479 S | 3/2010 | Zawacki et al. |
| D613,394 S | 4/2010 | Linden |
| 7,713,251 B2 | 5/2010 | Tallarida et al. |
| 7,722,580 B2 | 5/2010 | Dicarlo et al. |
| D619,242 S | 7/2010 | Zinn et al. |
| 7,766,880 B1 | 8/2010 | Spinoza |
| 7,785,302 B2 | 8/2010 | Powers |
| 7,803,143 B2 | 9/2010 | Tallarida et al. |
| 7,806,888 B2 | 10/2010 | Frassica |
| 7,811,266 B2 | 10/2010 | Eliasen |
| D629,503 S | 12/2010 | Caffey et al. |
| 7,846,139 B2 | 12/2010 | Zinn et al. |

(56) References Cited

U.S. PATENT DOCUMENTS

| | | |
|---|---|---|
| 7,850,660 B2 | 12/2010 | Uth et al. |
| 7,862,546 B2 | 1/2011 | Conlon et al. |
| D634,840 S | 3/2011 | Lombardi, III et al. |
| 7,909,804 B2 | 3/2011 | Stats |
| 7,931,619 B2 | 4/2011 | Diamond et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,007,474 B2 | 8/2011 | Uth et al. |
| 8,021,324 B2 | 9/2011 | Bizup et al. |
| 8,025,639 B2 | 9/2011 | Powers et al. |
| 8,029,482 B2 | 10/2011 | Maniar et al. |
| D650,475 S | 12/2011 | Smith et al. |
| 8,075,536 B2 | 12/2011 | Gray et al. |
| 8,092,435 B2 | 1/2012 | Beling et al. |
| 8,147,455 B2 | 4/2012 | Butts et al. |
| 8,172,894 B2 | 5/2012 | Schmid et al. |
| 8,172,896 B2 | 5/2012 | McNamara et al. |
| 8,177,762 B2 | 5/2012 | Beasley et al. |
| 8,182,453 B2 | 5/2012 | Eliasen |
| 8,197,454 B2 | 6/2012 | Mann et al. |
| 8,202,259 B2 | 6/2012 | Evans et al. |
| 8,257,325 B2 | 9/2012 | Schweikert et al. |
| D676,955 S | 2/2013 | Orome |
| 8,366,687 B2 | 2/2013 | Girard et al. |
| 8,377,034 B2 | 2/2013 | Tallarida et al. |
| 8,382,723 B2 | 2/2013 | Powers et al. |
| 8,382,724 B2 | 2/2013 | Maniar et al. |
| 8,409,153 B2 | 4/2013 | Tallarida et al. |
| 8,475,417 B2 | 7/2013 | Powers et al. |
| 8,545,460 B2 | 10/2013 | Beasley et al. |
| 8,585,660 B2 | 11/2013 | Murphy |
| 8,585,663 B2 | 11/2013 | Powers et al. |
| 8,603,052 B2 | 12/2013 | Powers et al. |
| 8,608,712 B2 | 12/2013 | Bizup et al. |
| 8,608,713 B2 | 12/2013 | Beasley et al. |
| 8,641,676 B2 | 2/2014 | Butts et al. |
| 8,641,688 B2 | 2/2014 | Powers et al. |
| 8,805,478 B2 | 8/2014 | Powers et al. |
| 8,852,160 B2 | 10/2014 | Schweikert et al. |
| 8,932,271 B2 | 1/2015 | Hamatake et al. |
| 8,939,947 B2 | 1/2015 | Maniar et al. |
| 8,998,860 B2 | 4/2015 | Sheetz et al. |
| 9,079,004 B2 | 7/2015 | Wiley et al. |
| 9,248,268 B2 | 2/2016 | Wiley et al. |
| 9,265,912 B2 | 2/2016 | Draper et al. |
| 9,295,733 B2 | 3/2016 | Trieu |
| 9,421,352 B2 | 8/2016 | Butts et al. |
| 9,474,888 B2 | 10/2016 | Wiley et al. |
| 9,579,496 B2 | 2/2017 | Evans et al. |
| 9,603,992 B2 | 3/2017 | Powers |
| 9,603,993 B2 | 3/2017 | Powers |
| 9,642,986 B2 | 5/2017 | Beasley |
| 9,682,186 B2 | 6/2017 | Powers et al. |
| 9,717,895 B2 | 8/2017 | Wiley et al. |
| 9,937,337 B2 | 4/2018 | Powers et al. |
| 10,016,585 B2 | 7/2018 | Powers et al. |
| 10,052,470 B2 | 8/2018 | Powers et al. |
| 10,052,471 B2 | 8/2018 | Hamatake et al. |
| 10,086,186 B2 | 10/2018 | Evans et al. |
| 10,092,725 B2 | 10/2018 | Beasley |
| 10,155,101 B2 | 12/2018 | Wiley et al. |
| 10,183,157 B2 | 1/2019 | Powers et al. |
| 10,238,850 B2 | 3/2019 | Maniar et al. |
| 10,265,512 B2 | 4/2019 | Wiley et al. |
| 10,307,581 B2 | 6/2019 | Hibdon et al. |
| 2001/0016699 A1 | 8/2001 | Burbank et al. |
| 2001/0016717 A1 | 8/2001 | Haarala et al. |
| 2001/0047165 A1 | 11/2001 | Makower et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0013557 A1 | 1/2002 | Sherry |
| 2002/0052576 A1 | 5/2002 | Massengale |
| 2002/0055715 A1 | 5/2002 | Young et al. |
| 2002/0095205 A1 | 7/2002 | Edwin et al. |
| 2002/0121530 A1 | 9/2002 | Socier |
| 2002/0138068 A1 | 9/2002 | Watson et al. |
| 2002/0169418 A1 | 11/2002 | Menzi et al. |
| 2002/0173769 A1 | 11/2002 | Gray et al. |
| 2002/0173772 A1 | 11/2002 | Olsen |
| 2002/0183846 A1 | 12/2002 | Kuslich et al. |
| 2002/0188282 A1 | 12/2002 | Greenberg |
| 2003/0028173 A1 | 2/2003 | Forsberg |
| 2003/0032918 A1 | 2/2003 | Quinn |
| 2003/0093029 A1 | 5/2003 | McGuckin et al. |
| 2003/0109856 A1 | 6/2003 | Sherry |
| 2003/0130627 A1 | 7/2003 | Smith et al. |
| 2003/0135388 A1 | 7/2003 | Martucci et al. |
| 2003/0139812 A1 | 7/2003 | Garcia |
| 2003/0141477 A1 | 7/2003 | Miller |
| 2003/0181878 A1 | 9/2003 | Tallarida et al. |
| 2003/0191452 A1 | 10/2003 | Meglin et al. |
| 2003/0208184 A1 | 11/2003 | Burke et al. |
| 2003/0216694 A1 | 11/2003 | Tollini |
| 2003/0217659 A1 | 11/2003 | Yamamoto et al. |
| 2004/0002693 A1 | 1/2004 | Bright et al. |
| 2004/0006316 A1 | 1/2004 | Patton |
| 2004/0020462 A1 | 2/2004 | Sauler et al. |
| 2004/0020492 A1 | 2/2004 | Dubrul et al. |
| 2004/0024361 A1 | 2/2004 | Fago et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0078000 A1 | 4/2004 | Borchard et al. |
| 2004/0086568 A1 | 5/2004 | Ditizio et al. |
| 2004/0087877 A1 | 5/2004 | Besz et al. |
| 2004/0087885 A1 | 5/2004 | Kawano et al. |
| 2004/0106878 A1 | 6/2004 | Skujins et al. |
| 2004/0106891 A1 | 6/2004 | Langan et al. |
| 2004/0106942 A1 | 6/2004 | Taylor et al. |
| 2004/0116901 A1 | 6/2004 | Appling |
| 2004/0133173 A1 | 7/2004 | Edoga et al. |
| 2004/0156472 A1 | 8/2004 | Galkin |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0186444 A1 | 9/2004 | Daly et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0204759 A1 | 10/2004 | Blom et al. |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0010176 A1 | 1/2005 | Dikeman et al. |
| 2005/0010286 A1 | 1/2005 | Vijay |
| 2005/0027234 A1 | 2/2005 | Waggoner et al. |
| 2005/0027261 A1 | 2/2005 | Weaver et al. |
| 2005/0038390 A1 | 2/2005 | Fago et al. |
| 2005/0044759 A1 | 3/2005 | Schweikert |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0080401 A1 | 4/2005 | Peavey |
| 2005/0085778 A1 | 4/2005 | Parks |
| 2005/0086071 A1 | 4/2005 | Fox et al. |
| 2005/0113806 A1 | 5/2005 | De Carvalho et al. |
| 2005/0124980 A1 | 6/2005 | Sanders |
| 2005/0131352 A1 | 6/2005 | Conlon et al. |
| 2005/0148866 A1 | 7/2005 | Gunderson |
| 2005/0148869 A1 | 7/2005 | Masuda |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0241203 A1 | 11/2005 | Lizotte et al. |
| 2005/0256451 A1 | 11/2005 | Adams et al. |

(56) References Cited

U.S. PATENT DOCUMENTS

| | | |
|---|---|---|
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0020256 A1 | 1/2006 | Bell et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0149189 A1 | 7/2006 | Diamond et al. |
| 2006/0171980 A1 | 8/2006 | Helmus et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0184142 A1 | 8/2006 | Schon |
| 2006/0217359 A1 | 9/2006 | Wentworth et al. |
| 2006/0217659 A1 | 9/2006 | Patton |
| 2006/0217668 A1 | 9/2006 | Schulze et al. |
| 2006/0224128 A1 | 10/2006 | Lurvey et al. |
| 2006/0224129 A1 | 10/2006 | Beasley et al. |
| 2006/0224235 A1 | 10/2006 | Rucker |
| 2006/0241465 A1 | 10/2006 | Huennekens et al. |
| 2006/0247584 A1 | 11/2006 | Sheetz et al. |
| 2006/0253076 A1 | 11/2006 | Butts |
| 2006/0264897 A1 | 11/2006 | Lobl et al. |
| 2006/0264898 A1 | 11/2006 | Beasley et al. |
| 2006/0271012 A1 | 11/2006 | Canaud et al. |
| 2007/0003603 A1 | 1/2007 | Karandikar et al. |
| 2007/0004981 A1 | 1/2007 | Boese et al. |
| 2007/0007839 A1 | 1/2007 | Lin |
| 2007/0010881 A1 | 1/2007 | Soye et al. |
| 2007/0016162 A1 | 1/2007 | Burbank et al. |
| 2007/0049806 A1 | 3/2007 | Adams et al. |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083111 A1 | 4/2007 | Hossack et al. |
| 2007/0083156 A1 | 4/2007 | Muto et al. |
| 2007/0100302 A1 | 5/2007 | Dicarlo et al. |
| 2007/0112332 A1 | 5/2007 | Harding et al. |
| 2007/0120683 A1 | 5/2007 | Flippen et al. |
| 2007/0123831 A1 | 5/2007 | Haindl et al. |
| 2007/0135775 A1 | 6/2007 | Edoga et al. |
| 2007/0149920 A1 | 6/2007 | Michels et al. |
| 2007/0149921 A1 | 6/2007 | Michels et al. |
| 2007/0149947 A1 | 6/2007 | Byrum |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0207335 A1 | 9/2007 | Karandikar et al. |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0233042 A1 | 10/2007 | Moehle et al. |
| 2007/0255226 A1 | 11/2007 | Tennican et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276355 A1 | 11/2007 | Nielsen et al. |
| 2007/0282308 A1 | 12/2007 | Bell |
| 2007/0293800 A1 | 12/2007 | McMaken et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0021392 A1 | 1/2008 | Lurvey et al. |
| 2008/0039820 A1 | 2/2008 | Sommers et al. |
| 2008/0048855 A1 | 2/2008 | Berger |
| 2008/0051731 A1 | 2/2008 | Schweikert et al. |
| 2008/0108949 A1 | 5/2008 | Beasley et al. |
| 2008/0114308 A1 | 5/2008 | di Palma et al. |
| 2008/0133265 A1 | 6/2008 | Silkaitis et al. |
| 2008/0137923 A1 | 6/2008 | Spahn |
| 2008/0138387 A1 | 6/2008 | Machiraju |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118612 A1 | 5/2009 | Grunwald et al. |
| 2009/0118683 A1 | 5/2009 | Hanson et al. |
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0216216 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2009/0227964 A1 | 9/2009 | DiCarlo et al. |
| 2009/0264901 A1 | 10/2009 | Franklin et al. |
| 2009/0264990 A1 | 10/2009 | Bruszewski et al. |
| 2009/0315684 A1 | 12/2009 | Sacco et al. |
| 2009/0322541 A1 | 12/2009 | Jones et al. |
| 2010/0010339 A1 | 1/2010 | Smith et al. |
| 2010/0042073 A1 | 2/2010 | Oster et al. |
| 2010/0063451 A1 | 3/2010 | Gray et al. |
| 2010/0069743 A1 | 3/2010 | Sheetz et al. |
| 2010/0106094 A1 | 4/2010 | Fisher et al. |
| 2010/0121283 A1 | 5/2010 | Hamatake et al. |
| 2010/0211026 A2 | 8/2010 | Sheetz et al. |
| 2010/0268165 A1 | 10/2010 | Maniar et al. |
| 2010/0268174 A1 | 10/2010 | Steinke et al. |
| 2010/0319700 A1 | 12/2010 | Ng et al. |
| 2011/0021922 A1 | 1/2011 | Berard-Anderson et al. |
| 2011/0054312 A1 | 3/2011 | Bell et al. |
| 2011/0092921 A1 | 4/2011 | Beling et al. |
| 2011/0098662 A1 | 4/2011 | Zinn |
| 2011/0098663 A1 | 4/2011 | Zinn |
| 2011/0118677 A1 | 5/2011 | Wiley et al. |
| 2011/0160673 A1 | 6/2011 | Magalich et al. |
| 2011/0183712 A1 | 7/2011 | Eckstein et al. |
| 2011/0213700 A1 | 9/2011 | Sant'Anselmo |
| 2011/0257609 A1 | 10/2011 | Bizup et al. |
| 2011/0264058 A1 | 10/2011 | Linden et al. |
| 2011/0271856 A1 | 11/2011 | Fisher et al. |
| 2011/0275930 A1 | 11/2011 | Jho et al. |
| 2011/0276015 A1 | 11/2011 | Powers et al. |
| 2011/0288502 A1 | 11/2011 | Hibdon et al. |
| 2011/0288503 A1 | 11/2011 | Magalich et al. |
| 2011/0311337 A1 | 12/2011 | Amin et al. |
| 2012/0018073 A1 | 1/2012 | Maniar et al. |
| 2012/0059250 A1 | 3/2012 | Gray et al. |
| 2012/0065622 A1 | 3/2012 | Cornish et al. |
| 2012/0078201 A1 | 3/2012 | Mikami |
| 2012/0078202 A1 | 3/2012 | Beling et al. |
| 2012/0191071 A1 | 7/2012 | Butts et al. |
| 2012/0226244 A1 | 9/2012 | Beasley et al. |
| 2012/0259296 A1 | 10/2012 | Sheetz et al. |
| 2012/0283560 A1 | 11/2012 | Schweikert et al. |
| 2012/0302969 A1 | 11/2012 | Wiley et al. |
| 2013/0165773 A1 | 6/2013 | Powers et al. |
| 2013/0172733 A1 | 7/2013 | Maniar et al. |
| 2013/0218103 A1 | 8/2013 | Tallarida et al. |
| 2013/0225990 A1 | 8/2013 | Powers et al. |
| 2013/0225991 A1 | 8/2013 | Powers |
| 2013/0245574 A1 | 9/2013 | Powers et al. |
| 2013/0338494 A1 | 12/2013 | Wiley et al. |
| 2014/0058275 A1 | 2/2014 | Gregorich et al. |
| 2014/0081219 A1 | 3/2014 | Powers et al. |
| 2014/0100534 A1 | 4/2014 | Beasley et al. |
| 2014/0107619 A1 | 4/2014 | Butts |
| 2014/0330118 A1 | 11/2014 | Powers et al. |

(56) References Cited

U.S. PATENT DOCUMENTS

| | | |
|---|---|---|
| 2014/0350396 A1 | 11/2014 | Powers et al. |
| 2015/0008891 A1 | 1/2015 | Li et al. |
| 2015/0025478 A1 | 1/2015 | Hibdon et al. |
| 2015/0088091 A1 | 3/2015 | Beasley et al. |
| 2015/0112284 A1 | 4/2015 | Hamatake et al. |
| 2015/0290445 A1 | 10/2015 | Powers et al. |
| 2015/0290446 A1 | 10/2015 | Wiley et al. |
| 2017/0028185 A1 | 2/2017 | Wiley et al. |
| 2017/0157383 A1 | 6/2017 | Evans et al. |
| 2017/0232232 A1 | 8/2017 | Beasley |
| 2017/0246441 A1 | 8/2017 | Powers et al. |
| 2017/0319842 A1 | 11/2017 | Wiley et al. |
| 2018/0161565 A1 | 6/2018 | Maniar et al. |
| 2018/0311488 A1 | 11/2018 | Powers et al. |
| 2018/0353743 A1 | 12/2018 | Hamatake et al. |
| 2019/0038871 A1 | 2/2019 | Beasley |
| 2019/0060628 A1 | 2/2019 | Evans et al. |
| 2019/0111242 A1 | 4/2019 | Wiley et al. |
| 2019/0134373 A1 | 5/2019 | Barron et al. |
| 2019/0151641 A1 | 5/2019 | Powers et al. |
| 2019/0217073 A1 | 7/2019 | Maniar et al. |
| 2019/0252603 A1 | 8/2019 | Wiley et al. |
| 2019/0275311 A1 | 9/2019 | Hibdon et al. |

FOREIGN PATENT DOCUMENTS

| | | |
|---|---|---|
| CA | 2692142 A1 | 12/2008 |
| CA | 2693972 A1 | 1/2009 |
| CA | 2757836 C | 5/2017 |
| CN | 102421469 A | 4/2012 |
| CN | 102612343 A | 7/2012 |
| DE | 3618390 C1 | 11/1987 |
| DE | 3720414 A1 | 12/1987 |
| DE | 42 25 524 A1 | 2/1994 |
| DE | 29512576 U1 | 10/1995 |
| DE | 10346470 A1 | 5/2005 |
| DE | 10 2009 018837 A1 | 11/2010 |
| EP | 0128525 A2 | 12/1984 |
| EP | 0134745 A1 | 3/1985 |
| EP | 0343910 A2 | 11/1989 |
| EP | 0366814 A1 | 5/1990 |
| EP | 0239244 | 9/1991 |
| EP | 0534782 A1 | 3/1993 |
| EP | 0537892 A1 | 4/1993 |
| EP | 0619101 A1 | 10/1994 |
| EP | 1238682 A2 | 9/2002 |
| EP | 1486229 A1 | 12/2004 |
| EP | 1635899 A2 | 3/2006 |
| EP | 1858565 A1 | 11/2007 |
| EP | 1874393 A1 | 1/2008 |
| EP | 1896117 A2 | 3/2008 |
| EP | 1998842 A2 | 12/2008 |
| EP | 2004272 A2 | 12/2008 |
| EP | 2018209 A2 | 1/2009 |
| EP | 2081634 A1 | 7/2009 |
| EP | 2164559 A1 | 3/2010 |
| EP | 2167182 A1 | 3/2010 |
| EP | 2180915 A1 | 5/2010 |
| EP | 2190517 A1 | 6/2010 |
| EP | 2320974 A1 | 5/2011 |
| EP | 2324879 A2 | 5/2011 |
| EP | 2365838 A1 | 9/2011 |
| EP | 2571563 A1 | 3/2013 |
| EP | 2601999 A1 | 6/2013 |
| EP | 2324879 B1 | 1/2014 |
| EP | 2324878 B1 | 8/2014 |
| EP | 2308547 B1 | 9/2014 |
| EP | 2324880 B1 | 12/2014 |
| EP | 1 965 854 B1 | 9/2015 |
| EP | 2939703 B1 | 3/2017 |
| EP | 2416828 B1 | 2/2018 |
| FR | 1509165 A | 1/1968 |
| FR | 2508008 A1 | 12/1982 |
| FR | 2809315 A1 | 11/2001 |
| GB | 178998 A | 5/1922 |
| GB | 749942 A | 6/1956 |
| GB | 966137 A | 8/1964 |
| GB | 1559140 A | 1/1980 |
| GB | 2102398 A | 2/1983 |
| GB | 2191701 A | 12/1987 |
| GB | 2350352 A | 11/2000 |
| JP | 62155857 A | 7/1987 |
| JP | 62281966 A | 12/1987 |
| JP | 64-011562 | 1/1989 |
| JP | H05-200107 A | 8/1993 |
| JP | 6296633 A | 10/1994 |
| JP | 2000-79168 | 3/2000 |
| JP | 2000-079168 A | 3/2000 |
| JP | 2002500076 A | 1/2002 |
| JP | 2002-83281 A | 3/2002 |
| JP | 2002-209910 A | 7/2002 |
| JP | 2002-531149 A | 9/2002 |
| JP | 2003-510136 A | 3/2003 |
| JP | 2004-350937 A | 12/2004 |
| JP | 2006-500087 A | 1/2006 |
| JP | 2007-203070 A | 8/2007 |
| JP | 2007-275548 A | 10/2007 |
| JP | 2007-533368 A | 11/2007 |
| JP | 3142990 U | 7/2008 |
| JP | 2008-539025 A | 11/2008 |
| JP | 2009-077965 A | 4/2009 |
| JP | 2009-142520 A | 7/2009 |
| JP | 2009-540932 A | 11/2009 |
| JP | 2012-523284 A | 10/2012 |
| JP | 2012-236040 A | 12/2012 |
| JP | 2013-510652 | 3/2013 |
| JP | 2013-526376 A | 6/2013 |
| JP | 6018822 B2 | 11/2016 |
| WO | 8600213 A1 | 1/1986 |
| WO | 1986000213 A1 | 1/1986 |
| WO | 1988011309 A1 | 11/1989 |
| WO | 9001958 A1 | 3/1990 |
| WO | 1990001958 A1 | 3/1990 |
| WO | 9206732 A1 | 4/1992 |
| WO | 1993000945 A1 | 1/1993 |
| WO | 9305730 A1 | 4/1993 |
| WO | 1993005730 A1 | 4/1993 |
| WO | 1993008986 A1 | 5/1993 |
| WO | 9405351 A1 | 3/1994 |
| WO | 9516480 A1 | 6/1995 |
| WO | 1995015194 | 6/1995 |
| WO | 96-35477 A1 | 11/1996 |
| WO | 9701370 A1 | 1/1997 |
| WO | 1997001370 A1 | 1/1997 |
| WO | 1997006845 A1 | 2/1997 |
| WO | 9711726 A1 | 4/1997 |
| WO | 9723255 A1 | 7/1997 |
| WO | 9726931 A1 | 7/1997 |
| WO | 1998017337 A1 | 4/1998 |
| WO | 9818506 A1 | 5/1998 |
| WO | 1998031417 A2 | 7/1998 |
| WO | 99/10250 A1 | 3/1999 |
| WO | 1999034859 A1 | 7/1999 |
| WO | 9938553 A1 | 8/1999 |
| WO | 9942166 A1 | 8/1999 |
| WO | 0012171 A1 | 3/2000 |
| WO | 0016844 A1 | 3/2000 |
| WO | 00/20050 A1 | 4/2000 |
| WO | 0033901 A1 | 6/2000 |
| WO | 2000033901 A1 | 6/2000 |
| WO | 0123023 A1 | 4/2001 |
| WO | 2001023023 A1 | 4/2001 |
| WO | 0160444 A1 | 8/2001 |
| WO | 01/70304 A1 | 9/2001 |
| WO | 2001095813 | 12/2001 |
| WO | 0247549 A1 | 6/2002 |
| WO | 2002047549 A1 | 6/2002 |
| WO | 03/030962 A2 | 4/2003 |
| WO | 03084832 A1 | 10/2003 |
| WO | 03090509 A2 | 11/2003 |
| WO | 2004004800 A2 | 1/2004 |
| WO | 2004/012787 A2 | 2/2004 |
| WO | 2004028611 A1 | 4/2004 |
| WO | 2004071555 A2 | 8/2004 |

(56) References Cited

FOREIGN PATENT DOCUMENTS

| | | |
|---|---|---|
| WO | 2004091434 A2 | 10/2004 |
| WO | 2005037055 A2 | 4/2005 |
| WO | 2005068009 A1 | 7/2005 |
| WO | 2005072627 A1 | 8/2005 |
| WO | 2005/089833 A1 | 9/2005 |
| WO | 2006078915 A2 | 7/2006 |
| WO | 2006096686 A1 | 9/2006 |
| WO | 2006116438 A2 | 11/2006 |
| WO | 2006116613 A1 | 11/2006 |
| WO | 2006130133 A1 | 12/2006 |
| WO | 2006134100 A1 | 12/2006 |
| WO | 2007041471 A2 | 4/2007 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2007/149546 A2 | 12/2007 |
| WO | 2008008126 A2 | 1/2008 |
| WO | 2008/024440 A1 | 2/2008 |
| WO | 2008019236 A1 | 2/2008 |
| WO | 2008/048461 A2 | 4/2008 |
| WO | 2008048361 A1 | 4/2008 |
| WO | 2008062173 A1 | 5/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |
| WO | 2009035582 A1 | 3/2009 |
| WO | 2009046439 A2 | 4/2009 |
| WO | 2009046725 A1 | 4/2009 |
| WO | 2009108669 A1 | 9/2009 |
| WO | 2010030351 A1 | 3/2010 |
| WO | 2010062633 A1 | 6/2010 |
| WO | 2010118144 A1 | 10/2010 |
| WO | 2011046604 A2 | 4/2011 |
| WO | 2011053499 A1 | 5/2011 |
| WO | 2011056619 A1 | 5/2011 |
| WO | 2011062750 A1 | 5/2011 |
| WO | 2011133950 A1 | 10/2011 |
| WO | 2011146649 A1 | 11/2011 |
| WO | 2013/165935 A1 | 11/2013 |
| WO | 2014031763 A2 | 2/2014 |

OTHER PUBLICATIONS

U.S. Appl. No. 12/917,323, filed Nov. 1, 2010 Non-Final Office Action dated Aug. 26, 2014.
U.S. Appl. No. 12/917,323, filed Nov. 1, 2010 Notice of Allowance dated Jan. 21, 2015.
U.S. Appl. No. 12/419,854, filed Apr. 7, 2009 Non-Final Office Action dated Aug. 5, 2011.
U.S. Appl. No. 13/110,734, filed May 18, 2011 Non-Final Office Action dated Jul. 7, 2014.
U.S. Appl. No. 13/113,834, filed May 23, 2011 Final Office Action dated Nov. 23, 2012.
U.S. Appl. No. 13/113,834, filed May 23, 2011 Non-Final Office Action dated Jul. 17, 2012.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/438,586, filed Apr. 3, 2012 Non-Final Office Action dated Sep. 19, 2012.
U.S. Appl. No. 13/438,586, filed Apr. 3, 2012 Notice of Allowance dated Sep. 16, 2013.
U.S. Appl. No. 13/471,219, filed May 14, 2012 Non-Final Office Action dated Jul. 10, 2013.
U.S. Appl. No. 13/524,712, filed Jun. 15, 2012 Advisory Action dated May 7, 2014.
U.S. Appl. No. 13/524,712, filed Jun. 15, 2012 Final Office Action dated Mar. 3, 2014.
U.S. Appl. No. 13/524,712, filed Jun. 15, 2012 Non-Final Office Action dated Aug. 21, 2014.
U.S. Appl. No. 13/524,712, filed Jun. 15, 2012 Non-Final Office Action dated Oct. 22, 2013.
U.S. Appl. No. 13/524,712, filed Jun. 15, 2012 Notice of Allowance dated Dec. 12, 2014.
U.S. Appl. No. 13/571,088, filed Aug. 9, 2012 Final Office Action dated Jul. 16, 2013.
U.S. Appl. No. 13/571,088, filed Aug. 9, 2012 Final Office Action dated Jul. 6, 2015.
U.S. Appl. No. 13/571,088, filed Aug. 9, 2012 Non-Final Office Action dated Feb. 27, 2013.
U.S. Appl. No. 13/571,088, filed Aug. 9, 2012 Non-Final Office Action dated Jan. 7, 2015.
U.S. Appl. No. 13/571,088, filed Aug. 9, 2012 Notice of Allowance dated Sep. 16, 2015.
U.S. Appl. No. 13/776,451, filed Feb. 25, 2013 Non-Final Office Action dated Jul. 24, 2013.
U.S. Appl. No. 13/776,517, filed Feb. 25, 2013 Final Office Action dated Jun. 30, 2014.
U.S. Appl. No. 13/776,517, filed Feb. 25, 2013 Non-Final Office Action dated Feb. 27, 2014.
U.S. Appl. No. 13/776,517, filed Feb. 25, 2013 Non-Final Office Action dated Nov. 15, 2013.
U.S. Appl. No. 13/776,517, filed Feb. 25, 2013 Notice of Allowance dated Sep. 23, 2014.
U.S. Appl. No. 13/801,893, filed Mar. 13, 2013 Notice of Allowance dated Sep. 24, 2015.
U.S. Appl. No. 13/853,942, filed Mar. 29, 2013 Non-Final Office Action dated Jul. 26, 2013.
U.S. Appl. No. 13/853,956, filed Mar. 29, 2013 Final Office Action dated Feb. 20, 2015.
U.S. Appl. No. 13/853,956, filed Mar. 29, 2013 Final Office Action dated Jan. 10, 2017.
U.S. Appl. No. 13/853,956, filed Mar. 29, 2013 Final Office Action dated Oct. 18, 2016.
U.S. Appl. No. 13/853,956, filed Mar. 29, 2013 Non-Final Office Action dated Dec. 3, 2013.
U.S. Appl. No. 13/853,956, filed Mar. 29, 2013 Non-Final Office Action dated Jun. 16, 2016.
U.S. Appl. No. 13/853,956, filed Mar. 29, 2013 Non-Final Office Action dated Sep. 15, 2014.
U.S. Appl. No. 13/853,961, filed Mar. 29, 2013 Final Office Action dated Feb. 20, 2015.
U.S. Appl. No. 13/853,961, filed Mar. 29, 2013 Final Office Action dated Jan. 9, 2017.
U.S. Appl. No. 13/853,961, filed Mar. 29, 2013 Non-Final Office Action dated Dec. 3, 2013.
U.S. Appl. No. 13/853,961, filed Mar. 29, 2013 Non-Final Office Action dated Jun. 15, 2016.
U.S. Appl. No. 13/853,961, filed Mar. 29, 2013 Non-Final Office Action dated Oct. 18, 2016.
U.S. Appl. No. 13/853,961, filed Mar. 29, 2013 Non-Final Office Action dated Sep. 12, 2014.
U.S. Appl. No. 13/972,538, filed Aug. 21, 2013 Non-Final Office Action dated Feb. 3, 2016.
U.S. Appl. No. 14/083,250, filed Nov. 18, 2013 Non-Final Office Action dated Dec. 12, 2016.
U.S. Appl. No. 14/083,250, filed Nov. 18, 2013 Non-Final Office Action dated Apr. 1, 2016.
U.S. Appl. No. 14/104,354, filed Dec. 12, 2013 Final Office Action dated Jun. 15, 2018.
U.S. Appl. No. 14/104,354, filed Dec. 12, 2013 Final Office Action dated Jun. 21, 2016.

(56) References Cited

OTHER PUBLICATIONS

U.S. Appl. No. 14/104,354, filed Dec. 12, 2013 Final Office Action dated May 31, 2017.
U.S. Appl. No. 14/104,354, filed Dec. 12, 2013 Non-Final Office Action dated Feb. 26, 2016.
EP 06751411 filed Apr. 25, 2006 Decision Revoking the European Patent dated Aug. 1, 2012.
EP 06751411 filed Apr. 25, 2006 Office Action dated Aug. 10, 2009.
EP 06751411 filed Apr. 25, 2006 Opposition by Aesculap AG dated Oct. 6, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 18, 2011.
EP 06751664.1 filed Apr. 27, 2006 First Examination Report dated Jul. 11, 2013.
EP 06751664.1 filed Apr. 27, 2006 Second Examination Report dated Dec. 17, 2014.
EP 06845998 filed Dec. 21, 2006 Office Action dated Mar. 10, 2011.
EP 06845998 filed Dec. 21, 2006 Supplementary Search Report dated Jul. 22, 2010.
EP 06845998.1 filed Dec. 21, 2006 Examination Report dated Feb. 6, 2014.
EP 06845998.1 filed Dec. 21, 2006 Examination Report dated May 13, 2013.
EP 06845998.1 filed Dec. 21, 2006 Examination Report dated Nov. 7, 2012.
EP 06845998.1 filed Dec. 21, 2006 Summons for Oral Proceedings dated Sep. 30, 2014.
EP 09824195.3 filed Apr. 13, 2011 Extended European Search Report dated Apr. 28, 2017.
EP 10 831 973.2 filed May 30, 2012 Extended European Search Report dated Jul. 4, 2014.
EP 10 831 973.2 filed May 30, 2012 Intent to Grant dated Feb. 12, 2018.
EP 10 831 973.2 filed May 30, 2012 Office Action dated Aug. 18, 2017.
EP 10183380.4 filed Apr. 25, 2006 European Search Report dated May 22, 2013.
EP 10183382.0 filed Apr. 25, 2006 European Search Report dated May 22, 2013.
EP 10183382.0 filed Apr. 25, 2006 Intent to Grant dated Mar. 7, 2014.
EP 10183394.5 filed Apr. 25, 2006 European Search Report dated May 22, 2013.
EP 10183394.5 filed Apr. 25, 2006 interlocutory decision dated Feb. 14, 2017.
EP 10183394.5 filed Apr. 25, 2006 Opponents Arguments in Support of the Appeal dated Jun. 30, 2017.
EP 10183394.5 filed Apr. 25, 2006 Opposition by Smiths Medical ASD, Inc. dated Apr. 25, 2014.
EP 10183394.5 filed Apr. 25, 2006 Opposition by Smiths Medical ASD, Inc. dated Dec. 2, 2015.
EP 10183394.5 filed Apr. 25, 2006 Opposition Grounds of Appeal dated May 17, 2017.
EP 10183394.5 filed Apr. 25, 2006 Response to Grounds of Appeal dated Nov. 3, 2017.
EP 10183398.6 filed Apr. 25, 2006 European Search Report dated May 22, 2013.
EP 10762377.9 filed Oct. 5, 2011 European Search Report dated Aug. 3, 2012.
EP 10762377.9 filed Oct. 5, 2011 Office Action dated Jul. 17, 2013.
EP 11784194.0 filed Nov. 29, 2012 Examination report dated Jul. 5, 2016.
EP 11784194.0 filed Nov. 29, 2012 extended European search report dated Feb. 21, 2014.
EP 13158343.7 filed Mar. 8, 2013 Examination Report dated Feb. 4, 2014.
EP 13158343.7 filed Mar. 8, 2013 Extended European Search Report dated May 14, 2013.
EP 13158343.7 filed Mar. 8, 2013 Summons to Attend Oral Proceedings dated Oct. 20, 2014.
EP 13764254.2 filed Sep. 10, 2014 Extended European Search Report dated Feb. 19, 2016.
EP 13764254.2 filed Sep. 10, 2014 Partial European Search Report dated Oct. 14, 2015.
EP 13830592.5 filed Feb. 24, 2015 Extended European Search Report dated Mar. 21, 2016.
EP 14198524.2 filed Dec. 17, 2014 Extended European Search Report dated Sep. 14, 2015.
EP 15180174 filed Aug. 7, 2015 European Search Report dated Jan. 4, 2016.
EP 15180174 filed Aug. 7, 2015 Office Action dated Jan. 13, 2017.
EP 16 193 913.7 filed Oct. 14, 2016 Extended European Search Report dated Apr. 13, 2017.
EP 16 193 913.7 filed Oct. 14, 2016 Office Action dated Feb. 13, 2018.
EP 99 964 086.5 filed Dec. 3, 1999 Office Action dated Dec. 15, 2005.
EP 99 964 086.5 filed Dec. 3, 1999 Office Action dated Mar. 1, 2005.
EP 99 964 086.5 filed Dec. 3, 1999 Office Action dated Mar. 30, 2005.
Ethanol Lock Technique for Prevention and Treatment of Central line-Associated Bloodstream Infections (Nebraska) Aug. 13, 2011, Accessed: Jun. 29, 2013 http://www.nebraskamed.com/app_files/pdf/careers/education-programs/asp/tnmc_etohlock_final.pdf.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
U.S. Appl. No. 95/002,090, filed Aug. 20, 2012 Office Action in and Order Granting/Denying Request for Inter Partes Reexamination dated Nov. 7, 2012.
U.S. Appl. No. 95/002,092, filed Aug. 20, 2012 Action Closing Prosecution dated Jun. 12, 2013.
U.S. Appl. No. 95/002,092, filed Aug. 20, 2012 Decision on Appeal in U.S. Pat. No. 7,959,615, dated Mar. 24, 2016.
U.S. Appl. No. 95/002,092, filed Aug. 20, 2012 Office Action in and Order Granting/Denying Request for Inter Partes Reexamination dated Nov. 13, 2012.
Vergara, et al., "Adverse Reactions to Contrast Medica in CT: Effects of Temperature and Ionic Property." Radiology, vol. 199, No. 2, May 1996.
Virot et al. "Long-term use of hemodialysis rooms LifeSite" Nephrologie vol. 24, No. 8, pp. 443-449 (2003).
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Wikipedia, "Port Catheter", Dec. 15, 2011.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
Gebauer, B. et al., "Contrast Media Power Injection Using Central Venous Port Catheters—Results of an In-Vitro Study," Experimental Radiology 2005: 177: 1417-1423.—Translation.
Herts, B. R., "Power Injection of Contrast Media Using Central Venous Catheters: Feasibility, Safety, and Efficacy" AJR 2001;176:447-453, Feb. 2001.
HMO 2002 Product Catalog, 2002.

(56) References Cited

OTHER PUBLICATIONS

Hou, Shaw-Min et al. "Comparisons of Outcomes and Survivals for Two Central Venous Access Port Systems." Journal of Surgical Oncology, 91:61-66, 2005.
Inamed Health, BioEnterics® Lap-Band® "Adjustable Gastric Banding System" Product Brochure, Dec. 2003.
Johnson, Kathleen A., "Power Injectable Portal Systems." Journal of Radiology Nursing, vol. 28, Issue 1, Mar. 2009.
JP 2007-558331 filed Mar. 6, 2006 Office Action dated Aug. 20, 2013.
JP 2007-558331 filed Mar. 6, 2006 Office Action dated Jan. 22, 2013.
JP 2007-558331 filed Mar. 6, 2006 Office Action dated May 17, 2011.
JP 2008-509056 filed Apr. 25, 2006 Office Action dated Apr. 4, 2012.
JP 2008-509056 filed Apr. 25, 2006 Office Action dated Jun. 7, 2011.
JP 2012-156976 filed Jul. 12, 2012 Notice of Reasons for Refusal dated Apr. 8, 2014.
JP 2012-156976 filed Jul. 12, 2012 Notice of Reasons for Refusal dated Aug. 27, 2013.
JP 2012-156976 filed Jul. 12, 2012 Office Action dated Jun. 28, 2016.
JP 2012-156976 filed Jul. 12, 2012 Submission of Documents by Third Party dated May 14, 2013.
JP 2012-156976 filed Mar. 6, 2006, Office Action dated Mar. 29, 2016.
JP 2012-156976 filed Mar. 6, 2006, Third Party Submission dated Jul. 29, 2015.
JP 2012-504826 filed Oct. 6, 2011 First Office Action dated Mar. 4, 2014.
JP 2012-504826 filed Oct. 6, 2011 Second Office Action dated Nov. 17, 2014.
JP 2013-209156 filed Oct. 4, 2013 Non-Final Office Action dated Oct. 7, 2014.
JP 2013-511339 filed Nov. 16, 2012 First Office Action dated Feb. 19, 2015.
JP 2013-511339 filed Nov. 16, 2012 Office Action and Pre-Appeal Report dated Apr. 12, 2016.
JP 2013-511339 filed Nov. 16, 2012 Office Action dated Dec. 16, 2016.
JP 2013-511339 filed Nov. 16, 2012 Second Office Action dated Oct. 16, 2015.
JP 2015-501762 filed Sep. 16, 2014 First Office Action dated Oct. 5, 2016.
JP 2015-501762 filed Sep. 16, 2014 Office Action dated Feb. 1, 2017.
JP 2015-501762 filed Sep. 16, 2014 Office Action dated Jan. 16, 2018.
JP 2015-528624 filed Feb. 20, 2015 Office Action dated Apr. 25, 2018.
JP 2015-528624 filed Feb. 20, 2015 Office Action dated May 31, 2017.
JP 2016-026954 filed Feb. 16, 2016 Office Action dated Aug. 16, 2017.
JP 2016-026954 filed Feb. 16, 2016 Office Action dated Dec. 15, 2016.
JP 6018822 filed Jul. 12, 2012 Request for Trial for Invalidation dated May 22, 2017.
JP2012-156976 filed Jul. 12, 2012 Amendment filed on Jul. 13, 2016 (Ref D06 of Request for Trial for Invalidation dated May 22, 2017).
JP2012-156976 filed Jul. 12, 2012 Amendment filed on Mar. 3, 2016 (Ref D04 of Request for Trial for Invalidation dated May 22, 2017).
JP2012-156976 filed Jul. 12, 2012 Amendment filed on Oct. 28, 2013 (Ref D03 of Request for Trial for Invalidation dated May 22, 2017).
JP2012-156976 filed Jul. 12, 2012 Office Action dated Aug. 20, 2013 (Ref D07 of Request for Trial for Invalidation dated May 22, 2017).
JP2012-156976 filed Jul. 12, 2012 Remarks filed on Mar. 3, 2016 (Ref D05 of Request for Trial for Invalidation dated May 22, 2017).
Kaste et al., "Safe use of power injectors with central and peripheral venous access devices for pediatric CT," Pediatr Radiol (1996) 26: 499-501.
KR 10-2011-7026328 filed Nov. 4, 2011 Notice of Last Preliminary Rejection dated Dec. 28, 2016.
KR 10-2011-7026328 filed Nov. 4, 2011 Notice of Preliminary Rejection dated Jun. 20, 2016.
KR 10-2017-7014546 filed May 29, 2017 Office Action dated Aug. 23, 2017.
KR 10-2017-7014546 filed May 29, 2017 Office Action dated Feb. 27, 2018.
L-CATH® for Ports, Luther Medical Products, Inc., Tustin, California, 2 pages, 1994.
LaMaitre Vascular "Port Implantations: using the OptiLock Implantable Port," product information, available at http://www.lemaitre.com/specs.pop.asp, last accessed Apr. 2003, 14 pages.
Lap-Band AP™ "System with Adjustable Gastric Banding system with Omniform™ Design," Product Brochure, Jul. 2007, 16 pages.
Lap-Band® System Access Port Fill Guide I, "9.75/10.0 cm Lap-Band System vs. 11 cm Lap-Band System: For Product Manufactured Prior to Jul. 2001" BioEnterics Corporation. Rev. B. Aug. 15, 2001.
Leslie et al., "A New Simple Power Injector," Am J Roentgenol 128: 381-384, Mar. 1977.
U.S. Appl. No. 14/104,354, filed Dec. 12, 2013 Non-Final Office Action dated Nov. 22, 2016.
U.S. Appl. No. 14/141,263, filed Dec. 26, 2013 Notice of Allowance dated Apr. 20, 2016.
U.S. Appl. No. 14/171,364, filed Feb. 3, 2014 Decision on Appeal dated Feb. 23, 2018.
U.S. Appl. No. 14/171,364, filed Feb. 3, 2014 Examiner's Answer dated Jul. 29, 2016.
U.S. Appl. No. 14/171,364, filed Feb. 3, 2014 Final Office Action dated Jun. 25, 2015.
U.S. Appl. No. 14/171,364, filed Feb. 3, 2014 Non-Final Office Action dated Feb. 12, 2015.
U.S. Appl. No. 14/171,364, filed Feb. 3, 2014 Notice of Allowance dated Mar. 26, 2018.
U.S. Appl. No. 14/455,660, filed Aug. 8, 2014 Final Office Action dated May 19, 2017.
U.S. Appl. No. 14/455,660, filed Aug. 8, 2014 Final Office Action dated Nov. 27, 2015.
U.S. Appl. No. 14/455,660, filed Aug. 8, 2014 Non-Final Office Action dated Jul. 6, 2015.
U.S. Appl. No. 14/455,660, filed Aug. 8, 2014 Non-Final Office Action dated Mar. 18, 2015.
U.S. Appl. No. 14/455,660, filed Aug. 8, 2014 Non-Final Office Action dated Oct. 14, 2016.
U.S. Appl. No. 14/455,660, filed Aug. 8, 2014 Notice of Allowance dated Nov. 24, 2017.
U.S. Appl. No. 14/508,227, filed Oct. 7, 2014 Non-Final Office Action dated Jun. 15, 2018.
U.S. Appl. No. 14/508,227, filed Oct. 7, 2014 Restriction Requirement dated Apr. 20, 2018.
U.S. Appl. No. 14/587,862, filed Dec. 31, 2014 Advisory Action dated Aug. 18, 2017.
U.S. Appl. No. 14/587,862, filed Dec. 31, 2014 Final Office Action dated May 4, 2017.
U.S. Appl. No. 14/587,862, filed Dec. 31, 2014 Non-Final Office Action dated Nov. 3, 2016.
U.S. Appl. No. 14/587,862, filed Dec. 31, 2014 Non-Final Office Action dated Sep. 28, 2017.
U.S. Appl. No. 14/587,862, filed Dec. 31, 2014 Notice of Allowance dated Apr. 6, 2018.
U.S. Appl. No. 14/599,376, filed Jan. 16, 2015 Advisory Action dated Aug. 23, 2016.
U.S. Appl. No. 14/599,376, filed Jan. 16, 2015 Final Office Action dated Jun. 8, 2016.

(56) References Cited

OTHER PUBLICATIONS

U.S. Appl. No. 14/599,376, filed Jan. 16, 2015 Final Office Action dated May 16, 2017.
U.S. Appl. No. 14/599,376, filed Jan. 16, 2015 Non-Final Office Action dated Feb. 3, 2016.
U.S. Appl. No. 14/599,376, filed Jan. 16, 2015 Non-Final Office Action dated May 14, 2018.
U.S. Appl. No. 14/599,376, filed Jan. 16, 2015 Non-Final Office Action dated Nov. 7, 2016.
U.S. Appl. No. 14/748,917, filed Jun. 24, 2015 Notice of Allowance dated May 9, 2018.
U.S. Appl. No. 14/750,174, filed Jun. 25, 2015 Non-Final Office Action dated Nov. 1, 2016.
U.S. Appl. No. 14/750,174, filed Jun. 25, 2015 Notice of Allowance dated Mar. 10, 2017.
U.S. Appl. No. 15/043,450, filed Feb. 12, 2016 Final Office Action dated Mar. 29, 2018.
U.S. Appl. No. 15/043,450, filed Feb. 12, 2016 Non-Final Office Action dated Nov. 30, 2017.
U.S. Appl. No. 15/290,621, filed Oct. 11, 2016 Non-Final Office Action dated May 16, 2018.
U.S. Appl. No. 15/442,371, filed Feb. 24, 2017 Non-Final Office Action dated Mar. 20, 2018.
U.S. Appl. No. 15/585,030, filed May 2, 2017 Notice of Allowance dated May 29, 2018.
U.S. Appl. No. 15/660,513, filed Jul. 26, 2017 Restriction Requirement dated Mar. 15, 2018.
U.S. Appl. No. 15/881,616, filed Jan. 26, 2018 Final Office Action dated Aug. 6, 2018.
U.S. Appl. No. 15/881,616, filed Jan. 26, 2018 Non-Final Office Action dated Mar. 28, 2018.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.
U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annemarie Boswell as inventors.
U.S. Appl. No. 29/382,235, filed Dec. 30, 2010 Non-Final Office Action dated Oct. 3, 2012.
U.S. Appl. No. 29/382,246, filed Dec. 30, 2010 Notice of Allowance dated Oct. 3, 2012.
U.S. Appl. No. 95/002,089, filed Aug. 20, 2012 Action Closing Prosecution dated Jun. 12, 2013.
U.S. Appl. No. 95/002,089, filed Aug. 20, 2012 Decision on Appeal in U.S. Pat. No. 7,785,302, dated Mar. 11, 2016.
U.S. Appl. No. 95/002,089, filed Aug. 20, 2012 Office Action in and Order Granting/Denying Request for Inter Partes Reexamination dated Nov. 7, 2012.
U.S. Appl. No. 95/002,090, filed Aug. 20, 2012 Action Closing Prosecution dated Jun. 12, 2013.
U.S. Appl. No. 95/002,090, filed Aug. 20, 2012 Decision on Appeal in U.S. Pat. No. 7,947,022, dated Mar. 29, 2016.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action dated Dec. 3, 2008.
U.S. Appl. No. 11/725,287, filed Mar. 19, 2007 Non-final Office Action dated Jun. 12, 2009.
U.S. Appl. No. 11/725,287, filed Mar. 19, 2007 Non-final Office Action dated Mar. 29, 2010.
U.S. Appl. No. 11/937,302, filed Nov. 8, 2007 Final Office Action dated Nov. 8, 2012.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Dec. 13, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/023,280, filed Jan. 31, 2008 Notice of Allowance dated Mar. 28, 2011.
U.S. Appl. No. 12/143,377, filed Jun. 20, 2008 Final Office Action dated Oct. 19, 2009.
U.S. Appl. No. 12/143,377, filed Jun. 20, 2008 Non-final Office Action dated Apr. 27, 2009.
U.S. Appl. No. 12/175,182, filed Jul. 17, 2008 Non-final Office Action dated Sep. 3, 2009.
U.S. Appl. No. 12/267,160, filed Nov. 7, 2008 Examiner's Answer dated Dec. 5, 2012.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Advisory Action dated May 17, 2013.
U.S. Appl. No. 12/419,854, filed Apr. 7, 2009 Final Office Action dated Feb. 14, 2013.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Jun. 26, 2012.
U.S. Appl. No. 12/419,854, filed Apr. 7, 2009 Notice of Allowance dated Apr. 7, 2014.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Non-Final Office Action dated Jun. 30, 2009.
U.S. Appl. No. 12/419,957, filed Apr. 7, 2009 Notice of Allowance dated Mar. 7, 2011.
U.S. Appl. No. 12/420,007, filed Apr. 7, 2009 Final Office Action dated Mar. 22, 2013.
U.S. Appl. No. 12/420,007, filed Apr. 7, 2009 Non-Final Office Action dated Oct. 16, 2012.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Final Office Action dated Aug. 2, 2012.

(56) References Cited

OTHER PUBLICATIONS

U.S. Appl. No. 12/617,981, filed Nov. 13, 2009 Advisory Action dated Sep. 15, 2011.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Dec. 21, 2011.
U.S. Appl. No. 12/617,981, filed Nov. 13, 2009 Non-Final Office Action dated Jan. 5, 2011.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 12/917,323, filed Nov. 1, 2010 Advisory Action dated Apr. 10, 2013.
U.S. Appl. No. 12/917,323, filed Nov. 1, 2010 Final Office Action dated Jan. 29, 2011.
C.A. No. 15-218-SLR-SRF, Invalidity Contentions Exhibit A46 dated Jun. 24, 2016.
C.A. No. 15-218-SLR-SRF, Invalidity Contentions Exhibit A47 dated Jun. 24, 2016.
C.A. No. 15-218-SLR-SRF, Invalidity Contentions Exhibit A48 dated Jun. 24, 2016.
C.A. No. 15-218-SLR-SRF, Invalidity Contentions Exhibit A49 dated Jun. 24, 2016.
C.A. No. 15-218-SLR-SRF, Invalidity Contentions Exhibit A5 dated Jun. 24, 2016.
C.A. No. 15-218-SLR-SRF, Invalidity Contentions Exhibit A50 dated Jun. 24, 2016.
C.A. No. 15-218-SLR-SRF, Invalidity Contentions Exhibit A51 dated Jun. 24, 2016.
C.A. No. 15-218-SLR-SRF, Invalidity Contentions Exhibit A6 dated Jun. 24, 2016.
C.A. No. 15-218-SLR-SRF, Invalidity Contentions Exhibit A7 dated Jun. 24, 2016.
C.A. No. 15-218-SLR-SRF, Invalidity Contentions Exhibit A8 dated Jun. 24, 2016.
C.A. No. 15-218-SLR-SRF, Invalidity Contentions Exhibit A9 dated Jun. 24, 2016.
C.A. No. 15-218-SLR-SRF, Invalidity Contentions Exhibit B1 dated Jun. 24, 2016.
C.A. No. 15-218-SLR-SRF, Invalidity Contentions Exhibit B10 dated Jun. 24, 2016.
C.A. No. 15-218-SLR-SRF, Invalidity Contentions Exhibit B11 dated Jun. 24, 2016.
C.A. No. 15-218-SLR-SRF, Invalidity Contentions Exhibit B12 dated Jun. 24, 2016.
C.A. No. 15-218-SLR-SRF, Invalidity Contentions Exhibit B13 dated Jun. 24, 2016.
C.A. No. 15-218-SLR-SRF, Invalidity Contentions Exhibit B14 dated Jun. 24, 2016.
C.A. No. 15-218-SLR-SRF, Invalidity Contentions Exhibit B15 dated Jun. 24, 2016.
C.A. No. 15-218-SLR-SRF, Invalidity Contentions Exhibit B16 dated Jun. 24, 2016.
C.A. No. 15-218-SLR-SRF, Invalidity Contentions Exhibit B17 dated Jun. 24, 2016.
C.A. No. 15-218-SLR-SRF, Invalidity Contentions Exhibit B18 dated Jun. 24, 2016.
C.A. No. 15-218-SLR-SRF, Invalidity Contentions Exhibit B19 dated Jun. 24, 2016.
C.A. No. 15-218-SLR-SRF, Invalidity Contentions Exhibit B2 dated Jun. 24, 2016.
C.A. No. 15-218-SLR-SRF, Invalidity Contentions Exhibit B20 dated Jun. 24, 2016.
C.A. No. 15-218-SLR-SRF, Invalidity Contentions Exhibit B21 dated Jun. 24, 2016.
C.A. No. 15-218-SLR-SRF, Invalidity Contentions Exhibit B22 dated Jun. 24, 2016.
C.A. No. 15-218-SLR-SRF, Invalidity Contentions Exhibit B23 dated Jun. 24, 2016.
C.A. No. 15-218-SLR-SRF, Invalidity Contentions Exhibit B24 dated Jun. 24, 2016.
C.A. No. 15-218-SLR-SRF, Invalidity Contentions Exhibit B25 dated Jun. 24, 2016.
C.A. No. 15-218-SLR-SRF, Invalidity Contentions Exhibit B26 dated Jun. 24, 2016.
C.A. No. 15-218-SLR-SRF, Invalidity Contentions Exhibit B27 dated Jun. 24, 2016.
C.A. No. 15-218-SLR-SRF, Invalidity Contentions Exhibit B28 dated Jun. 24, 2016.
C.A. No. 15-218-SLR-SRF, Invalidity Contentions Exhibit B29 dated Jun. 24, 2016.
C.A. No. 15-218-SLR-SRF, Invalidity Contentions Exhibit B3 dated Jun. 24, 2016.
C.A. No. 15-218-SLR-SRF, Invalidity Contentions Exhibit B30 dated Jun. 24, 2016.
C.A. No. 15-218-SLR-SRF, Invalidity Contentions Exhibit B31 dated Jun. 24, 2016.
C.A. No. 15-218-SLR-SRF, Invalidity Contentions Exhibit B32 dated Jun. 24, 2016.
C.A. No. 15-218-SLR-SRF, Invalidity Contentions Exhibit B33 dated Jun. 24, 2016.
C.A. No. 15-218-SLR-SRF, Invalidity Contentions Exhibit B4 dated Jun. 24, 2016.
C.A. No. 15-218-SLR-SRF, Invalidity Contentions Exhibit B5 dated Jun. 24, 2016.
C.A. No. 15-218-SLR-SRF, Invalidity Contentions Exhibit B6 dated Jun. 24, 2016.
C.A. No. 15-218-SLR-SRF, Invalidity Contentions Exhibit B7 dated Jun. 24, 2016.
C.A. No. 15-218-SLR-SRF, Invalidity Contentions Exhibit B8 dated Jun. 24, 2016.
C.A. No. 15-218-SLR-SRF, Invalidity Contentions Exhibit B9 dated Jun. 24, 2016.
C.A. No. 15-218-SLR-SRF, Invalidity Contentions Exhibit C1 dated Jun. 24, 2016.
C.A. No. 15-218-SLR-SRF, Invalidity Contentions Exhibit C2 dated Jun. 24, 2016.
C.A. No. 15-218-SLR-SRF, Invalidity Contentions Exhibit C3 dated Jun. 24, 2016.
C.A. No. 15-218-SLR-SRF, Invalidity Contentions Exhibit C4 dated Jun. 24, 2016.
C.A. No. 15-218-SLR-SRF, Invalidity Contentions Exhibit C5 dated Jun. 24, 2016.
C.A. No. 15-218-SLR-SRF, Invalidity Contentions Exhibit C6 dated Jun. 24, 2016.
Steinbach, Barbara G., Hardt, N. Sisson, Abbitt, Patricia L, Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
Summers, "A New and Growing family of artificial implanted fluid-control devices" vol. XVI Trans. Amer. Soc. Artif. Int. Organs, 1970.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
Tilford, C. R., "Pressure and Vacuum Measurements"—Ch 2 of Physical Methods of Chemistry pp. 101-173, 1992.
Toray "P-U Celsite Port" brochure—Sep. 1999.
U.S. Department of Health and Human Services, FDA, "Labeling: Regulatory Requirements for Medical Devices" Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.

(56) References Cited

OTHER PUBLICATIONS

Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action dated Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action dated Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.
U.S. Appl. No. 11/368,954, filed Mar. 6, 2006 Non-Final Office Action dated Jul. 21, 2009.
U.S. Appl. No. 11/368,954, filed Mar. 6, 2006 Notice of Allowance dated Jun. 24, 2010.
U.S. Appl. No. 11/368,954, filed Mar., 6, 2006 Final Office Action dated Jan. 27, 2010.
U.S. Appl. No. 11/368,954, filed Mar. 6, 2006 Supplemental Non-final Office Action dated Oct. 2, 2009.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Oct. 20, 2011.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Apr. 7, 2011.
U.S. Appl. No. 11/380,124, filed Apr. 25, 2006 Non-Final Office Action dated Jan. 16, 2009.
U.S. Appl. No. 11/380,124, filed Apr. 25, 2006 Non-Final Office Action dated Oct. 28, 2010.
U.S. Appl. No. 11/380,124, filed Apr. 25, 2006 Notice of Allowance dated Apr. 29, 2013.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Final Office Action dated Mar. 8, 2011.
C.R. Bard, Inc. "Hickman Subcutaneous Ports & Hickman /Broviac Catheters Brochure" Brochure, 1992.
CA 2757836 filed Oct. 5, 2011 Examiner's Report dated May 18, 2016.
Canaud et al. "Dialock: a new vascular access device for extracorporeal renal replacement therapy. Preliminary clinical results" Nephrol. Dial. Transplant 14: 692-698 (1999).
Canaud et al. "Dialock: Pilot Trial of a New Vascular Port Access Device for Hemodialysis" Seminars in Dialysis, vol. 12, No. 5, pp. 382-388 (Sep. 1999).
Canaud et al. "Dialock: Results of french multicentar trial" Nephrology, vol. 22, No. 8, pp. 391-397, (2001).
Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Carlson et al., "Safety Considerations in the Power Injection of Contrast Media Via Central Venous Catheters during Computed Tomographic Examinations," Investigative Radiology, (May 1992) 27: 337-340.
Carlson, J. E. et. al., "Safety Considerations in the Power Injection of Contrast Media Via Central Venous Catheters during Computed Tomographic Examinations" Investigative Radiology, vol. 27, p. 337-340, May 1992.
Center for Devices and Radiological Health, Guidance on 510(k) Submissions for Implanted Infusion Ports, Oct. 1990.
Clinical Plastic Products, "Oncology Jet Port Plus Catheter Systems" Instructions for Use, Oct. 12, 2011.
CN 200980153471.3 filed Jun. 30, 2011 Fifth Office Action dated Jun. 2, 2015.
CN 200980153471.3 filed Jun. 30, 2011 First Office Action dated Dec. 25, 2012.
CN 200980153471.3 filed Jun. 30, 2011 Fourth Office Action dated Nov. 15, 2014.
CN 200980153471.3 filed Jun. 30, 2011 Notice of Grant dated Nov. 5, 2015.
CN 200980153471.3 filed Jun. 30, 2011 Second Office Action dated Sep. 18, 2013.
CN 200980153471.3 filed Jun. 30, 2011 Third Office Action dated May 28, 2014.
CN 201080020088.3 filed Nov. 7, 2011 First Office Action dated Mar. 4, 2013.
CN 201080020088.3 filed Nov. 7, 2011 Second Office Action dated Nov. 21, 2013.
CN 201080051911.7 filed May 16, 2012 First Office Action dated Dec. 27, 2013.
CN 201080051911.7 filed May 16, 2012 Second Office Action dated Jul. 16, 2014.
CN 201080051911.7 filed May 16, 2012 Third Office Action dated Jan. 30, 2015.
CN 201380016157.7 filed Sep. 23, 2014 First office action dated May 16, 2016.
CN 201380016157.7 filed Sep. 23, 2014 Office Action dated Feb. 4, 2017.
CN 201380016157.7 filed Sep. 23, 2014 Office Action dated Jun. 1, 2017.
CN 201410216386.X filed May 21, 2014 First Office Action dated Nov. 2, 2015.

(56) References Cited

OTHER PUBLICATIONS

CN 201410216386.X filed May 21, 2014 Office Action dated Jun. 24, 2016.
CN 201410216386.X filed May 21, 2014 Office Action dated Nov. 29, 2016.
CN 201410216386.X filed May 21, 2014 Search Report dated Nov. 2, 2015.
CN 201510645219.1 filed Nov. 1, 2015 Office Action dated Nov. 16, 2017.
CN 201610037718.7 filed Jan. 20, 2016 Office Action dated Jul. 2, 2018.
CO 14.235.202 filed Oct. 23, 2014 Office Action dated Apr. 25, 2017.
CO 14.235.202 filed Oct. 23, 2014 Office Action dated Nov. 3, 2016.
CO 14.235.202 filed Oct. 23, 2014 Office Action dated Oct. 3, 2017.
Cook Vital-Port® Product Catalog (2000).
Costa, Nancy, "More Than Skin Deep: An Overview of Iodinated Contrast Media . . . " Journal for the Association for Vascular Access, vol. 8, No. 4, 2003.
Costa, Nancy, "Understanding Contrast Media." Journal of Infusion Nursing, vol. 27, No. 5, Sep./Oct. 2004.
Council Directive 93/42/EEC of Jun. 14, 1993 concerning medical devices (Jun. 14, 1993).
Coyle, Douglas et al, Power Injection of Contrast Media via Peripherally Inserted Central Catheters for CT, J Vasc Interv Radiol, pp. 809-814, vol. 15, 2004.
Declaration by Hank LaForce U.S. Pat. No. 7,785,302 (Ref D13 of Request for Trial for Invalidation dated May 22, 2017).
Defendant's Amended Answer to Plaintiffs' First Amended Complaint and Amended Counterclaims dated Sep. 17, 2017.
Deltec Port Systems (Feb. and Apr. 1996).
Department of Health and Human Services, C-Port 510(k) FDA Clearance, Jun. 5, 2003.
Department of Health and Human Services, PowerPort 510(k) FDA Clearance, Jan. 25, 2007.
Desmeules et al. "Venous Access for Chronic Hemodialysis: 'Undesirable Yet Unavoidable'", Artificial Organs 28 (7):611-616 (2004).
Documents attached to P-U Celsite Port (new model first edition to sixth edition) (Ref D10 of Request for Trial for Invalidation dated May 22, 2017).
ECRI Institute, Healthcare Product Comparison System, Dec. 2007.
EP 06 751 411.7 filed Apr. 25, 2006 Office Action dated Sep. 2, 2008.
EP 06737222.7 filed Aug. 17, 2007 Office Action dated Jul. 27, 2016.
EP 06737222.7 filed Aug. 17, 2007 Office Action dated Mar. 9, 2017.
EP 06751411 filed Apr. 25, 2006 Decision of the Technical Board of Appeal dated Jul. 24, 2013.
Levin et al. "Initial results of a new access device for hemodialysis" Kidney International, vol. 54, pp. 1739-1745, (1998).
Levin et al. "New Access Device for Hemodialysis", ASAIO Journal (1998).
LifeSite: Instructions for Implantation & Use for the LifeSite Hemodialysis Access System, 2000.
MedComp "PortCT Technology", display at SIR Conference (Mar. 2006), Toronto, Canada.
Medcomp Dialysis and Vascular Access Products (MEDCOMP) Jun. 30, 2009, Accessed Jun. 29, 2013 http://www.medcompnet.com/products/flipbook/pdf/PN2114G_Medcomp_Catalog_pdf.
Medtronic IsoMed Technical Manual, Model 8472, (2008).
Medtronic IsoMed® Constant-Flow Infusion System: Clinical Reference Guide for Hepatic Arterial Infusion Therapy, Revised Sep. 2000.
MX/a/2011/004499 filed Apr. 28, 2011 First Office Action dated Jul. 25, 2013.
MX/a/2011/004499 filed Apr. 28, 2011 Forth Office Action dated Aug. 3, 2015.
MX/a/2011/004499 filed Apr. 28, 2011 Second Office Action dated May 25, 2014, translation dated Jul. 28, 2014.
MX/a/2011/004499 filed Apr. 28, 2011 Third Office Action dated Jan. 21, 2015.
MX/a/2011/010529 filed Oct. 5, 2011 Office Action dated Apr. 24, 2018.
MX/a/2011/010529 filed Oct. 5, 2011 Office Action dated Jan. 18, 2017.
MX/a/2011/010529 filed Oct. 5, 2011 Office Action dated May 19, 2016.
MX/a/2011/010529 filed Oct. 5, 2011 Office Action dated Oct. 2, 2017.
MX/a/2014/011280 filed Mar. 13, 2013, First Office Action dated May 29, 2015.
MX/a/2014/011280 filed Mar. 13, 2013, Second Office Action dated Oct. 27, 2015.
Navilyst Medical, Implantable Ports with PASV® Valve Technology, Product Overview,<<http://www.navilystmedical.com/Products/index.cfm/9>> last accessed Jun. 4, 2012.
Nebraska Medical Center, Ethanol Lock Technique for Prevention and Treatment of Central Line-Associated Bloodstream Infections, Jul. 2009.
Norfolk Medical Design Dossier/Technical File Vortex, Dec. 1997.
Nucleus Cochlear Implant Systems; User Manual for the ESPrit and ESPrit 22 speech processor and accessories, Issue 3, Apr. 2000.
Nucleus Cochlear Implant Systems; User Manual for the SPrint speech processor and accessories, Issue 4, Apr. 2002.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PCT/US 09/62854 filed Oct. 30, 2009 Written Opinion dated Dec. 23, 2009.
PCT/US06/49007 filed Dec. 21, 2006 Search Report and Written Opinion dated Oct. 1, 2007.
PCT/US2006/008022 filed Mar. 6, 2006 International Preliminary Report on Patentability dated Sep. 12, 2007.
PCT/US2006/008022 filed Mar. 6, 2006 Search Report dated Jul. 5, 2006.
PCT/US2006/008022 filed Mar. 6, 2006 Written Opinion dated Apr. 9, 2007.
PCT/US2006/008022 filed Mar. 6, 2006 Written Opinion dated Jul. 5, 2006.
PCT/US2006/015695 filed Apr. 25, 2006 Partial Search Report dated Sep. 29, 2006.
PCT/US2006/015695 filed Apr. 25, 2006 Search Report dated Jan. 11, 2007.
PCT/US2006/015695 filed Apr. 25, 2006 Written Opinion dated Jan. 11, 2007.
PCT/US2006/016056 filed Apr. 27, 2006 International Preliminary Report on Patentability dated Oct. 30, 2007.
PCT/US2006/016056 filed Apr. 27, 2006 Search Report dated Sep. 20, 2006.
PCT/US2006/016056 filed Apr. 27, 2006 Written Opinion dated Oct. 27, 2007.
PCT/US2006/016056 filed Apr. 27, 2006 Written Opinion dated Sep. 20, 2006.
PCT/US2006/049007 filed Dec. 21, 2006 International Preliminary Report on Patentability dated Jul. 1, 2008.
PCT/US2006/049007 filed Dec. 21, 2006 Written Opinion dated Oct. 1, 2007.
PCT/US2007/006776 filed Mar. 19, 2007 International Preliminary Report on Patentability dated Jan. 2, 2009.
PCT/US2007/006776 filed Mar. 19, 2007 International Search Report dated Dec. 18, 2007.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Sep. 23, 2008.
PCT/US2007/011015 filed May 7, 2007 Search Report dated Jun. 10, 2008.
PCT/US2007/011456 filed May 11, 2007 Search Report dated Aug. 28, 2008.

(56) References Cited

OTHER PUBLICATIONS

PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
"Japanese Journal of Cancer and Chemotherapy", 26, (13), 2055-2060, issued on Nov. 16, 1999. (Ref D18 of Request for Trial for Invalidation dated May 22, 2017).
"Rad Fan", 1, (3), 40-43, issued on Jul. 25, 2003 (Ref D17 of Request for Trial for Invalidation dated May 22, 2017).
"Safety Considerations in the Power Injection of Contrast Medium via a Totally Implantable Central Venous Access System" IVR Interventional Radiology, 20, (1) 27-30, issued on Jan. 1, 2005. (Ref D09 of Request for Trial for Invalidation dated May 22, 2017).
Allergan, Inc. Lap-Band® System Fact Sheet. © 2007.
Angiodynamics's Answer to Supplemental Complaint, Counterclaims Against Bard Peripheral Vascular, and Cross Claims/Third Party Complaint Against C.R. Bard. Public Version, dated Aug. 18, 2017.
AngioDynamics, Smart Port Guidelines for Health Care Providers, 2010.
Appendix B of Invalidity Contention Charts dated Nov. 28, 2017.
AU 2013235532 filed Aug. 6, 2014 Office Action dated Sep. 6, 2017.
B. Braun, Access Port Systems, Celsite® Product Information, 19 pages, Nov. 2005.
B. Braun, Easypump Product Page, accessed May 11, 2011.
B. Braun, Port Catheter Systems Product Page, accessed May 11, 2011.
Bard Access Systems Mar. 21, 1995 Product Release to Market form for "M.R.I. Port with 8 Fr. ChronoFlexO Catheter", "M.R.I. Port with 8Fr. ChronoFlex Catheter with Intro-Eze™ ", "M.R.I. Port with 8. Fr ChronoFlex Catheter and Peel Apart", "M.R.I. Port with 8Fr. ChronoFlex Catheter Demo Kit". Drawings included.
Bard Access Systems, BardPort and X-Port Implanted Ports Brochure, © 2007.
Bard Access Systems, BardPort, SlimPort and X-Port Instructions for Use, May 2003.
Bard Access Systems, BardPort, SlimPort, X-Port Instructions for Use, 24 pages, Oct. 2012.
Bard Access Systems, BardPort™ Implanted Ports Patient Information, Feb. 1993.
Bard Access Systems, Devices for Small Patients, 4 pages, Jul. 1992.
Bard Access Systems, Family of PICCs, 1 page, Mar. 10, 2006.
Bard Access Systems, M.R.I. Dual Port with Septum-Finder Ridge IFU, 2 pages, © 1993.
Bard Access Systems, Ports Brochure, © 2003.
Bard Access Systems, PowerPort and PowerLoc CT Guide, 11 pages, Dec. 2009.
Bard Access Systems, PowerPort and PowerLoc Product Brochure, 6 pages, © 2007.
Bard Access Systems, PowerPort CT Guide, 16 pages, Mar. 2007.
Bard Access Systems, PowerPort Guidelines for CT Technologists, 1 page, Feb. 2007.
Bard Access Systems, PowerPort Guidelines for CT Technologists, 1 page, Jul. 2006.
Bard Access Systems, PowerPort Guidelines for Nurses, 1 page, Feb. 2007.
Bard Access Systems, PowerPort Guidelines for Physicians, 1 page, Feb. 2007.
Bard Access Systems, PowerPort Implanted Port with Open-Ended Catheter Instructions 2006. for Use, 8 pages, Dec. 2006.
Bard Access Systems, PowerPort Information for the Patient, 5 pages, © 2006.
Bard Access Systems, PowerPort Prescription Pad, 1 p., © 2007.
Bard Access Systems, PowerPort Product Brochure, 8 pp., ©2009.
Bard Access Systems, PowerPod Implantable Port Product Information, © 2007.
Bard Access Systems, Titanium Dome Implantable Port, http://www.bardacess.com, last accessed Jan. 10, 2012.
Bard Access Systems, When in Doubt, SCOUT!, 1 page, © 2007.
Bard Healthcare Leaflet (2001).
BardPort, SlimPort, X-Port Instructions for Use, 2012.
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Beathard et al. "Initial clinical results with the LifeSite Hemodialysis Access System" Kidney International, vol. 58, pp. 2221-2227, (2000).
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.
BioEnterics Corporation, Lap-Band® "Adjustable Gastric Banding System" Product Brochure Rev. G, Nov. 2000.
Biolink: Products—Dialock System (2002).
Biotronik, Stratos Cardiac Resynchronization Therapy Pacemakers Technical Manual, 179 pages, © 2008.
Boston Scientific, Xcela™ Power Injectable PICC Directions for Use, 12 pages, © 2007.
Braun Product Catalog (Aug. 2005).
CA 2,864,047 filed Aug. 6, 2014 Office Action dated Apr. 23, 2019.
CN 201610037718.7 filed Jan. 20, 2016 Office Action dated Mar. 1, 2019.
EP 09824195.3 filed Apr. 13, 2011 Office Action dated Apr. 10, 2019.
EP 13764254.2 filed Sep. 10, 2014 Office Action dated Mar. 25, 2019.
EP 18155508.7 filed Oct. 5, 2011 Partial European Search Report dated Nov. 6, 2018.
U.S. Appl. No. 14/508,227, filed Oct. 7, 2014 Notice of Allowance dated Feb. 4, 2019.
U.S. Appl. No. 14/599,376, filed Jan. 16, 2015 Notice of Allowance dated Nov. 6, 2018.
U.S. Appl. No. 15/290,621, filed Oct. 11, 2016 Notice of Allowance dated Dec. 13, 2018.
U.S. Appl. No. 16/029,103, filed Jul. 6, 2018 Notice of Allowance dated Sep. 4, 2018.
Buerger et al "Implantation of a new device for haemodialysis" Nephrol. Dial. Transplant 15: 722-724 (2000).
*C. R. Bard, Inc. and Bard Peripheral Vascular, Inc., v. Angiodynamics, Inc.*, C.A. No. 15-218-JFB-SRF, Angiodynamics's Answer to Supplemental Complaint, Counterclaims Against Bard Peripheral Vascular, and Crossclaims/Third Party Complaint Against C.R. Bard public version dated Aug. 25, 2017. [Redacted].
*C. R. Bard, Inc. and Bard Peripheral Vascular, Inc., v. Angiodynamics, Inc.*, C.A. No. 15-218-SLR-SRF, Angiodynamics, Inc.'s Initial Invalidity Contentions dated Jun. 24, 2016.
*C. R. Bard, Inc. and Bard Peripheral Vascular, Inc., v. Angiodynamics, Inc.*, C.A. No. 15-218-SLR-SRF, Defendant and Counterclaim-Plaintiff Angiodynamics's Identification of Invalidity References dated Mar. 15, 2017.
*C. R. Bard, Inc. and Bard Peripheral Vascular, Inc., v. Angiodynamics, Inc.*, C.A. No. 15-218-SLR-SRF, Expert Report of Timothy Clark, MD, MD, FSIR Regarding Infringement of the Patents-In-Suit dated Nov. 30, 2017. [Redacted].
*C. R. Bard, Inc. and Bard Peripheral Vascular, Inc., v. Angiodynamics, Inc.*, C.A. No. 1:15-cv-00218-JFB-SRF, Opening Expert Report

(56) References Cited

OTHER PUBLICATIONS of Robert L. Vogelzang, M.D. Regarding Invalidity of U.S. Pat. No. 8,475,417, 8,545,460 & 8,805,478 dated Sep. 1, 2017. [Redacted].
C. R. Bard, Inc. and Bard Peripheral Vascular, Inc., v. Medical Components, Inc., C.A. No. 2:17-cv-00754-TS, Defendant's Initial Noninfringement, Unenforceability, and Invalidity Contentions dated Nov. 28, 2017.
C. R. Bard, Inc. and Bard Peripheral Vascular, Inc., v. Medical Components, Inc., C.A. No. 2:17-cv-00754-TS, Defendant's Second Amended Answer to Plaintiffs' First Amended Complaint and Second Amended Counterclaims dated Nov. 7, 2017.
C. R. Bard, Inc. and Bard Peripheral Vascular, Inc., v. Medical Components, Inc., C.A. No. 2:17-cv-00754-TS, Plaintiffs' Motion to Dismiss Medcomp's Inequitable Conduct Counterclaims and to Strike Medcomp's Inequitable Conduct Affirmative Defenses dated Oct. 16, 2017.
C. R. Bard, Inc. v Innovative Medical Devices, LLC; Medical Components, Inc. "Petition for Inter Partes Review of U.S. Pat. No. 8,852,160" dated Jul. 31, 2015.
C.A. No. 15-218-SLR-SRF, Invalidity Contentions Exhibit A1 dated Jun. 24, 2016.
C.A. No. 15-218-SLR-SRF, Invalidity Contentions Exhibit A10 dated Jun. 24, 2016.
C.A. No. 15-218-SLR-SRF, Invalidity Contentions Exhibit A11 dated Jun. 24, 2016.
C.A. No. 15-218-SLR-SRF, Invalidity Contentions Exhibit A12 dated Jun. 24, 2016.
C.A. No. 15-218-SLR-SRF, Invalidity Contentions Exhibit A13 dated Jun. 24, 2016.
C.A. No. 15-218-SLR-SRF, Invalidity Contentions Exhibit A14 dated Jun. 24, 2016.
C.A. No. 15-218-SLR-SRF, Invalidity Contentions Exhibit A15 dated Jun. 24, 2016.
C.A. No. 15-218-SLR-SRF, Invalidity Contentions Exhibit A16 dated Jun. 24, 2016.
C.A. No. 15-218-SLR-SRF, Invalidity Contentions Exhibit A17 dated Jun. 24, 2016.
C.A. No. 15-218-SLR-SRF, Invalidity Contentions Exhibit A18 dated Jun. 24, 2016.
C.A. No. 15-218-SLR-SRF, Invalidity Contentions Exhibit A19 dated Jun. 24, 2016.
C.A. No. 15-218-SLR-SRF, Invalidity Contentions Exhibit A2 dated Jun. 24, 2016.
C.A. No. 15-218-SLR-SRF, Invalidity Contentions Exhibit A20 dated Jun. 24, 2016.
C.A. No. 15-218-SLR-SRF, Invalidity Contentions Exhibit A21 dated Jun. 24, 2016.
C.A. No. 15-218-SLR-SRF, Invalidity Contentions Exhibit A22 dated Jun. 24, 2016.
C.A. No. 15-218-SLR-SRF, Invalidity Contentions Exhibit A23 dated Jun. 24, 2016.
C.A. No. 15-218-SLR-SRF, Invalidity Contentions Exhibit A24 dated Jun. 24, 2016.
C.A. No. 15-218-SLR-SRF, Invalidity Contentions Exhibit A25 dated Jun. 24, 2016.
C.A. No. 15-218-SLR-SRF, Invalidity Contentions Exhibit A26 dated Jun. 24, 2016.
C.A. No. 15-218-SLR-SRF, Invalidity Contentions Exhibit A27 dated Jun. 24, 2016.
C.A. No. 15-218-SLR-SRF, Invalidity Contentions Exhibit A28 dated Jun. 24, 2016.
C.A. No. 15-218-SLR-SRF, Invalidity Contentions Exhibit A29 dated Jun. 24, 2016.
C.A. No. 15-218-SLR-SRF, Invalidity Contentions Exhibit A3 dated Jun. 24, 2016.
C.A. No. 15-218-SLR-SRF, Invalidity Contentions Exhibit A30 dated Jun. 24, 2016.
C.A. No. 15-218-SLR-SRF, Invalidity Contentions Exhibit A31 dated Jun. 24, 2016.
C.A. No. 15-218-SLR-SRF, Invalidity Contentions Exhibit A32 dated Jun. 24, 2016.
C.A. No. 15-218-SLR-SRF, Invalidity Contentions Exhibit A33 dated Jun. 24, 2016.
C.A. No. 15-218-SLR-SRF, Invalidity Contentions Exhibit A34 dated Jun. 24, 2016.
C.A. No. 15-218-SLR-SRF, Invalidity Contentions Exhibit A35 dated Jun. 24, 2016.
C.A. No. 15-218-SLR-SRF, Invalidity Contentions Exhibit A36 dated Jun. 24, 2016.
C.A. No. 15-218-SLR-SRF, Invalidity Contentions Exhibit A37 dated Jun. 24, 2016.
C.A. No. 15-218-SLR-SRF, Invalidity Contentions Exhibit A38 dated Jun. 24, 2016.
C.A. No. 15-218-SLR-SRF, Invalidity Contentions Exhibit A39 dated Jun. 24, 2016.
C.A. No. 15-218-SLR-SRF, Invalidity Contentions Exhibit A4 dated Jun. 24, 2016.
C.A. No. 15-218-SLR-SRF, Invalidity Contentions Exhibit A40 dated Jun. 24, 2016.
C.A. No. 15-218-SLR-SRF, Invalidity Contentions Exhibit A41 dated Jun. 24, 2016.
C.A. No. 15-218-SLR-SRF, Invalidity Contentions Exhibit A42 dated Jun. 24, 2016.
C.A. No. 15-218-SLR-SRF, Invalidity Contentions Exhibit A43 dated Jun. 24, 2016.
C.A. No. 15-218-SLR-SRF, Invalidity Contentions Exhibit A44 dated Jun. 24, 2016.
C.A. No. 15-218-SLR-SRF, Invalidity Contentions Exhibit A45 dated Jun. 24, 2016.
PCT/US2008/067679 filed Jun. 20, 2008 Search Report dated Sep. 30, 2008.
PCT/US2008/067679 filed Jun. 20, 2008 Written Opinion dated Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report dated Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/035088 filed Feb. 25, 2009 International Search Report dated May 19, 2009.
PCT/US2009/035088 filed Feb. 25, 2009 Written Opinion dated May 19, 2009.
PCT/US2009/062854 filed Oct. 30, 2009 International Preliminary Report on Patentability dated May 5, 2011.
PCT/US2009/062854 filed Oct. 30, 2009 International Search Report dated Dec. 23, 2009.
PCT/US2009/062854 filed Oct. 30, 2009 Search Report dated Dec. 23, 2009.
PCT/US2009/062854 filed Oct. 30, 2009 Written Opinion dated Dec. 23, 2009.
PCT/US2010/030256 filed Apr. 7, 2010 Search Report dated Jun. 4, 2010.
PCT/US2010/030256 filed Apr. 7, 2010 Written Opinion dated Jun. 4, 2010.
PCT/US2010/054994 filed Nov. 1, 2010 Search Report dated Jan. 10, 2011.
PCT/US2010/054994 filed Nov. 1, 2010 Written Opinion dated Jan. 10, 2011.
PCT/US2011/037038 filed May 18, 2011 International Preliminary Report on Patentability dated Nov. 20, 2012.
PCT/US2011/037038 filed May 18, 2011 International Search Report and Written Opinion dated Aug. 30, 201t.
PCT/US2011/037038 filed May 18, 2011 Written Opinion and Search Report dated Aug. 30, 2011.
PCT/US2013/031035 filed Mar. 13, 2013 International Search Report and Written Opinion dated Jun. 3, 2013.

(56) References Cited

OTHER PUBLICATIONS

PCT/US2013/056019 filed Aug. 21, 2013 International Search Report and Written Opinion dated Feb. 28, 2014.
PCT/US99/28695 filed Dec. 3, 1999 International Preliminary Examination Report dated Apr. 21, 2001.
PCT/US99/28695 filed Dec. 3, 1999 Search Report dated Apr. 11, 2000.
PFM Medical, Xcela™ Power Injectable Port Directions for Use, 15 pages, © 2008.
Picture of HMP Vortex MP Vascular Access Port from Exhibit A11, Jun. 24, 2016.
Port-A-Cath Implantable Vascular Access Systems, brochure, (1996).
Port-A-Cath® P.A.S. Port® Systems by Deltec, Product Specifications, 1999.
Port-A-Cath® "Implantable Epidural, Aterial and Peritonial Access Systems" Internet Product Listing. <<http://web.archive.org/web/20001119035900/www.deltec.com/cPacspl.htm.>> last accessed Jun. 4, 2012.
Port-A-Cath® "Many Port-A-Cath® System Choices" Product Brochure. © 1996 SIMS Deltec, Inc.
Port-A-Cath® & Port-A-Cath® II Dual-lumen Implantable Venous Access Systems Product Specifications, 2005.
Port-A-Cath® II Implantable Access Systems Information Sheet, Sep. 2006.
Proper Care of the Vortex, Nov. 30, 2000.
Rappolt, Richard T., et al. "Radiopaque Codification and X-ray Identification of Ingested Drugs." Ingestive Radiology, May-Jun. 1966.
Request for Inter partes Reexamination of U.S. Pat. No. 7,785,302, filed Aug. 20, 2012.
Request for Inter partes Reexamination of U.S. Pat. No. 7,947,022, filed Aug. 20, 2012.
Request for Inter partes Reexamination of U.S. Pat. No. 7,959,615, filed Aug. 20, 2012.
RU 2014140544 filed Mar. 13, 2016 Office Action dated Jul. 20, 2017.
Salis et al., "Maximal flow rates possible during power injection through currently available PICCs: An in-vitro study," J Vasc Interv Radiol 2004; 15:275-281.
Sandstede, Joern, "Pediatric CT," available online at www.multislice-ct.com, MultiSLICE-CT.com, version 02, May 2, 2003.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith Medical, Port-A-Cath® "Single-lumen Implantable Vascular Access Systems" Product Specifications, 2004.
Smith, Lisa Hartkoph, "Implanted Ports, Computed Tomography, Power Injectors, and Catheter Rupture." Clinical Journal of Oncology Nursing, vol. 12, No. 5. Oct. 2008.
Smiths Medical, "Smiths Medical Launches Implantable Ports for Easy Viewing Under CT Scans" Press Release, Jan 5, 2011.
Soloman, et al., "CIN Strategies: Anticipate, Manage, Prevent." Supplement to Imaging Economics, May 2007.
Statement of Prof. Dr. med. Karl R. Aigner, Oct. 11, 2011.
U.S. Appl. No. 14/104,354, filed Dec. 12, 2013 Non-Final Office Action dated Sep. 4, 2019.
U.S. Appl. No. 15/594,288, filed May 12, 2017 Non-Final Office Action dated Aug. 21, 2019.
U.S. Appl. No. 16/153,488, filed Oct. 5, 2018 Notice of Allowance dated Sep. 18, 2019.

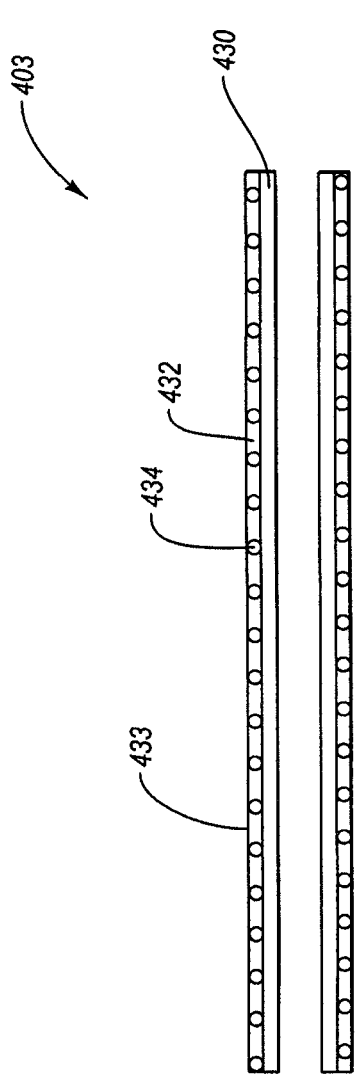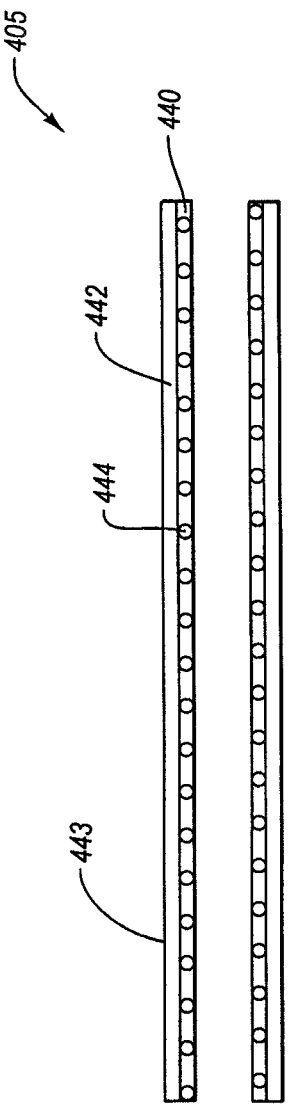
FIG. 40
FIG. 41

ASSEMBLIES FOR IDENTIFYING A POWER INJECTABLE ACCESS PORT

CROSS-REFERENCE TO RELATED APPLICATIONS

This application is a continuation of U.S. patent application Ser. No. 14/171,364, filed Feb. 3, 2014, now U.S. Pat. No. 10,052,470, which is a continuation of U.S. patent application Ser. No. 13/886,201, filed May 2, 2013, now U.S. Pat. No. 8,641,688, which is a continuation of U.S. patent application Ser. No. 12/420,007, filed Apr. 7, 2009, now U.S. Pat. No. 8,475,417, which is a continuation of U.S. patent application Ser. No. 11/380,124, filed Apr. 25, 2006, now U.S. Pat. No. 8,545,460, which claims the priority benefit of U.S. Provisional Application No. 60/737,466, filed Nov. 15, 2005, and of U.S. Provisional Application No. 60/675,309, filed Apr. 27, 2005, each of which applications is hereby incorporated by reference in its entirety into this application.

BACKGROUND

A wide variety of medical procedures require infusion of a fluid into a patient. For example, vascular imaging technologies may require use of a contrast media that is injected into the patient. More specifically, computed tomography (CT) is an imaging technology that utilizes a contrast media and may be employed for the noninvasive evaluation and assessment of a vascular system (i.e., CT angiography or CTA). Multidetector computed tomography (MDCT) is one specific type of CT that may be utilized for CTA. For proper imaging of a vascular system via CT, intravenous contrast media injection protocols are coordinated and selected for the anatomic area of interest.

More particularly, conventionally, a so-called "power injector" system may be employed for injecting contrast media at a high pressure into a peripherally inserted intravenous (IV) line. For example, such power injectors or injection systems may be commercially available from Medrad, Inc., a subsidiary of Schering AG, Germany and may be marketed as STELLANT® injection systems. Because CT procedures are often defined in terms of a desired flow rate of contrast media, such power injection systems are, in general, controllable by selecting a desired flow rate. Accordingly, such power injection systems may develop pressure (within the maximum pressure capability of the power injection system) as is necessary to maintain the selected flow rate. Accordingly, as may be appreciated, obstructions in the IV lines or use of IV lines that are not structured to withstand the pressures of a desired injection rate may cause the power injector to generate a pressure that exceeds a suitable pressure limit for the IV line. After intravenous injection, a bolus of contrast material, may flow within the vascular system of the patient to the right side of the heart, through the lungs, into the left side of the heart, and through the remaining circulatory system. After the bolus of contrast media is injected into the patient, portions of the contrast media may remain in the right side of the heart. Thus, the overall effectiveness of contrast enhancement may depend on a multitude of factors. For example, a patient's characteristics (e.g., body size; circulation, including cardiac output and circulating volume, and renal function), the contrast characteristics (e.g., volume, injection rate, iodine concentration, etc.), and the CT technique (e.g., access and route of administration, scan delay, scan speed, and injection pattern) may each influence the overall degree of contrast enhancement.

By way of background, conventionally, relatively long scan times have been accompanied by relatively long contrast media delivery times. However, because scan times continue to decrease, relatively fast delivery of contrast media may be desired. Explaining further, in coronary CTA, a large enough volume of contrast material must be administered at a sufficiently high rate to reach and maintain a suitable concentration throughout a selected scan time (e.g., a 15 second scan time), and within a selected region of the anatomy (e.g., an axial scan distance of 20 cm, which may include the left ventricle and outflow tract). It also may be desirable that contrast density values are sufficient to facilitate the segmentation techniques used in multidimensional post-processing. A typical contrast media used in coronary CTA may have an iodine density of about 300 milligrams per milliliter to about 350 milligrams per milliliter. Also, since contrast media may be radioactive, reducing the overall quantity of contrast media required to perform an imaging process may be advantageous.

The pressure required for contrast injection depends on many factors, including flow rate, contrast viscosity, configuration of infusion tubing, such as tube diameter and length, and any obstruction or restriction to flow (e.g., kinks, curves, fittings, compression). As mentioned above, to maintain the flow rate required for a CT or MRI study, a power injector may generate high pressures. Ruptures can occur when the injection pressure exceeds the tolerance of the vascular access device(s). Other problems may occur due to timing errors between the scan and the contrast. In order to maximize the rapid scanning capacity of the newer vascular imaging devices, the starting of the scanning process can be delayed a predetermined amount of time after injection of the contrast media has begun. If the scan starts too early, just as the contrast is arriving at the heart, arteries can appear smaller than they really are when the image is post-processed. On the other hand, if scanning is delayed too long, image artifacts can arise from diluted contrast in the cardiac veins. The window of opportunity for optimal scans may be very small, because contrast media circulates quickly through cardiac arteries and into cardiac veins.

Some diagnostic or medical procedures may advantageously employ a subcutaneous vascular access port for introducing a fluid into the vasculature of a patient. Access portals, or ports, provide a convenient method to repeatedly deliver medicants to remote areas of the body without utilizing surgical procedures. The port is implantable within the body, and permits the infusion of medications, parenteral solutions, blood products, contrast media, or other fluids. Additionally, the port may be used to aspirate blood from the patient. Such access ports typically include a cannula-impenetrable housing which encloses one or more fluid cavities or reservoirs and defines for each such fluid cavity an access aperture communicating through the housing. A cannula-penetrable septum is positioned adjacent to and seals each access aperture. An outlet stem communicates with one or more of the fluid cavities for dispensing medication therefrom to a predetermined location in the body of the patient through an implanted catheter attached to the access port. Once the access port and the catheter have been implanted beneath the skin of a patient, quantities of fluid, such as medication, blood, etc., may be dispensed through one such fluid cavity by, for example, a cannula (e.g., a needle), passed through the skin of the patient and penetrating the septum into one of the respective fluid cavities. This medication is directed through the distal end of the catheter to an entry point into the venous system of the body of the patient. Further, blood may be aspirated through the subcutaneous access port. Thus, use of an access port may allow for vascular access without needle sticks into the vasculature of a patient.

However, conventional access ports and attendant infusion systems have not been suitable for performing power injection.

Particularly, the use of power injection systems in combination with conventional vascular access ports has achieved less than ideal results. Thus, it may be appreciated that vascular access ports for infusion systems and infusion-related apparatuses structured for performing power injection may be advantageous.

SUMMARY

One aspect of the instant disclosure relates to a method of flowing fluid through an access port. More particularly, a vascular access port may be provided and a fluid may be caused to flow through the access port at a rate of at least about 1 milliliter per second.

A further aspect of the instant disclosure relates to a method of flowing fluid through an infusion set. For example, an infusion set may be provided and a fluid may be flowed through the infusion set at a rate of at least about 1 milliliter per second.

Another aspect of the instant disclosure relates to an access port for providing subcutaneous access to a patient. Specifically, an access port may comprise a housing defining an aperture for capturing a septum, wherein the housing and septum define a reservoir. In addition, the septum may include a tenon region wherein the housing of the access port defines a complimentary mortise region structured for accepting at least a portion of the tenon region of the septum. Optionally, the housing may include a ring structure proximate to at least a portion of a side periphery of the septum.

An additional aspect of the instant disclosure relates to an access port for providing subcutaneous access to a patient. In one embodiment, an access port may comprise a housing defining an aperture for capturing a septum, the housing and septum defining a reservoir. In addition, the housing and septum may be structured for accommodating a flow rate through the reservoir of at least about 1 milliliter per second. In another embodiment, an access port may include a housing and septum, as described above, wherein the housing and the septum are structured for accommodating a pressure developed within the reservoir of at least about 35 psi.

Yet another aspect of the instant disclosure relates to an infusion set for use in subcutaneously accessing a patient. For example, in one embodiment, an infusion set may comprise a tubing section defining a lumen and a cannula in fluid communication with the lumen of the tubing section. Also, the cannula may be configured for insertion through a septum of an access port, and the tubing section and the cannula may be structured for allowing a fluid to flow at a rate of at least about 1 milliliter per second. Optionally the cannula may be configured for puncturing a septum of an access port and the tubing section and the cannula may be structured for accommodating a pressure of at least about 400 psi. For example, the tubing section and the cannula may be structured for accommodating a pressure of about 600 psi.

A further aspect of the instant disclosure relates to infusion tubing for use in accessing a vascular system of a patient. In one embodiment, infusion tubing may comprise a plurality of layers, wherein the tubing is structured for accommodating a fluid flow rate of at least about 1 milliliter per second. In another embodiment, infusion tubing may comprise a plurality of layers, wherein at least one layer of the plurality of layers extends beyond at least another of the plurality of layers and is structured for forming a cannula for puncturing a septum of an access port. In yet an additional embodiment, an infusion set for use in subcutaneously accessing a patient may comprise a tubing section defining a lumen and a cannula in fluid communication with the lumen of the tubing section, wherein the cannula is configured for insertion through a septum of an access port. Additionally, the tubing section and cannula may be structured for accommodating a pressure of at least about 400 psi.

Another aspect of the instant disclosure relates to a method of identifying an access port as being suitable for power injection. More specifically, an access port including a septum may be provided. Further, the access port may be identified as being suitable for power injection.

Yet a further aspect of the instant disclosure relates to an access port for providing subcutaneous access to a patient. Particularly, an access port may comprise a housing configured for capturing a septum, the septum configured for inserting a cannula therethrough and into a reservoir defined within the housing and at least one structural element configured for resisting deformation of the septum in response to a pressure developed within the reservoir.

In an additional aspect of the instant disclosure, a method of operation of an access port may comprise providing a housing configured for capturing a septum, the septum configured for inserting a cannula (which can include a needle, a Huber needle, a trocar with an associated cannula, or any combination thereof) therethrough and into a reservoir defined within the housing, and developing a pressure within the reservoir of the housing. Further, such a method may comprise limiting deformation of the septum in response to the pressure developed within the reservoir.

In addition, one aspect of the instant disclosure relates to a septum comprising a gel or a viscous liquid. For example, in one embodiment, a septum for assembly with a housing to form an access port for providing subcutaneous access to a patient may comprise a body including an upper surface and a lower surface and at least one gel region positioned generally between the upper surface and the lower surface. Another embodiment may comprise a septum for assembly with a housing to form an access port for providing subcutaneous access to a patient may comprise a body, a layer formed over at least a portion of the body, and a gel region positioned at least partially between the layer and the body.

The above-described infusion apparatuses and related methods may be beneficially employed for effecting or facilitating power injection processes. For instance, such methods and apparatuses may be employed for infusing a fluid (e.g., a contrast media) at a rate of between about 1 milliliter per second and about 5 milliliters per second.

Features from any of the above mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Advantages of the instant disclosure will become apparent upon review of the following detailed description and drawings, which illustrate representations (not necessarily drawn to scale) of various aspects of the instant disclosure, wherein:

FIG. 40 shows a schematic, side cross-sectional view of tubing including an inner layer, an outer layer, and at least one reinforcing element;

FIG. 41 shows a schematic, side cross-sectional view of another embodiment of tubing including an inner layer, an outer layer, and at least one reinforcing element;

DETAILED DESCRIPTION

One aspect of the instant disclosure relates to vascular access ports. More particularly, in one embodiment, the instant disclosure contemplates that a vascular access port may be structured for accommodating a fluid flow rate of at least about 1 milliliter per second. Further, the instant disclosure contemplates that a vascular access port may be structured to withstand at least about 180 pounds per square inch (psi) of pressure developed within the reservoir defined by the septum and the access port housing. In one embodiment, an access port may be structured for operating within a range of pressures of about 80 psi to about 180 psi. Such an access port may be advantageous for use in infusing a fluid into a patient (e.g., infusing contrast media into a patient for CT or MR imaging).

Generally, an access port may comprise a housing that captures a septum that may be repeatedly pierced or punctured with a hollow slender element (e.g., a cannula, or needle), which can include a Huber needle, a trocar with a circumferentially disposed cannula, or any other suitable access mechanism, without limitation. The words "cannula" or "needle," as used herein, encompass any slender element (e.g., a cannula, a needle, a trocar, with a circumferentially disposed cannula, etc.) as known in the art or described herein, without limitation. Such a septum may comprise a material (e.g., silicone) that seals, under suitable compression, passages formed by puncturing the septum with such an access mechanism. Thus, the septum may be at least partially compressed to facilitate closure of passages formed by puncturing the septum with the access mechanism. The instant disclosure contemplates that the housing and septum may be structured so that a flow rate from the reservoir of the access port may be at least about 1 milliliter per second without damaging the housing or septum or compromising the structural integrity of the reservoir (e.g., causing the septum to become separated from the housing).

Figure 1:
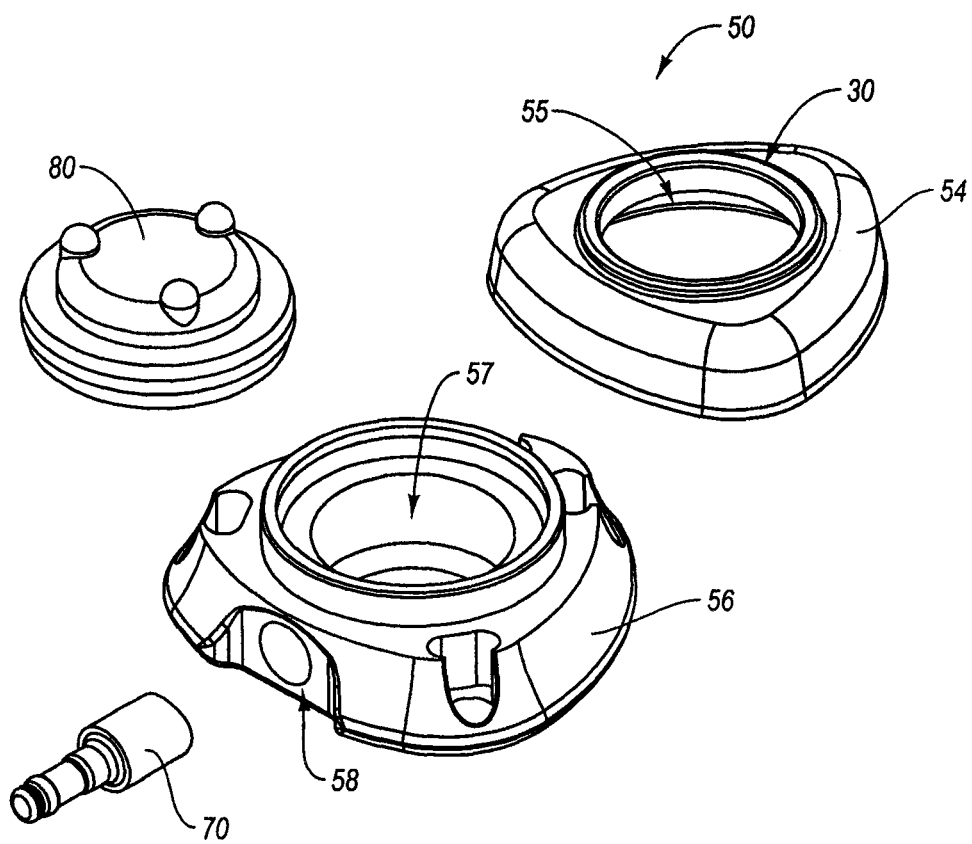
FIG. 1 shows an exploded, perspective view of an access port according to the instant disclosure.
Figure 2:
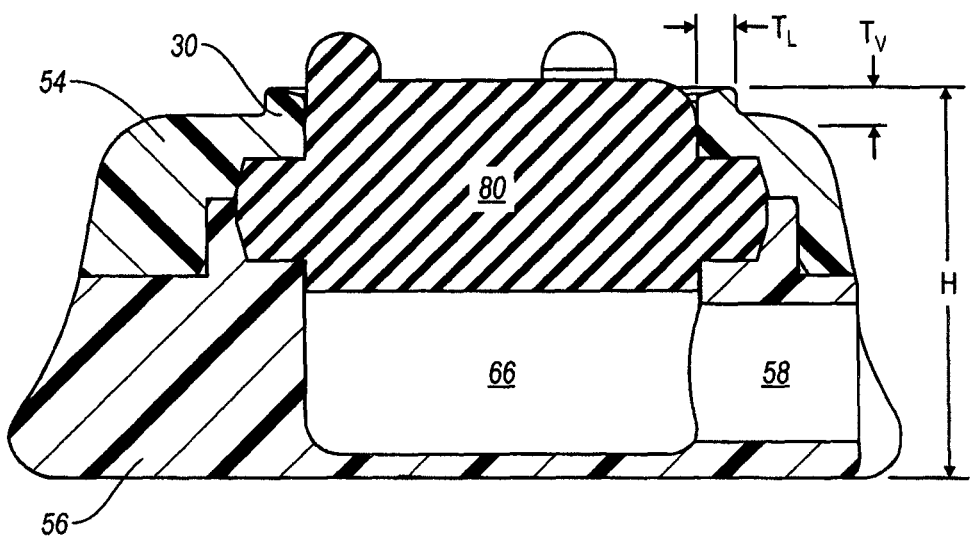
FIG. 2 shows a schematic, side cross-sectional view of the access port shown in FIG. 1.

In one embodiment, an access port may comprise a cap and base which define, in combination, a housing in which a septum may be positioned to form a reservoir. For example, FIGS. 1 and 2 show, respectively, an exploded perspective view and a side cross-sectional view of an access port 50 including a base 56, a cap 54, a septum 80, and an outlet stem 70. As shown in FIGS. 1 and 2, cap 54 and base 56, may be configured for capturing a septum 80 between cap 54 and 56. Generally, cap 54 and base 56 may collectively form a housing 60 for capturing septum 80 and at least partially defining reservoir 66. Explaining further, cap 54 may include an aperture 55 through which a portion of septum 80 may extend and base 56 may include a recess 57 configured to accept at least a portion of septum 80. Thus, a portion of septum 80 may be placed within recess 57 of base 56 and aperture 55 of cap 54 may be positioned about septum 80 to collectively define a reservoir 66 within access port 50, the reservoir 66 being in fluid communication with a lumen of outlet stem 70. In other embodiments, a plurality of reservoirs may be collectively defined by a housing and at least one septum, without limitation. For example, any access port known in the art including a plurality of reservoirs (or one reservoir) may include any aspects) of the instant disclosure, without limitation. As shown in FIG. 1, a portion of outlet stem 70 may be positioned within and coupled to an aperture 58 formed within base 56.

Although FIG. 1 shows that access port 50 may include an outlet stem 70, other embodiments of access port 50 may not include an outlet stem 70. Therefore, FIG. 2 shows access port 50 without an outlet stem 70. Put another way, the instant disclosure contemplates that access port 50 may, optionally, include an outlet stem 70 or may be otherwise configured. For instance, in one embodiment, outlet stem 70 may be formed as a part of with base 56, if desired. In another embodiment, a catheter may be operably coupled to the access port 50 (e.g., to aperture 58) without outlet stem 70. In yet a further embodiment, access port 50 may simply include at least one outlet passage (e.g., aperture 58) in fluid communication with the reservoir 66 and extending through the housing 60 and structured for allowing fluid flow through, if desired. As shown in FIG. 2, a portion of septum 80 may be positioned between cap 54 and base 56 and may be configured to withstand, without damage or deforming to an extent that compromises the reservoir 66 (i.e., blowing out), a selected magnitude of pressure developed within reservoir 66.

Figure 3:
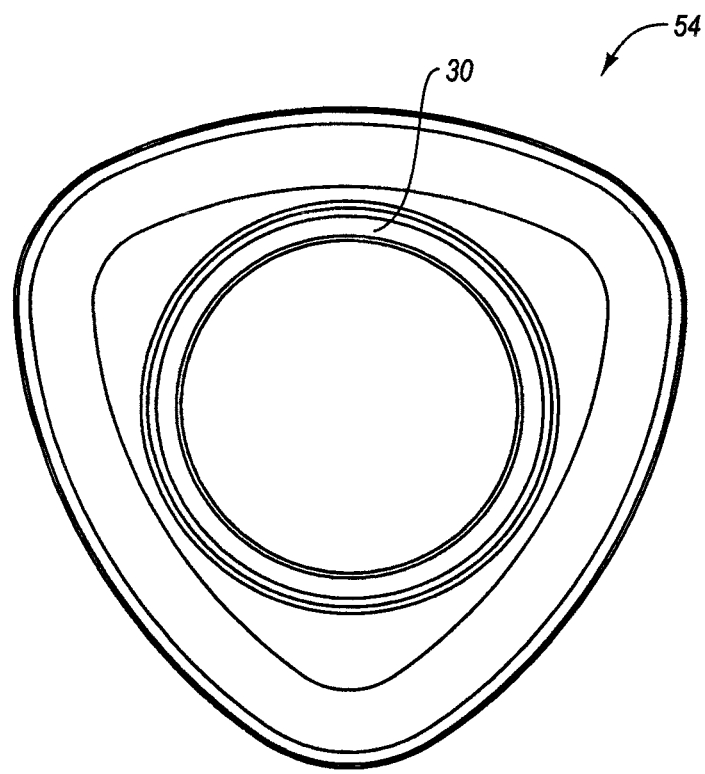
FIG. 3 shows a schematic, top elevation view of a cap including a ring feature as shown in FIGS. 1 and 2.

For example, as shown in FIGS. 1 and 2, cap 54 may optionally include a circumferential ring structure 30 that is formed adjacent to a side periphery of septum 80. Ring structure 30 may be structured to inhibit deformation of the cap 56 in response to a pressure developed within reservoir 66 of access port 50. As shown in FIG. 3, in a top elevation view of cap 54, ring structure 30 may be generally circular. Further, ring structure 30 may be substantially congruent to a side peripheral shape of septum 80 or may exhibit a different shape than the side periphery of septum 80. In addition, the size of ring structure 30 may be selected to provide a selected rigidity to a region of cap 54 adjacent to of aperture 55 of cap 54. Such a configuration may inhibit deformation of the cap 54 in response to pressure developed within reservoir 66. For example, as shown in FIG. 2, a lateral thickness $T_L$, vertical thickness $T_V$, or both may be selected for providing a selected rigidity to a region of cap 54 adjacent to a periphery of septum 80 (i.e., adjacent to aperture 55). In one embodiment, the overall height H (FIG. 2) of access port 50 may be less than about 0.600 inches.

Figure 4:
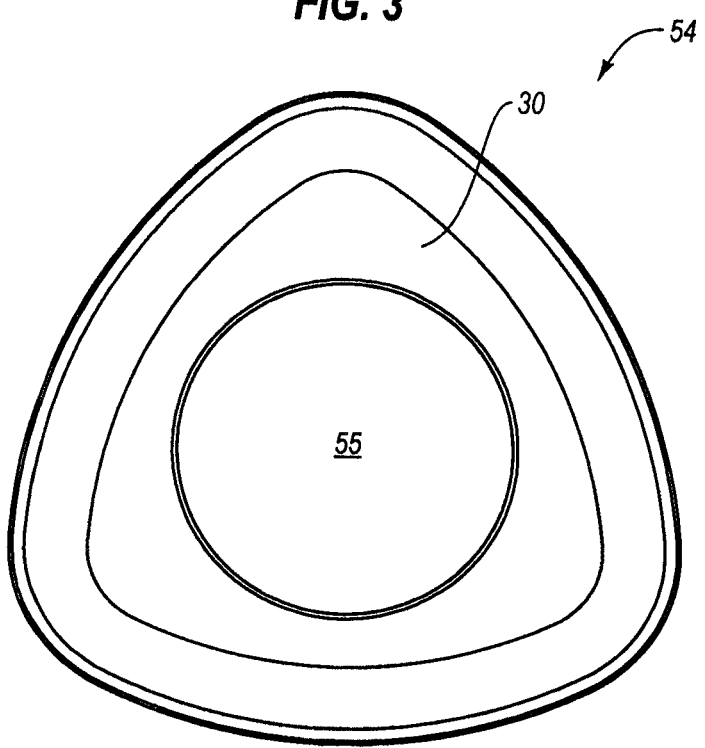
FIG. 4 shows a schematic, top elevation view of another embodiment of a cap including a ring feature.
Figure 5:
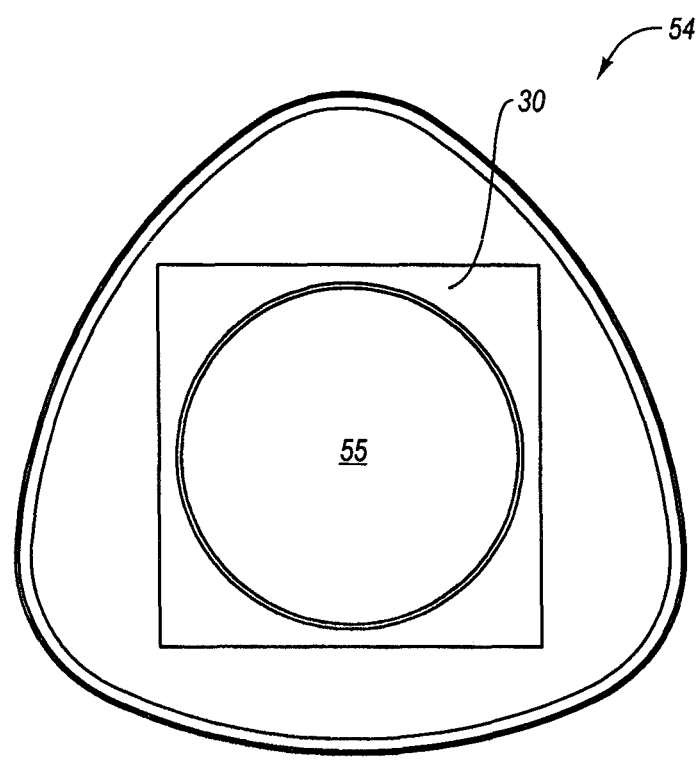
FIG. 5 shows a schematic, top elevation view of a further embodiment of a cap including a ring feature.

In other embodiments, ring structure 30 may be generally rectangular, generally triangular, generally oval, generally polygonal, or of another geometrical shape, without limitation. For example, FIG. 4 shows a top elevation view of a ring structure 30 that is generally triangular. Further, FIG. 5 shows a generally rectangular ring structure 30.

Explaining further, housing 60 of access port 50 may comprise a biocompatible material such as polysulfone, titanium, or any other suitably biocompatible material. Thus, cap 54 and base 56 may couple to one another generally along a mating line and may be secured or affixed to one another. More particularly, in one embodiment, both cap 54 and base 56 may comprise titanium and may be welded, brazed, soldered, or otherwise affixed to one another. Such a configuration may provide suitable mechanical strength for capturing septum 80 between cap 54 and base 56. Optionally, cap 54 and base 56 may be coupled to one another by at least one fastening element (e.g., at least one bolt, at least one screw, at least one rivet, etc.), at least one adhesive, or a combination of such coupling mechanisms. Similarly, in one embodiment, outlet stem 70 and base 56 may each comprise titanium and may be welded or otherwise bonded or coupled to one another.

Figure 6:
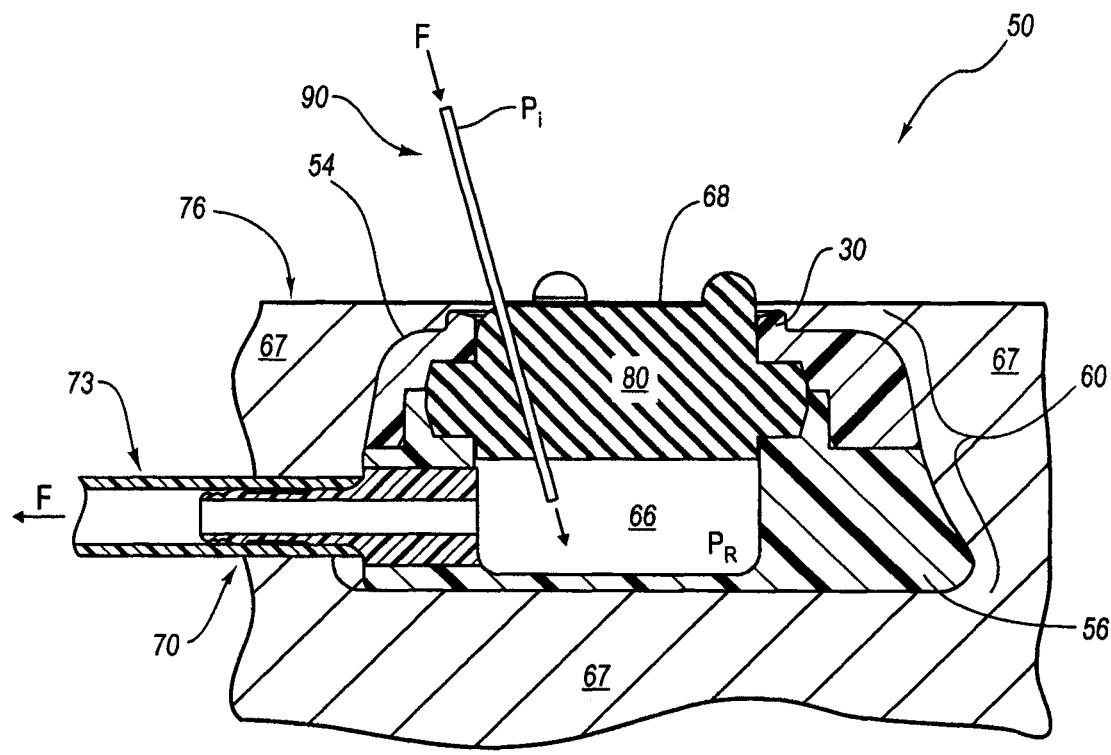
FIG. 6 shows a schematic, side cross-sectional view of an implanted access port with a cannula extending through the septum of the access port.

In further detail, FIG. 6 shows an access port 50 implanted within a patient 67. In one embodiment, sutures may be used to affix the access port 50 within the patient 67, if desired. After the housing 60 is implanted in a patient 67, the upper surface of the septum 80 may be generally flush or aligned with the surface of the skin surface 76 of the patient 67 and may be repeatedly punctured for creating a percutaneous passageway from the exterior of the skin of the patient into the reservoir 66. The outlet stem 70 may create a fluid-communicative passageway extending from the reservoir 66 and through the outlet stem 70, catheter 73, and into the interior of the patient 67. Generally, catheter 73 may be coupled to the outlet stem 70 for fluid communication with the reservoir 66 and for conducting fluid to a desired remote location from the reservoir 66 and within patient 67. In one embodiment, catheter 73 may extend from the access port 50 to at least partially within a vena cava of the patient. Such a configuration may allow for infusion of a contrast media proximate to the heart of a patient. Because such a contrast media may be harmful (e.g., radioactive or otherwise injurious) infusion directly into a vena cava of a patient may reduce an overall quantity of contrast media required to perform a selected imaging procedure.

As shown in FIG. 6, a cannula 90 may be inserted through the septum 80 and fluid may be injected into the reservoir 66. For example, fluid may be injected into reservoir 66 at a rate that causes pressure (i.e., a positive pressure) to be developed within reservoir 66. For example, a positive pressure, labeled "$P_R$" in FIG. 6, may develop within reservoir 66 and may act upon the portion of septum 80 defining, in part, reservoir 66. Such a pressure $P_R$ acting on a portion of septum 80 may develop force upon the septum 80. Likewise, force may be developed on surfaces of the base 56 that are acted upon by pressure Pr. In one embodiment, cap 54 may be coupled to base 56 and structured to suitably position septum 80 and couple septum 80 to housing 60 against force applied to the septum 80. Therefore, the septum 80, cap 54, and base 56 may be structured for accommodating attendant forces developed by pressure $P_R$. In one embodiment, access port 50 may be structured for accommodating (without damage) a pressure $P_R$ of at least about 185 psi with reservoir 66. In another embodiment, access port 50 may be structured for accommodating (i.e., without damage) a range of pressures of about 37 psi to about 65 psi with reservoir 66.

In further detail, during power injection, a fluid flow F may be caused to flow through cannula 90. A fluid flow rate (depicted in FIG. 6 by arrows labeled "F") may be at least about 1 milliliter per second. In another embodiment, a fluid flow rate F may be between about 1 milliliter per second to about 5 milliliters per second. During power injection, a pressure $P_i$ may be developed within cannula 90 may be at least about 30 psi. Accordingly, cannula 90 may be structured to withstand the forces associated with the above-discussed pressure, flow rate, or both. As discussed in further detail below, the cannula may comprise a portion of an infusion set (e.g., a safety winged infusion set (SWIS)) or another infusion system configured for use with an access port and a power injection system, without limitation.

Figure 7:
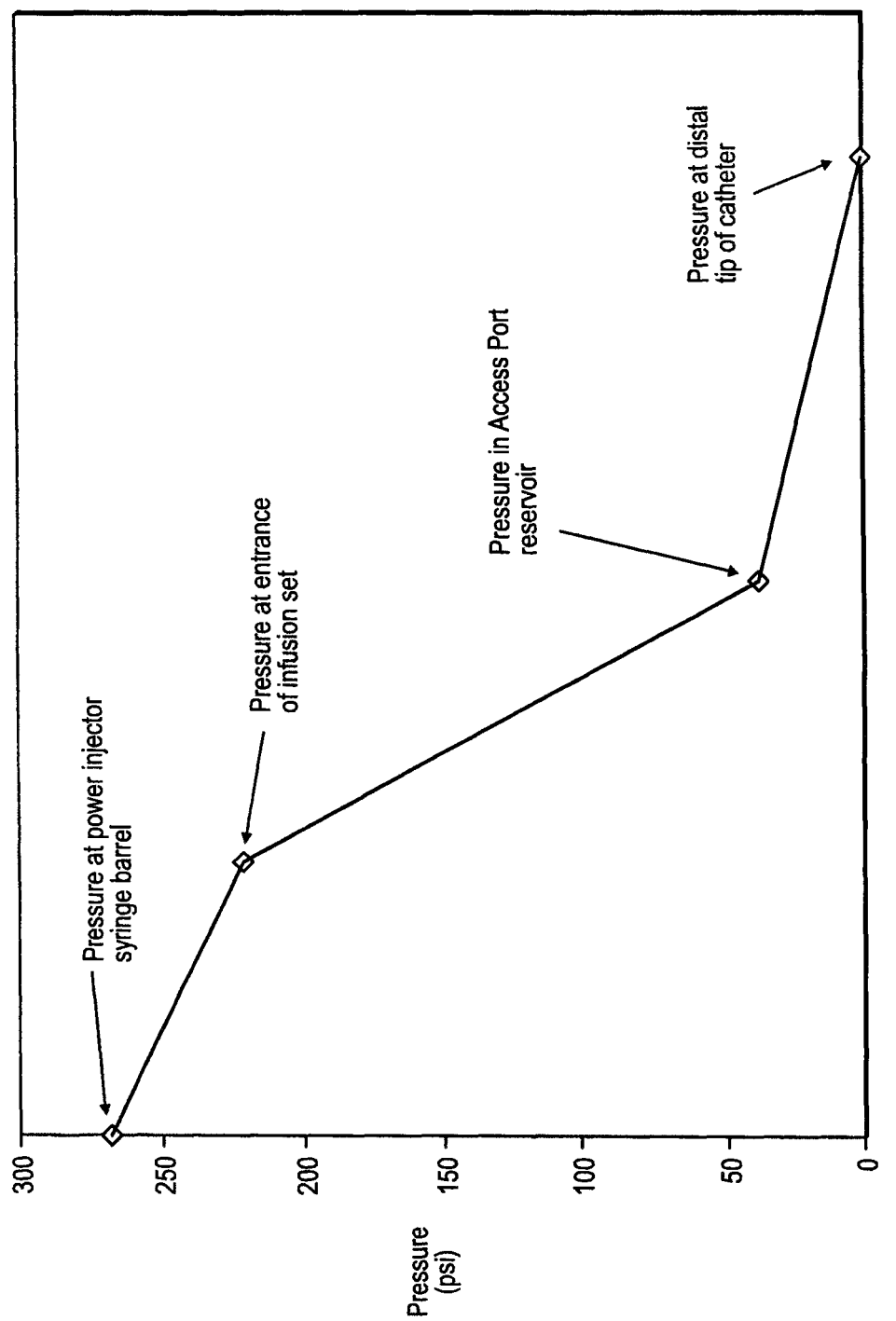
FIG. 7 shows a graph depicting pressures at selected regions within an infusion system for a given flow rate.

More particularly, FIG. 7 shows a graph depicting pressure measurements at different locations within an infusion system including an infusion set (as discussed in greater detail below) in fluid communication with an access port during infusion of a fluid at a rate of 5 milliliters per second. As shown in FIG. 7, a pressure generally within a syringe barrel of a power injector may be about 265 psi. Further, a pressure generally at the entrance of an infusion set may be about 225 psi and a pressure generally within a reservoir of an access port may be about 40 psi. Thus, the pressure drop through an infusion set may be about 185 psi. As shown in FIG. 7, a pressure generally at the distal end of a catheter extending from the access port may be about 0 psi. Many factors may influence a pressure (and a pressure drop) developed within an infusion system (e.g., infusion set, access port, etc.) during flow of a fluid through the infusion system, such as, for example, fluid viscosity, tubing inner diameter (i.e., lumen cross-sectional size), length of the flow path, and flow rate. Accordingly, as will be appreciated by the above discussion of the access port 50 shown in FIGS. 1-3, such access port 50 may be structured to accommodate a selected flow rate and associated pressure $P_R$ developed within reservoir 66 of access port 50.

In another embodiment, the septum, housing, or both may be structured to mechanically secure or constrain at least a portion of the septum. For example, in one embodiment, the septum may include at least one coupling feature configured to mate or couple with a complementary coupling feature included by the housing. For example, male and female features (e.g., without limitation, ribs, flanges, interlocking features, tenon and mortise type features, tongue-in-groove features, T-slot features, dovetail features, snap-fit features, tabs and slots or other coupling features as known in the art) may comprise the at least one coupling feature included by the septum and the at least one complementary feature included by the housing, without limitation. "Tenon," as used herein, means a projecting member for at least partial insertion into a mortise to make a joint. "Mortise," as used herein, means a recess, hole, groove, or slot formed within a material for receiving at least a portion of a tenon to make a joint.

Figure 8:
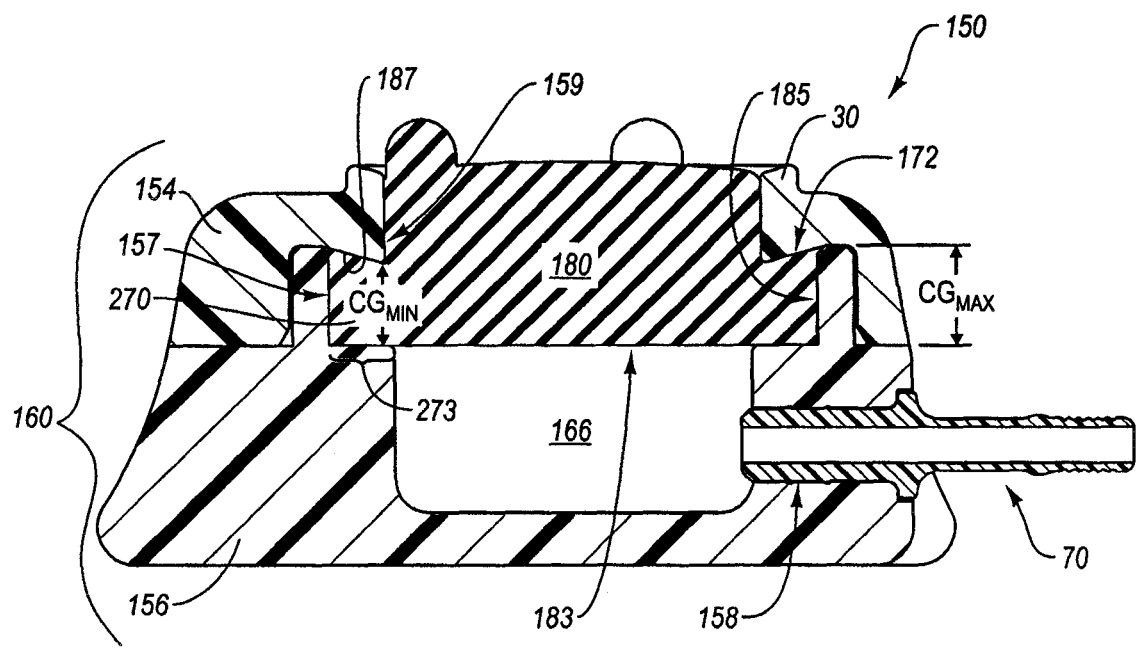
FIG. 8 shows a schematic, side cross-sectional view of an access port including a septum with a tenon region and a housing with a mortise region.

Generally, in one embodiment, the septum may include at least one tenon region (i.e., at least one coupling feature) for coupling to a complementary mortise region formed by the housing. Thus, the housing may include a recess (i.e., at least one complementary feature) for accepting at least a portion of the tenon region of the septum. For example, FIG. 8 shows a side cross-sectional view of one embodiment of a septum 180 including a tenon region 270. Particularly, tenon region 270 includes tapered surface 187 of septum 180, which may increase in height (i.e., from lower surface 183 of septum 180) along an increasing radial direction (i.e., relative to a radial distance from a central axis of septum 180; that is, in a direction from rim 159 of cap 154 toward side surface 157 of base 156). Thus, as shown in FIG. 8, a height $CG_{MIN}$ of septum 180 (measured at a radially innermost extent of tenon region 270) is less than a height $CG_{MAX}$ of septum 180 (at a radially outermost extent of tenon region 270). Further, tenon region 270 may be a continuous peripheral feature (i.e., an annular feature) of septum 180 or may comprise one or more circumferentially separate regions, without limitation. Further, as shown in FIG. 8, housing 160 (including cap 154 and base 156) may generally define a complementary mortise region (e.g., a circumferentially extending recess) for accepting at least a portion of tenon region 270. More particularly, a complementary mortise region may be defined by side surface 157 of base 156, lower flange surface 273 of base 156, and tapered surface 172 of cap 154. Such a configuration may secure, capture, or retain a portion of tenon region 270 of septum 180 within the mortise region of housing 160 even if a selected maximum pressure is developed within reservoir 166 of access port 150.

Figure 9:
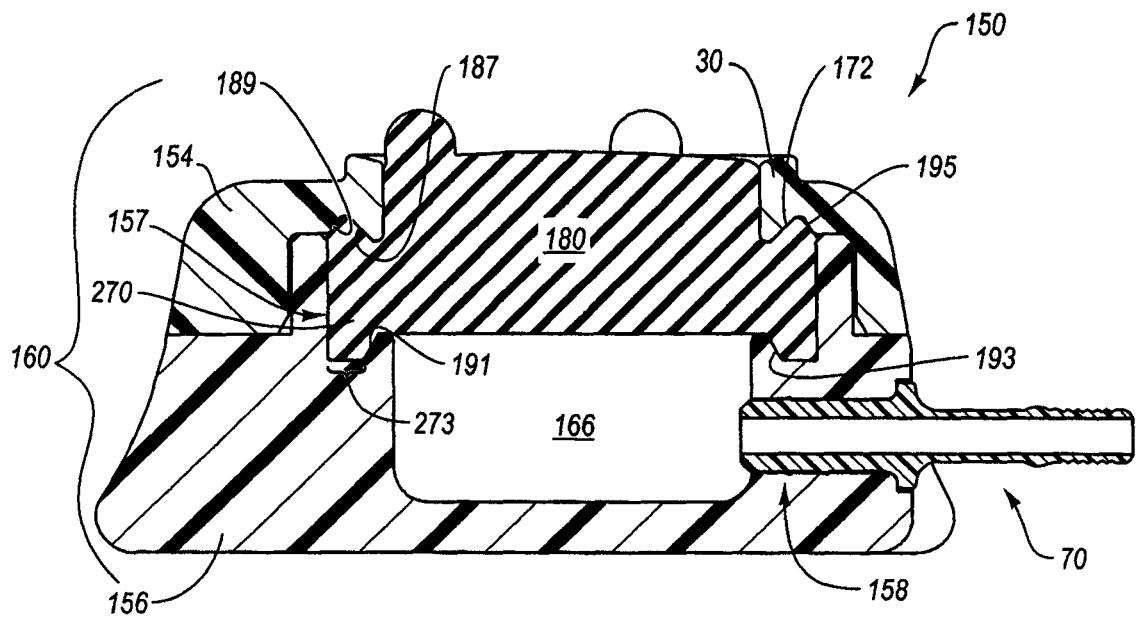
FIG. 9 shows a schematic, side cross-sectional view of another embodiment of an access port including a septum with a tenon region and a housing defining a mortise region.

In another embodiment, an access port may comprise a septum including a tenon region including a plurality of tapered surfaces. For example, FIG. 9 shows a schematic side cross-sectional view of a septum 180 including a tenon region 270 comprising tapered surface 187, tapered surface 189, and tapered surface 191. Further, as shown in FIG. 9, housing 160 may generally define a complementary mortise region tapered recess for accepting at least a portion of tenon region 270. More particularly, a complementary mortise region may be defined within housing 160 by side surface 157 of base 156, lower flange surface 273 of base 156, tapered surface 172 of cap 154, tapered surface 193 of base 156, and tapered surface 195 of cap 154. Such a configuration may secure, capture, or retain at least some of tenon portion 270 of septum 180 within a tapered recess of housing 160 even if a selected maximum pressure is developed within reservoir 166 of access port 150.

Figure 10:
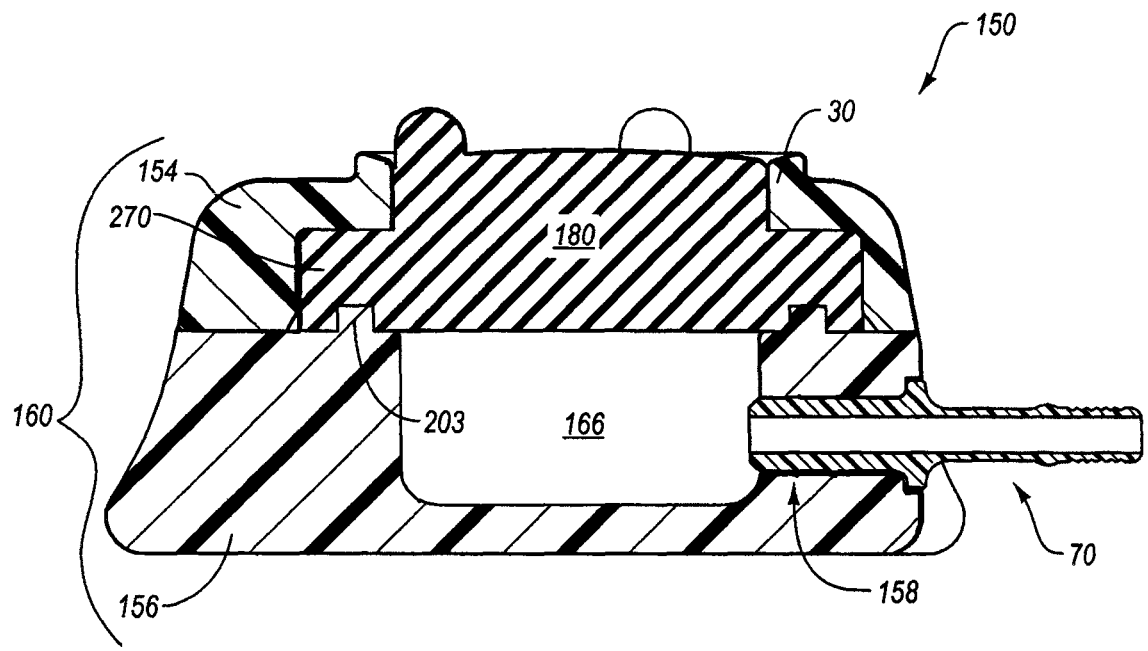
FIG. 10 shows a schematic, side cross-sectional view of a further embodiment of an access port including a tenon region and a housing defining a mortise region.

In summary, it should be understood that a portion of a septum may comprise, generally, at least one tenon region for coupling with a complementary mortise region formed in a housing. In another embodiment, generally, at least a portion of a housing may comprise a tenon for coupling with a complementary mortise formed in a septum. As described above, a tenon region and a complimentary mortise region may comprise one or more tapered surfaces. In another embodiment, a tenon region and complementary mortise region may comprise a T-slot or other non-tapered geometry, without limitation. For example, FIG. 10 shows a schematic side cross-sectional view of one embodiment of an access port 150 comprising a septum 180 including a tenon region 270. Further, a complementary mortise region may be defined within housing 160 for accepting at least a portion of tenon region 270. As shown in FIG. 10, a mortise region may be at least partially defined by an annular extension or protrusion 203 of base 156. Such a configuration may secure, capture, or retain at least a portion of tenon region 270 of septum 180 within housing 160 and suitably seal reservoir 166 even if an anticipated maximum pressure is developed within reservoir 166. It should be further understood that any of the tenon region and mortise region embodiments shown in FIGS. 8-10 may be described in terms of extensions, ridges, protrusions, recesses, grooves, slots, etc., without limitation.

Figure 11:
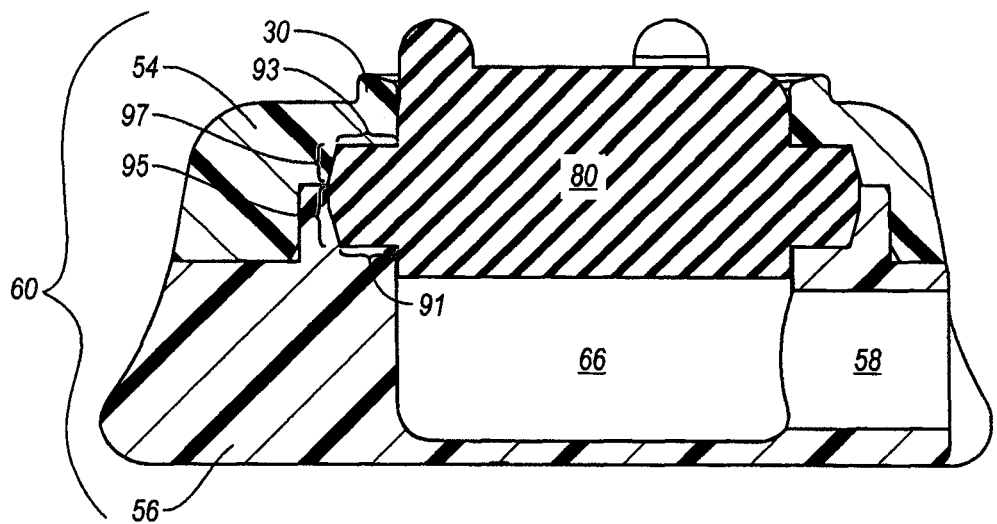
FIG. 11 shows a schematic, side cross-sectional view of an access port, wherein at least a portion of a side periphery of the septum is affixed to the housing.

A further aspect contemplated by the instant disclosure relates to coupling or affixing at least a portion of a peripheral region of a septum to a housing. Such a configuration may maintain the integrity of the access port during use of the access port for infusing a fluid at a flow rate of at least about 1 milliliter per second. For example, in one embodiment, at least a portion of a side periphery of a septum may be affixed to at least a portion of a housing. FIG. 11 shows a side cross-sectional view of an access port 50 wherein at least a portion of a periphery of septum 80 adjacent to housing 60 is affixed to one or both of cap 54 and base 56 adjacent to septum 80. More particularly, as shown in FIG. 11, a periphery of septum 80 (adjacent to cap 54 and base 56) may include upper side region 97, upper annular region 93, lower annular region 91, and lower side region 95. Thus, in one embodiment, an adhesive, (e.g., glue, epoxy, cement, tape, or any other adhesive as known in the art) may affix at least a portion of one or more of upper side region 97, upper annular region 93, lower annular region 91, and lower side region 95 to the cap 54 or base 56, respectively. Such a configuration may secure septum 80 to housing 60 and may provide a relatively robust access port 50 suitable for power injection. It should further be appreciated that affixing at least a portion of a peripheral region of a septum may encompass affixing at least a portion of a tenon region (of either a septum or housing) to a mortise region (of either a housing or septum), without limitation.

As described above, septum deformation is a design consideration with respect to performing power injection via an access port. Further, one aspect of the instant disclosure relates to a septum that is structurally reinforced or otherwise limited against deformation exceeding a selected magnitude. More specifically, the instant disclosure contemplates that at least one structural element may be configured to inhibit or limit deformation of a septum of an access port in response to pressure developed within a chamber or reservoir of the access port. Some embodiments of an access port including at least one structural element for limiting deformation of a septum are disclosed in U.S. Patent Application No. 60/737,466, filed 15 Nov. 2005, the disclosure of which is incorporated, in its entirety, by this reference. Any of the access ports encompassed by U.S. Patent Application No. 60/737,466 may be structured for power injection.

Figure 12:
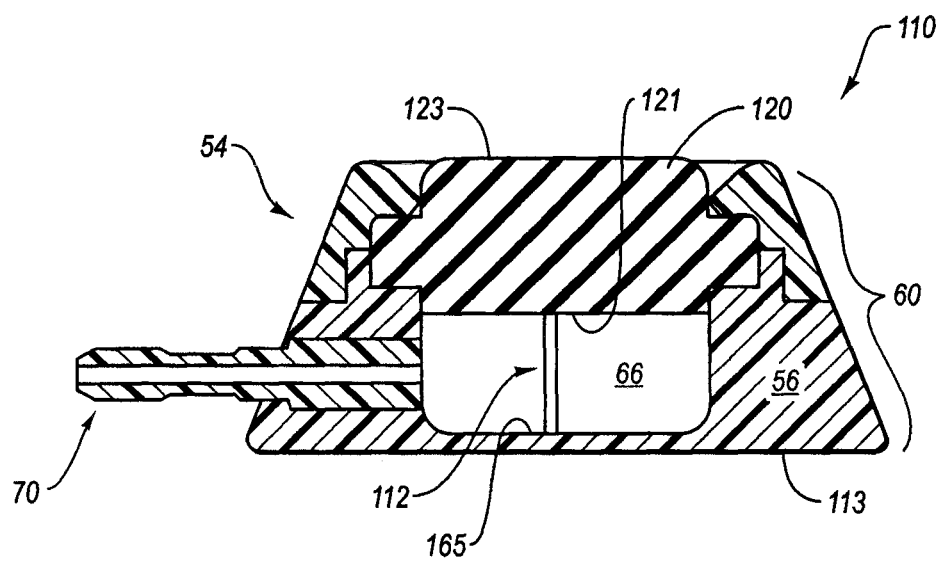
FIG. 12 shows a schematic, side cross-sectional view of an access port including a structural element extending between the septum and the housing.

In one embodiment, the instant disclosure contemplates that a septum may be structurally coupled to a housing nonperipherally. Put another way, one aspect of the instant disclosure relates to coupling a nonperipheral portion of a septum to a housing of an access port. For example, FIG. 12 shows one embodiment of an access port 110 according to the instant disclosure including a cap 54 and a base 56 that capture a septum 120 to form a reservoir 66. Optionally, cap 54 may include a ring feature proximate to a periphery of the septum, as described above. In addition, outlet stem 70 may allow for fluid communication with reservoir 66 to perform infusion or fluid sampling processes. As shown in FIG. 12, a structural element 112 may extend between septum 120 and housing 60. More particularly, structural element 112 extends generally from lower surface 121 of septum 120 to upper surface 165 of base 56. Thus, if pressure (positive/negative) is developed within reservoir 66, structural element 112 may inhibit deflection or deformation of lower surface 121 of septum 120 toward or away from upper surface 165 of base 56. Generally, a structural element may inhibit deformation of a septum in relation to one or more selected directions (i.e., either toward or away from upper surface 165 of base 56).

Generally, a structural element (e.g., structural element 112) may comprise any of the following: at least one wire, at least one pin or columnar element, or at least one filament, without limitation. Such a structural element may comprise titanium, steel (e.g., stainless steel), polymers (e.g., DELRIN®, nylon, polyester, KEVLAR®, polytetrafluoroethylene (PTFE) (expanded or nonexpanded), polyurethane, etc.), or other materials as known in the art. In other embodiments, a structural element may comprise a composite, such as a fiber-reinforced matrix. In one embodiment, a structural element may comprise fibers (glass, carbon, etc.) dispersed or aligned within a silicone matrix.

Further, structural element 112 may be coupled to septum 120 by an adhesive, welding, snap-fitting, molding the septum 120 about a portion of the structural element 112, otherwise imbedding a portion of structural element 112 within septum 120, or as otherwise suitable. Similarly, structural element 112 may be coupled to base 56 by an adhesive, welding, or imbedding a portion of structural element 112 within base 56. It may also be appreciated that, optionally, structural element 112 may exhibit a modulus of elasticity that exceeds a modulus of elasticity of septum 120. Such a configuration may allow for structural element 112 to resist deformation of septum 120 in response to a pressure developed within reservoir 66 (e.g., during a "power injection" process).

Figure 13:
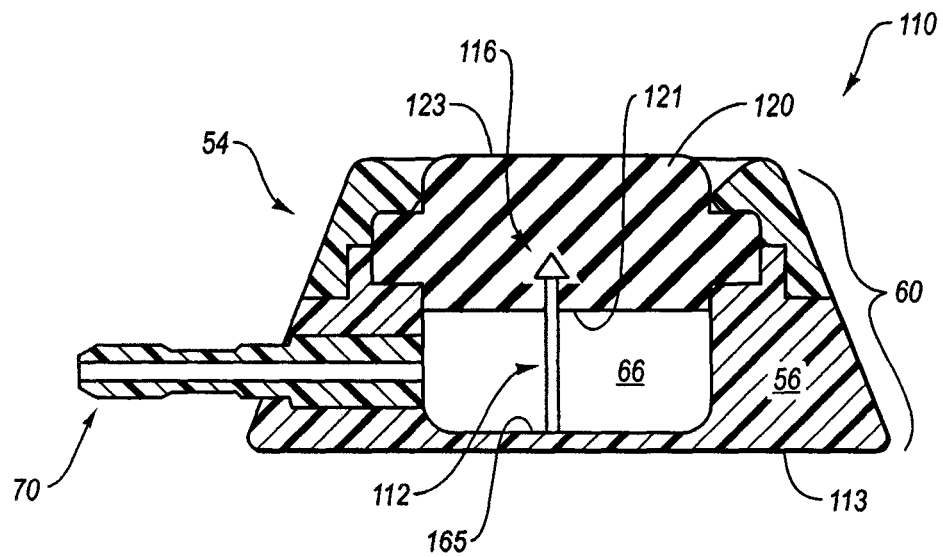
FIG. 13 shows a schematic, side cross-sectional view of an access port including a structural element with a barbed end positioned within the septum.

FIG. 13 shows a schematic cross-sectional view of an access port 110 according to the instant disclosure including another embodiment of structural element 112. Particularly, as shown in FIG. 13, structural element 112 may include a barbed end 116, which is positioned at least partially within septum 120. Such a configuration may couple structural element 112 to septum 120 and may resist against deformation of the septum 120 in response to pressure developed within reservoir 166. Furthermore, as shown in FIG. 13, the barbed end 116 of structural element 112 may, optionally, be pointed. Further, the point of barbed end 116 may be oriented toward upper surface 123 of septum 120. Such a structure may deflect a cannula that is inserted through septum 120 and contacts barbed end 116 so that the cannula is directed away from structural element 112. Optionally, in another embodiment, structural element 112 may extend through base 56 and may be affixed to lower surface 113 of base 56.

Figure 14:
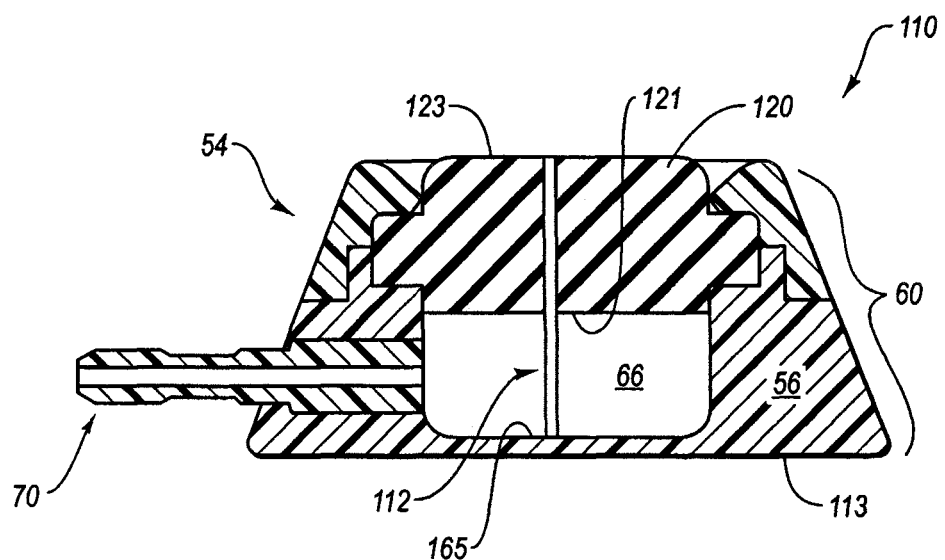
FIG. 14 shows a schematic, side cross-sectional view of an access port including a structural element extending between an upper surface of the septum and the housing.

In another embodiment of an access port, a structural element may extend through a septum. For example, FIG. 14 shows a schematic, side cross-sectional view of an access port 110 including a structural element 112 that extends from lower surface 121 of septum 120 to upper surface 123 of septum 120. As shown in FIG. 14, structural element 112 may also extend to upper surface 165 of base 56, to mechanically couple septum 120 to housing 60. Optionally, structural element 112 may include at least one barb, which may be positioned within septum 120 and configured for coupling septum 120 to housing 60. In addition, structural element 112 may be affixed, if desired, to at least one of upper surface 123 and lower surface 121 of septum 120. As may be appreciated, it may be advantageous for upper surface 123 of septum 120 to be mechanically coupled to housing 60 to resist deformation of septum 120 in response to a pressure developed within reservoir 66.

Figure 15:
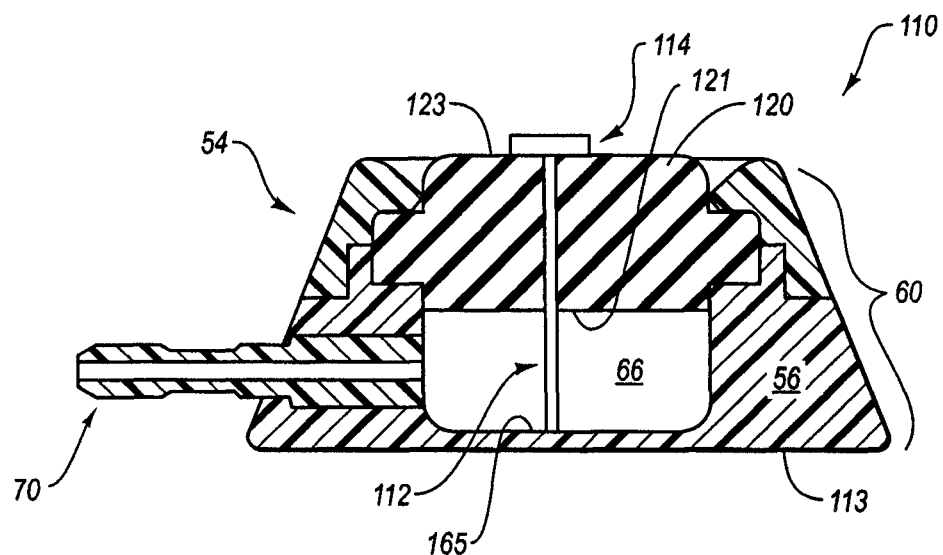
FIG. 15 shows a schematic, side cross-sectional view of an access port as shown in FIG. 14 and also including a support element positioned adjacent to an upper surface of the septum.

The instant disclosure further contemplates that a structural element may be employed in combination with a support element extending over a selected area of the upper surface of the septum. Such a support element may be positioned adjacent to an upper surface of a septum and may be configured to contact the upper surface of the septum with a selected surface area (e.g., when the septum deforms). For example, FIG. 15 shows a schematic, side cross-sectional view of an access port 110 including a structural element 112 that extends from housing 60 to an upper surface 123 of septum 120. Furthermore, structural element 112 is coupled to a support element 114, which is positioned adjacent to upper surface 123 of septum 120. Such a configuration may provide a selected amount of contact area between support element 114 and upper surface 123 of septum 120. Such a selected contact area between support element 114 and septum 120 may reduce otherwise undesirably high stresses within septum 120 when a pressure develops within reservoir 66 by distributing such stresses over a selected area or region of septum 120. In addition, support element 114 may be observable (e.g., visually or by palpation) and, therefore, may be avoided when inserting a cannula through septum 120. Additionally, the support element 114 can be used to identify the port 110 as being power injectable.

Figure 16:
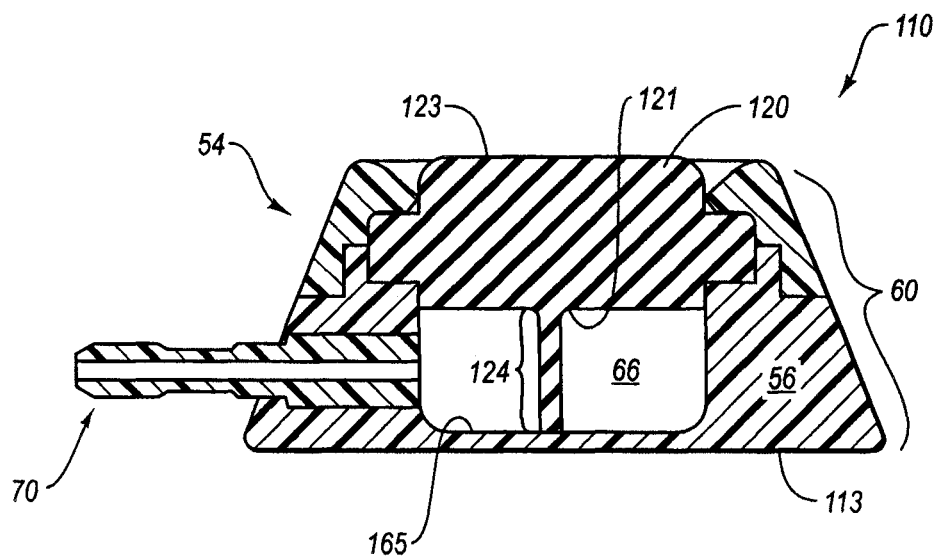
FIG. 16 shows a schematic, side cross-sectional view of an access port including a septum with an extension leg that extends to the housing.
Figure 17:
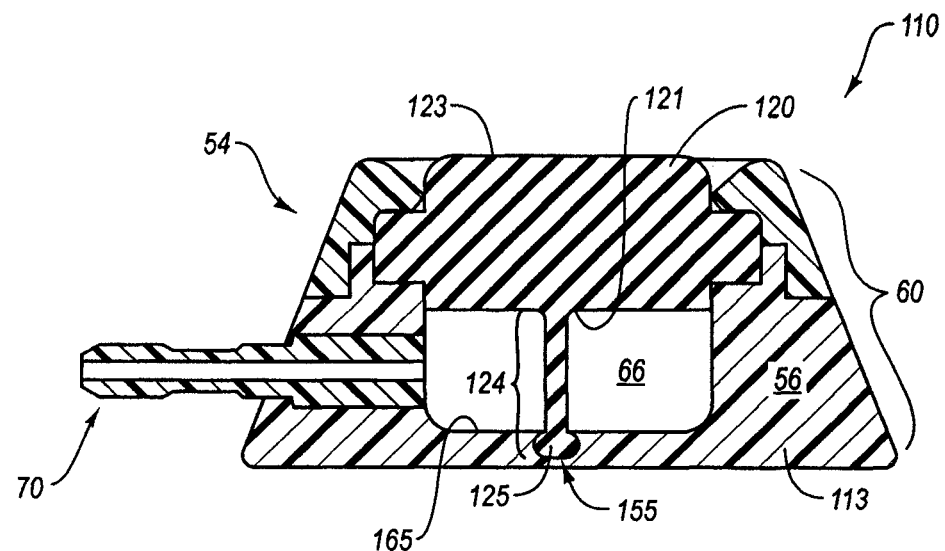
FIG. 17 shows a schematic, side cross-sectional view of an access port including a septum with an extension leg comprising an enlarged end that couples to a recessed form in the housing.

In another embodiment of an access port, a structural element may comprise a portion of a septum affixed to a housing of an access port to resist deformation of the septum. For example, FIG. 16 shows a schematic, side cross-sectional view of an access port 110 including a septum 120, which comprises an extension leg 124 (i.e., a structural element) that is coupled to housing 60. More particularly, as shown in FIG. 16, extension leg 124 may extend generally from lower surface 121 of septum 120 to upper surface 165 of base 56. Extension leg 124 may abut and may be affixed to upper surface 165 of base 56. Such a configuration may resist against deformation of septum 120 in response to pressure developed within reservoir 166. In one embodiment, extension leg 124 may be substantially centered (i.e., positioned generally at a centroid of lower surface 121) with respect to lower surface 121 of septum 120. Substantially centering extension leg 124 with respect to lower surface 121 of septum 120 may limit deformation of lower surface 121 of septum 120 to a greater extent than other positions of extension leg 124 may limit deformation of lower surface 121 of septum 120. Additionally, it should be appreciated that while FIG. 16 shows one extension leg 124, the instant disclosure contemplates that at least one extension leg (i.e., one or more extension legs) may extend from or be coupled to septum 120, without limitation. In another embodiment, at least one extension leg may be coupled to a housing of an access port by an interference fit or a so-called "snap-fit." More particularly, as shown in FIG. 17, extension leg 124 includes a bulbous or rounded end 125 that is configured to fit within a recess 155 formed in base 56. Recess 155 may comprise an opening formed in upper surface 165 of base 56 that is smaller than a maximum lateral dimension of rounded end 125, so that rounded end 125 may be forced through such an opening and "snap" into a portion of recess 155. Optionally, extension leg 124 may be affixed (e.g., adhesively affixed, welded, pinned, or affixed by other suitable methods to recess 155 formed in base 56. Such a configuration may couple septum 120 to base 60 of access port 110 and may resist or limit deformation of septum 120 in response to pressure developed within reservoir 66.

Figure 18:
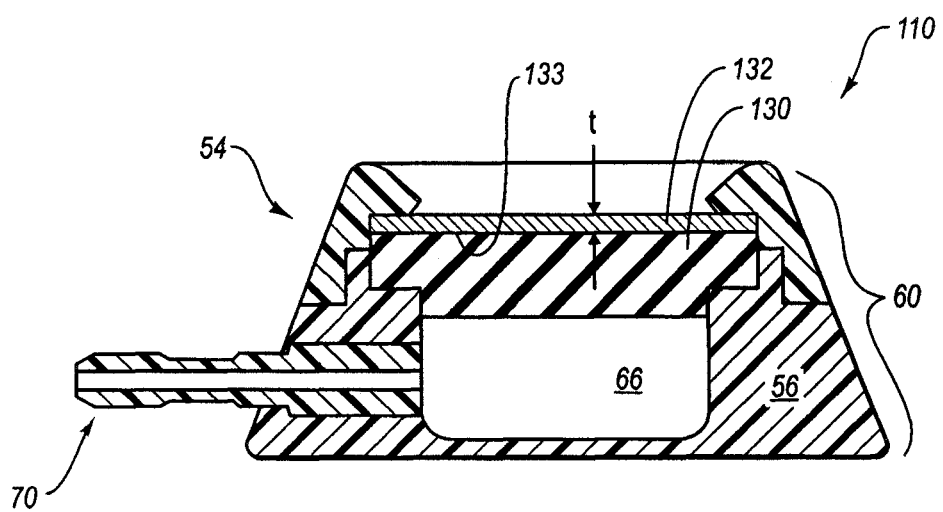
FIG. 18 shows a schematic, side cross-sectional view of an access port including a septum in a structural element positioned adjacent to an upper surface of the septum.

Another aspect of the instant disclosure contemplates that at least a portion of an upper surface of a septum may be constrained or limited in its deformation. In one embodiment, at least one structural element may be positioned upon or adjacent to an upper surface of a septum to limit deformation of the septum in a direction toward the structural element. Put another way, at least one structural element may extend laterally upon or adjacent to at least a portion of an upper surface of a septum. For example, FIG. 18 shows a schematic, side cross-sectional view of an access port 110 including a septum 130 and a structural element 132 positioned adjacent to an upper surface 133 of septum 130. Optionally, structural element 132 may be bonded or affixed to upper surface 133 of septum 130. Structural element 132 may be structured to resist deformation of septum 130 in a direction generally away from reservoir 166. In one embodiment, structural element 132 may substantially overlay or cover upper surface 133 of septum 130. Optionally, structural element 132 may be at least partially embedded within septum 130. In one embodiment, structural element 132 may be penetrable by a cannula (e.g., a needle). In another embodiment, structural element 132 may cover a selected portion (i.e., at least a portion) of upper surface 133 of septum 130, which may allow for openings or apertures formed in structural element 132 through which a cannula may be inserted into upper surface 133 of septum 130. It may be appreciated that, optionally, a modulus of elasticity of structural element 132 may exceed a modulus of elasticity of septum 130, so that deformation of septum 130 may be inhibited to a selected degree by structural element 132. Further, although a thickness (labeled "t") of structural element 132 is shown in FIG. 18 as being substantially uniform, the instant disclosure contemplates that a thickness "t" of structural element 132 may vary, without limitation. For example, thickness "t" of structural element 132 may be maximum proximate to a centroid of the upper surface 133 of septum 130. In addition, as shown in FIG. 18, structural element 132 may be positioned between cap 54 and septum 130. Structural element 132 may be affixed to one or both of cap 54 and septum 130, if desired. For example, structural element 132 may be adhesively affixed, welded, mechanically fastened, or otherwise suitably coupled to one or both of cap 54 and septum 130. Furthermore, structural element 132 may comprise a metal (e.g., titanium, steel, etc.), a polymer (e.g., DELRIN® polyurethane, nylon, etc.), or any other suitable material. In another embodiment, as discussed further below, structural element 132 may comprise a relatively tightly woven fabric that resists tissue ingrowth (if positioned in potential contact with an internal cavity of the body). In a further embodiment, a structural element 132 may comprise a substantially fluffy or compressible polyester that may promote tissue healing of punctures created by a cannula passing through septum 130 of access port 110 (if positioned in potential contact with an internal cavity of the body).

Figure 19:
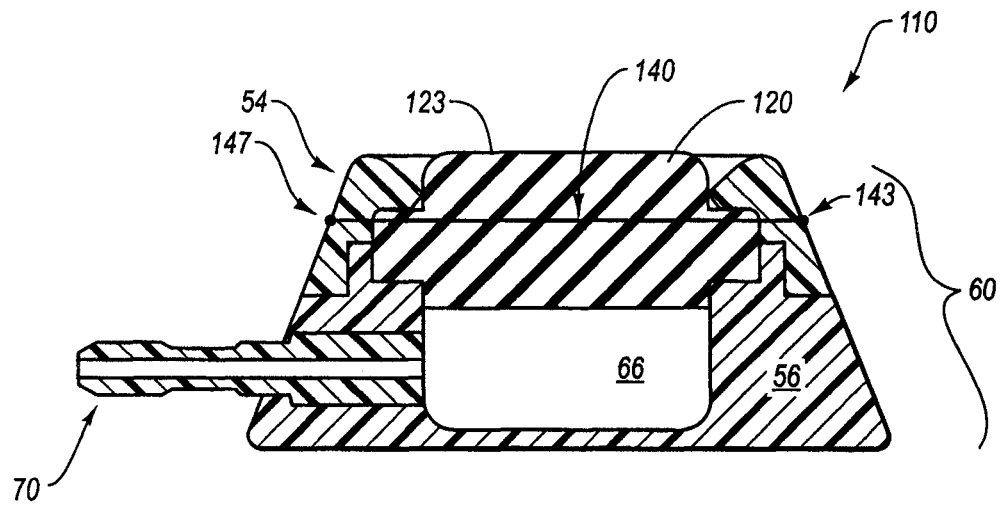
FIG. 19 shows a schematic, side cross-sectional view of an access port including a septum and a structural element extending laterally through the septum.

In a further embodiment, the instant disclosure contemplates that at least one structural element may be at least partially embedded within a septum and may extend laterally through at least a portion of the septum. For example, FIG. 19 shows a schematic, side cross-sectional view of an access port 110 including a septum 120 and a structural element 140 extending laterally (i.e., across an opening in the housing 60 closed by the septum 120) through the septum 120. As shown in FIG. 19, structural element 140 may be affixed to housing 60 (e.g., cap 54 or base 56). More particularly, as shown in FIG. 19, structural element 140 may be affixed to cap 154 at connection regions 147 and 143. In addition, a selected level of tension may be developed within structural element 140, if desired, to provide for a desired level of resistance to deformation (i.e., flexibility) of septum 120. Such a configuration may provide a selected degree of resistance to deformation of septum 120 in a direction generally perpendicular to a direction of extension of structural element 140.

Figure 20:
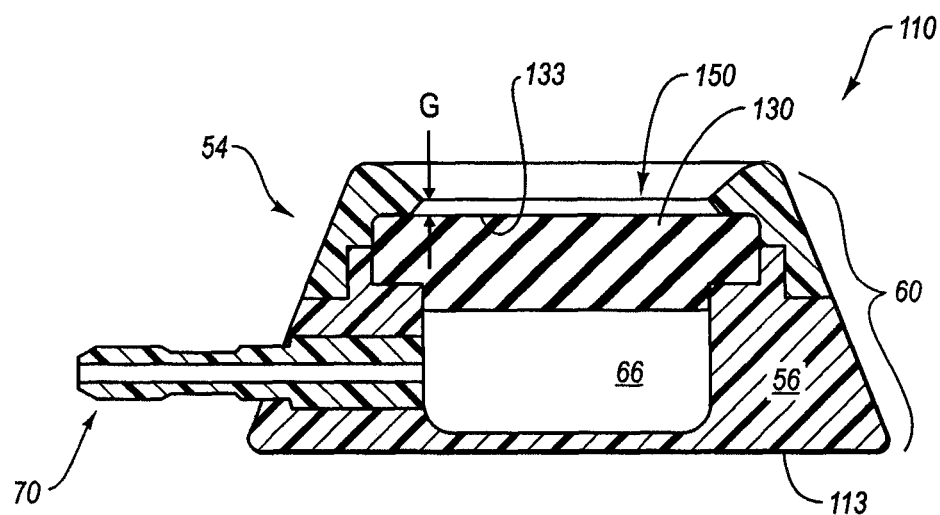
FIG. 20 shows a schematic, side cross-sectional view of an access port including a septum and a structural element positioned proximate to an upper surface of the septum.

In another embodiment, a structural element may be positioned proximate to an upper surface of a septum to limit deformation of the septum. For example, FIG. 20 shows a schematic, side cross-sectional view of an access port 110 including a septum 130 positioned within a housing 60 and a structural element 150 positioned proximate to an upper surface 133 of septum 130. As shown in FIG. 20, structural element 150 extends laterally over at least a portion of upper surface 133 of septum 130. Thus, structural element 150 may allow septum 130 to deform a selected distance (e.g., a gap labeled "G") prior to contact with structural element 150. Further, structural element 150 may be affixed to cap 54 and may be selectively tensioned to exhibit a selected degree of flexibility in response to contact between septum 130 and structural element 150. In one embodiment, structural element 150 may exhibit a flexibility or spring constant that exceeds a bulk flexibility or spring constant of septum 130 in response to a pressure developed within reservoir 66.

Figure 21:
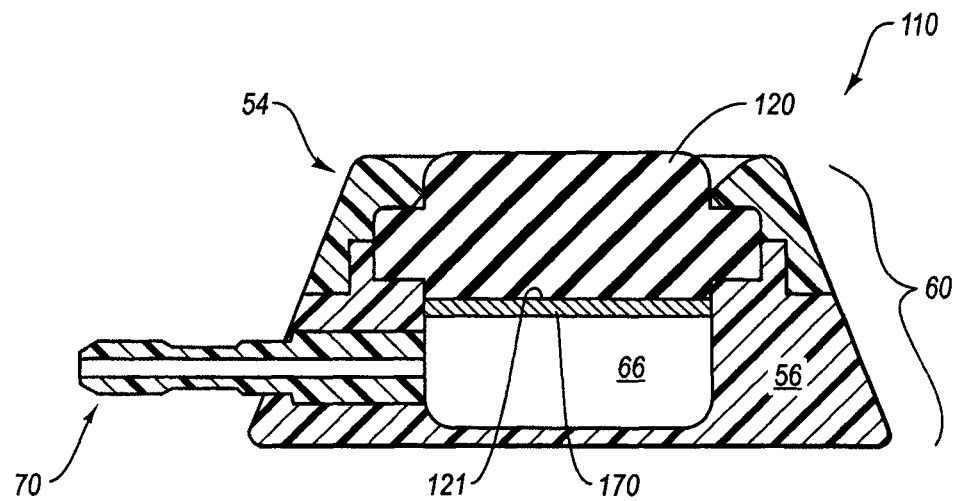
FIG. 21 shows a schematic, side cross-sectional view of an access port including a septum and a structural element positioned proximate to a lower surface of the septum.

In another embodiment, a structural element may be positioned proximate to or abutting a lower surface of a septum to limit deformation of the septum. For example, FIG. 21 shows a schematic, side cross-sectional view of an access port 110 including a septum 120 positioned within a housing 60 and a structural element 170 positioned proximate to a lower surface 121 of septum 120. As shown in FIG. 21, structural element 170 may extend laterally over at least a portion of lower surface 121 of septum 120. Further, structural element 170 may be affixed to lower surface 121 or septum 120 or otherwise coupled to lower surface 121 of septum 120. Thus, structural element 170 may inhibit deformation of septum 120. Further, structural element 170 may be affixed to base 56 (or otherwise coupled to housing 60) to provide adequate resistance to deformation of septum 120. Optionally, structural element 170 may be selectively tensioned to exhibit a selected flexibility in response to forces applied to the structural element 170. Optionally, structural element 170 may exhibit a flexibility or spring constant that exceeds a bulk flexibility or spring constant of septum 120.

Referring to FIGS. 18-21, it will be appreciated that structural elements 132, 140, 150, or 170 may comprise, in some embodiments, elongated elements, such as, for instance, wire, ribbon, thread, fibers, columnar elements, or the like. Accordingly, such at least one elongated element may be arranged in a selected pattern adjacent or proximate to an upper surface of a septum. Further, in one embodiment, a structural element positioned proximate to or abutting a lower surface of a septum, proximate to or abutting an upper surface of a septum, or within a septum, may comprise a mesh (e.g., a metal or plastic mesh, a fabric, a fiber mesh, etc.). For instance, in one embodiment, a structural element may comprise a fabric comprising fibers or threads that seal against one another (e.g., fibers or threads coated with silicone). Such a configuration may allow for a cannula to pass through the fabric and for the fabric to seal about the cannula, but may also allow for the fibers or threads to seal against one another when the cannula is removed. In addition, it will be understood that, based upon the instant disclosure, structural elements 132, 140, 150, or 170 as shown in FIGS. 18-21 may be arranged in a variety of configurations.

Figure 22:
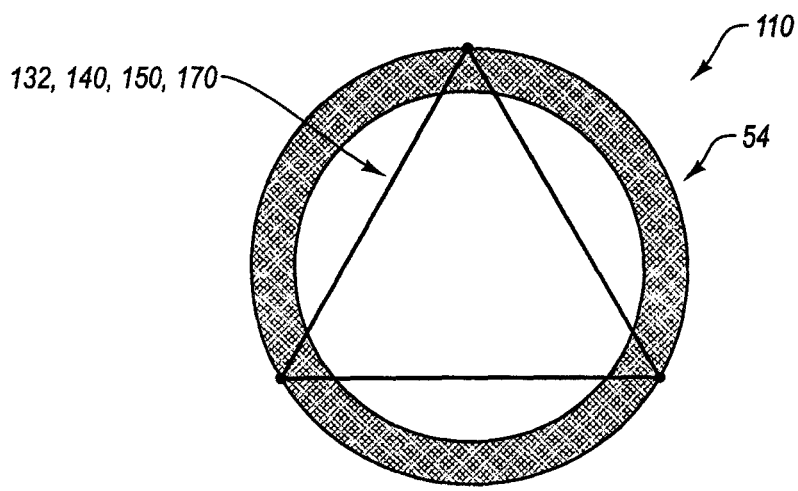
FIG. 22 shows a partial, top elevation view of an access port, as shown in FIGS. 18-21, wherein structural elements are arranged in a generally triangular pattern.
Figure 23:
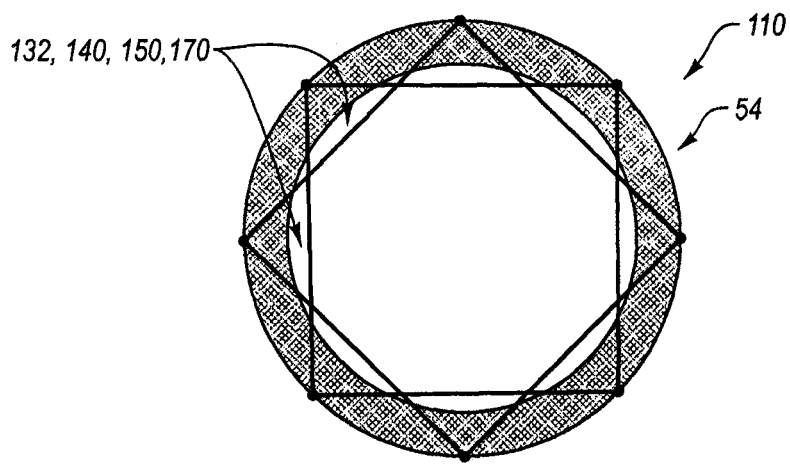
FIG. 23 shows a partial, top elevation view of an access port, as shown in FIGS. 18-21, wherein structural elements are arranged in two generally rectangular patterns.
Figure 24:
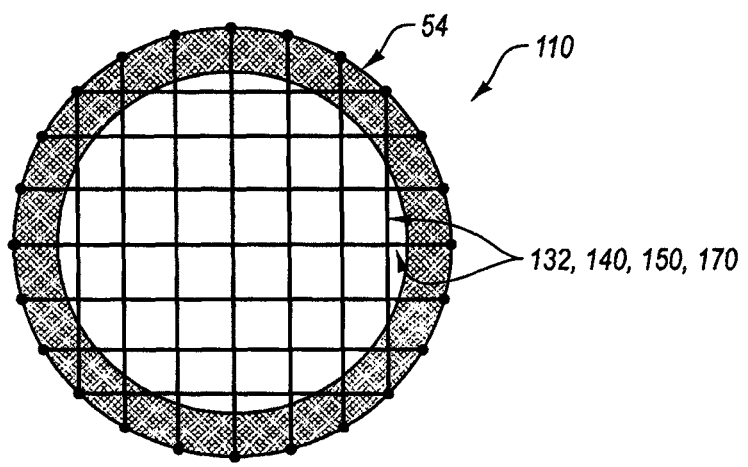
FIG. 24 shows a partial, top elevation view of an access port, as shown in FIGS. 18-21, wherein structural elements are arranged in a first plurality of substantially parallel lines and a second plurality of substantially parallel lines.
Figure 25:
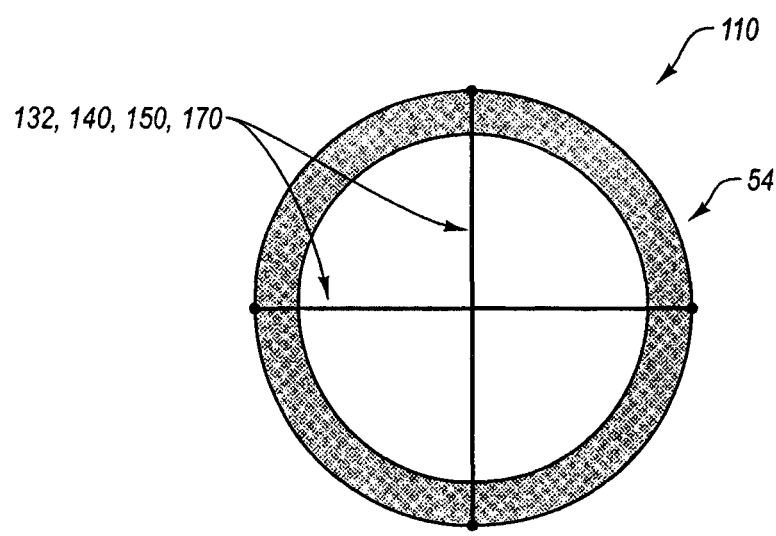
FIG. 25 shows a partial, top elevation view of an access port as shown in FIGS. 18-21, wherein structural elements are arranged as two intersecting substantially straight members.

For example, FIG. 22 shows a partial top elevation view of one embodiment of an access port 110, as shown in FIGS. 18-21, wherein structural elements 132, 140, 150, 170 are arranged to form a generally triangular shape or pattern. In a further example, FIG. 23 shows a partial top elevation view of an access port 110 as shown in FIGS. 18-21, wherein structural elements 132, 140, 150, 170 are arranged in two partially intersecting generally rectangular shapes or pattern. In yet a further embodiment, FIG. 24 shows a partial top elevation view of an access port 110, as shown in FIGS. 18-21, wherein structural elements 132, 140, 150, 170 are arranged as a pattern comprising a first plurality of substantially parallel lines and a second plurality of substantially parallel lines, wherein the first plurality of substantially parallel lines is substantially perpendicular to and intersects with the second plurality of substantially parallel lines. In an additional embodiment, FIG. 25 shows a partial top elevation view of an access port 110, as shown in FIGS. 18-21, wherein structural elements 132, 140, 150, 170 are arranged as a pattern comprising two substantially straight (i.e., linear) members that intersect with one another. As shown in FIG. 25, structural elements 132, 140, 150, 170 may be substantially perpendicular to one another. As shown in FIGS. 22-25, structural elements 132, 140, 150, 170 may be affixed to cap 54 at selected connection regions. Such configurations may allow for varying degrees of limitation of deformation of a septum, while allowing ample access to a surface of a septum for perforation by a cannula (e.g., a needle).

Figure 26:
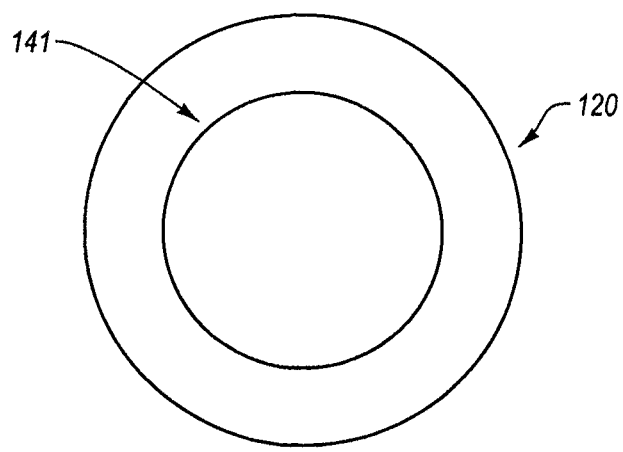
FIG. 26 shows a partial, top elevation view of a septum including a structural element positioned within the septum.
Figure 27:
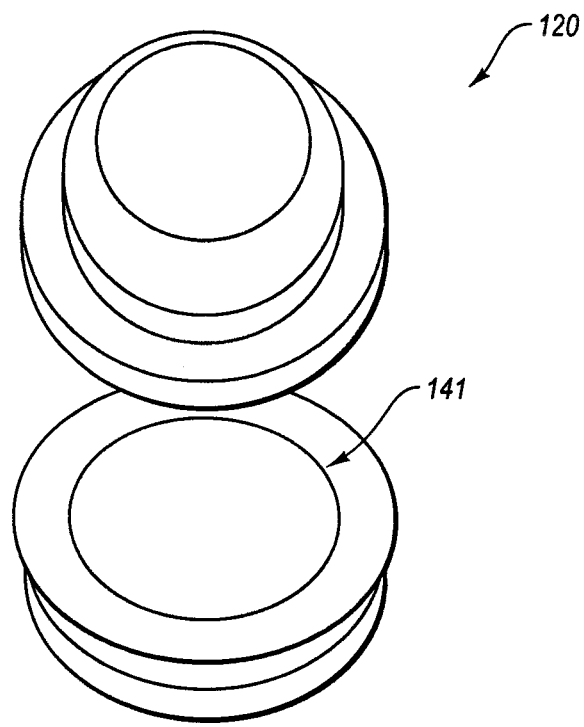
FIG. 27 shows a perspective view of a sectioned septum, as shown in FIG. 26.
Figure 28:
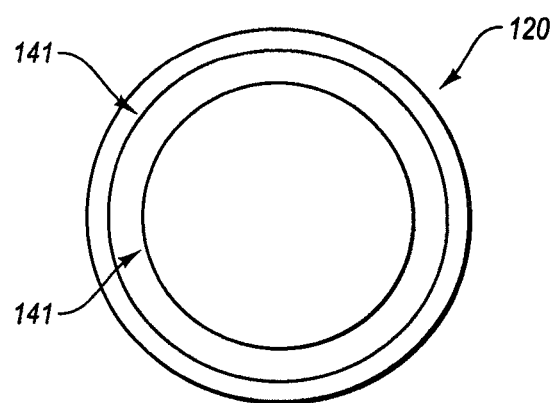
FIG. 28 shows a partial, top elevation view of a septum including a plurality of structural elements.

In another embodiment, the instant disclosure contemplates that a structural element may be at least partially embedded within a septum and may be in the form, configuration, or shape of a two-dimensional or plane (e.g., a circle, ellipse, triangle, rectangle, etc.) within the septum. For example, FIG. 26 shows a partial top elevation view of a septum 120 and a structural element 141 extending within the septum 120. In further detail, FIG. 27 shows a perspective view of a sectioned septum 120 including a structural element 141 embedded within the septum 120. As shown in FIGS. 26 and 27, in one embodiment, structural element 141 may be generally circular. More generally, one or more structural elements 141 may be at least partially embedded within a septum (e.g., a septum 120 or 130, as discussed above), if desired. For example, a plurality of structural elements 141 may be embedded within a septum 120 and arranged substantially concentrically with respect to one another, as shown in FIG. 28 in a partial, top elevation view. Structural element 141 may be generally elongated (as shown in FIGS. 26-28) or may, more generally, exhibit a shape and size configured to resist deformation of the septum 120, without limitation. Thus, it should be appreciated that one or more structural elements 141 may embody, for example, a washer or a disk that is frustoconical, domed, or otherwise shaped. In another embodiment, at least one structural element 141 may form, generally, a toroid. Further, at least one structural element 141 may exhibit at least one selected characteristic (e.g., exhibiting a selected size, shape, elasticity, strength, etc.) to impart a desired level of resistance to deformation (i.e., flexibility) of septum 120. Such a configuration may provide a selected level of resistance to deformation of septum 120 in response to a pressure developed within a reservoir of an access port.

Figure 29:
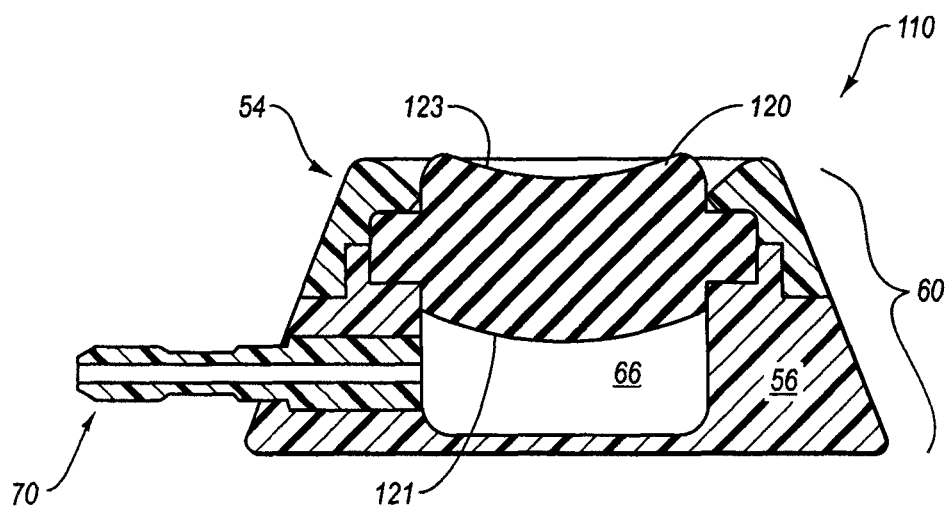
FIG. 29 shows a schematic, side cross-sectional view of an access port including a septum exhibiting curvature.

In another aspect of the instant disclosure, a septum may exhibit a curvature that resists deformation in response to a pressure developed within a reservoir of an access port. For example, FIG. 29 shows a septum 120 including a generally concave upper surface 123 and a generally convex lower surface 121. Explaining further, generally concave upper surface 123 and a generally convex lower surface 121 may be exhibited by septum 120 in the absence of external forces (i.e., in an unstressed, equilibrium state). Such a configuration may provide resistance of the septum 120 to deformation due to a pressure developed within reservoir 66 of access port 110, because the upper surface 123 of septum 120 would be forced to flatten (i.e., via deformation of septum 120) before extending beyond the upper surface of housing 60. In other embodiments, a septum may be compressed (e.g., by way of a tenon and mortise coupling or another peripheral coupling configuration between a septum and a housing) so that a curvature of the septum may be reduced or eliminated when the septum is assembled within the housing. However, such a configuration may increase the bulk flexibility or spring constant of the septum. Optionally, a structural element (as described above) may be included within the septum or upon a surface of the septum and may also be fabricated to exhibit concavity or convexity in the absence of external forces. Such a configuration may facilitate a favorable compressive stress field within the septum when coupled to a housing and may enhance resistance of the septum to deformation.

Figure 30:
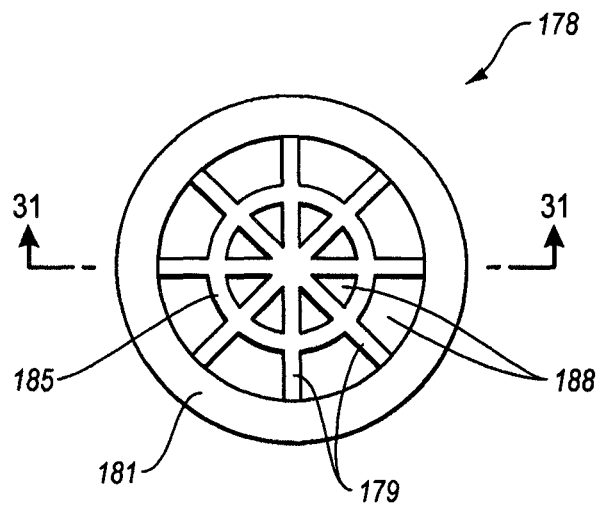
FIG. 30 shows a top elevation view of one embodiment of a septum frame.
Figure 31:
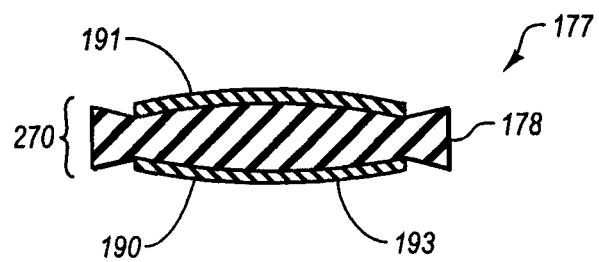
FIG. 31 shows a schematic, side cross-sectional view of one embodiment of a septum including the frame shown in FIG. 30 and another material at least partially surrounding the frame.
Figure 32:
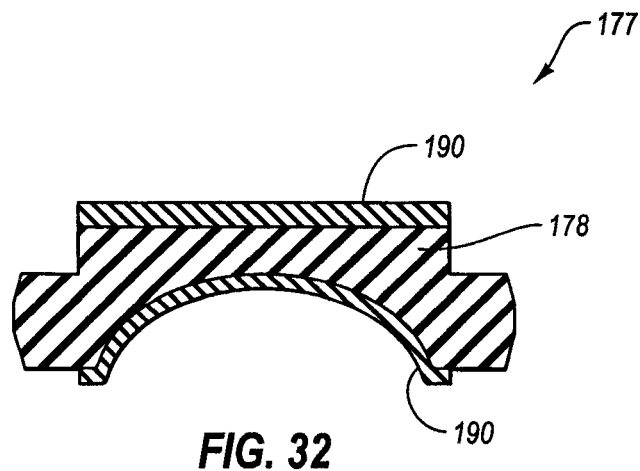
FIG. 32 shows a schematic, side cross-sectional view of another embodiment of a septum including a frame that is at least partially surrounded by another material.
Figure 33:
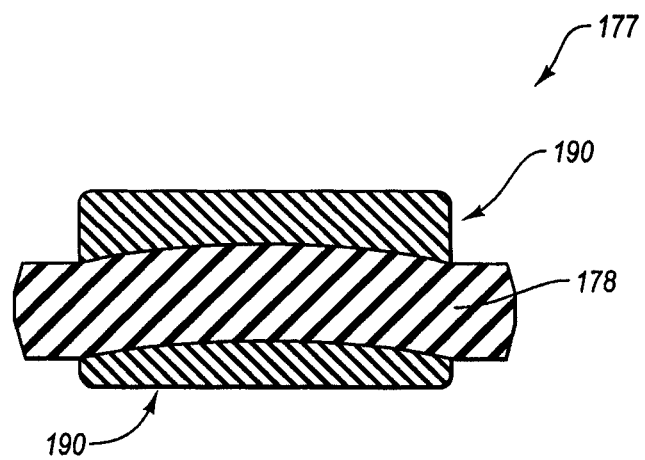
FIG. 33 shows a schematic, side cross-sectional view of yet an additional embodiment of a septum including a frame that is at least partially surrounded by another material.

In a further configuration, a septum may include a structural frame or skeleton and a more pliant material configured to seal punctures created by a cannula. More specifically, a frame may comprise a material with a shore A hardness of at least about 80. Optionally, a frame may include a plurality of whiskers, fibers, or particles to stiffen or strengthen the frame. In one embodiment, nylon fibers, barium sulfate, or the like may be dispersed within a frame. Further, such a frame may be at least partially surrounded by a more pliant material exhibiting a Shore A hardness of about 50 or less (e.g., a Shore A hardness of about 40 to about 50). FIG. 30 shows top elevation view of a frame 178 including a plurality of spokes 179 extending from a generally common origin or region as well as rings 181 and 185. As shown in FIG. 30, spokes 179 in combination with one or both of rings 181 and 185 form apertures 188. According to the instant disclosure, a relatively pliant material configured to seal punctures formed by a cannula passing through the material may at least partially surround such a frame 178. For instance, FIG. 31 shows a schematic side cross-sectional view of septum 177 comprising a frame 178 and another material 190 molded partially about frame 178. Thus, material 190 may substantially surround spokes 179 and may extend within apertures 188. Further, as shown in FIG. 31, ring 181 may form a tenon region 270 for coupling with a housing (as described above) as well as an upper septum surface 191 and a lower septum surface 193. As may be appreciated with reference to shown in FIG. 31, during use, a cannula may pass through a continuous upper layer of material 190 and a continuous lower layer of material 190. Such a configuration may provide suitable sealing capability for septum 177. It will be appreciated that many variations are contemplated by the instant disclosure. For example, FIGS. 32 and 33 show side cross-sectional views of different embodiments of a septum 177 including a frame 178 and another material 190 at least partially surrounding the frame 178. Thus, a frame and a material at least partially surrounding the frame may exhibit arcuate or substantially planar surfaces and may be formed of selected thickness and comprising selected materials (e.g., silicone, etc.).

Figure 34:
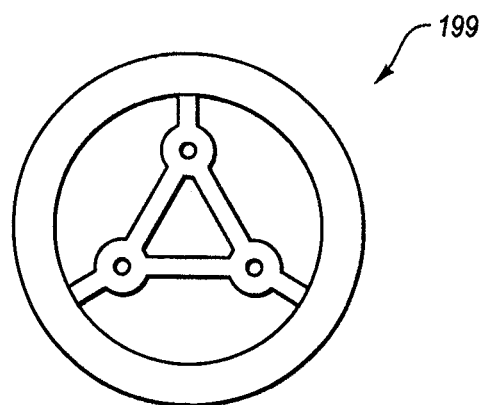
FIGS. 34 and 35 show a respective schematic view of different patterns that may be generated by radiopaque material comprising a septum.
Figure 35:
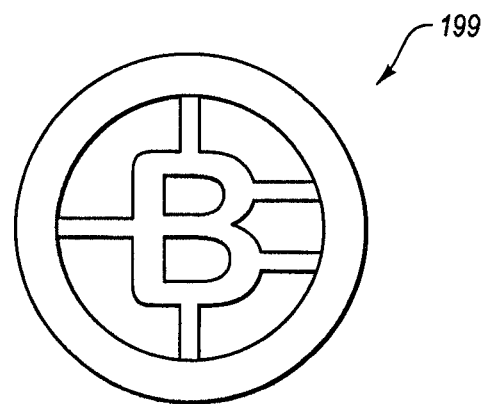

In a further aspect of a septum according to the instant disclosure, a septum may include a radiopaque material and may be configured to form a selected pattern when an x-ray is taken through the septum. For example, FIGS. 34 and 35 show schematic views of patterns 199 that may be generated by correspondingly positioned radiopaque material within a septum. Such a configuration may be useful for identifying the access port as being capable of accommodating particular power injection processes or for locating the septum of an access port.

The instant disclosure further contemplates that any infusion apparatus or device that is used in combination with an access port for infusing fluid at a rate of at least about 1 milliliter per second may be configured accordingly. For example, an infusion set for accessing a vascular access port may include a needle or cannula for puncturing a septum of the access port, a distal end for coupling to an injection apparatus, and tubing (e.g., at least one tubing section) extending between the cannula and the distal end. Generally, any components comprising an infusion set may be configured to withstand a selected flow rate and associated pressure developed by such a selected flow rate.

Figure 36:
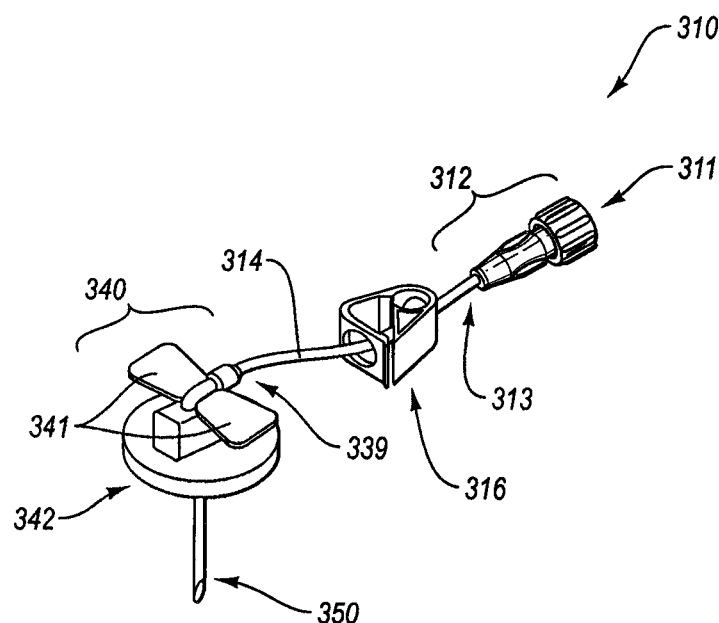
FIG. 36 shows a perspective view of one embodiment of an infusion set according to the instant disclosure.

FIG. 36 shows one embodiment of an infusion set 310 including a base member 340, a cannula 350, a tubing section 314, and connector 312. Tubing 314 may be affixed or otherwise coupled to connector 312 and base 342 generally at joints 313 and 339, respectively. Also, as shown in FIG. 36, a clamp device 316 may be suitably configured for allowing or preventing fluid flow through tubing 314. Further, each of the base member 340, cannula 350, tubing section 314, and end connector 312 may be structured for accommodating a fluid flow rate of at least about 1 milliliter per second through the infusion set 310. In further detail, tubing section 314 may exhibit sufficient strength for withstanding at least about 200 psi without damage. Optionally, tubing section 314 may withstand at least about 300 psi without damage. Further a pressure at which a portion of the infusion set bursts (i.e., a burst pressure of the infusion set 310) may be at least about 400 psi; optionally, such a burst pressure may be at least 600 psi. In one embodiment, tubing section 314 may be substantially optically clear or may be at least partially transparent. In one embodiment, generally, tubing section 314 may comprise a polymer, such as TECOTHANE®. More specifically, tubing section may comprise a polymer, such as TECOTHANE® 55D or a polymer, such as TECOTHANE® 95A. For example, if tubing section 314 has an inner diameter (i.e., a lumen) of about 0.048 inches (±0.003 inches) (i.e., 19 GA), tubing section 314 may comprise a polymer, such as TECOTHANE® 55D. In other examples, if tubing section 314 has an inner diameter (i.e., a lumen) of about 0.041 inches or 0.034 inches (±0.003 inches) (i.e., 20 GA or 22 GA, respectively), tubing section 314 may comprise a polymer, such as TECOTHANE® 95A. Optionally, any polymer, such as TECOTHANE® type material may be at least substantially free of a plasticizer, such as, for instance, Di(2-Ethylhexyl)Phthalate ("DEHP"). In one embodiment, connector 312 may comprise polyvinylchloride ("PVC") and may be, optionally, at least substantially free of plasticizer. The materials disclosed above are merely examples; more generally, tubing section 314, connector 312, base member 340, and cannula 350 may comprise any material (e.g., thermoplastic, polyurethane, metal, etc.) suitable for providing a robust and effective infusion set 310.

During use of the infusion set 310, a mechanical injector may be operably coupled to connector 312 via fastening structure 311. For example, fastening structure may comprise a luer-type connection or any other fluid connection structure. Thus, a fluid may be flowed through the infusion set at a flow rate of at least about 1 milliliter per second via an injection apparatus. As discussed above, a pressure drop through the infusion set 310 may be at least about 100 psi; optionally, a pressure drop through infusion set 310 may be at least about 185 psi.

Figure 37:
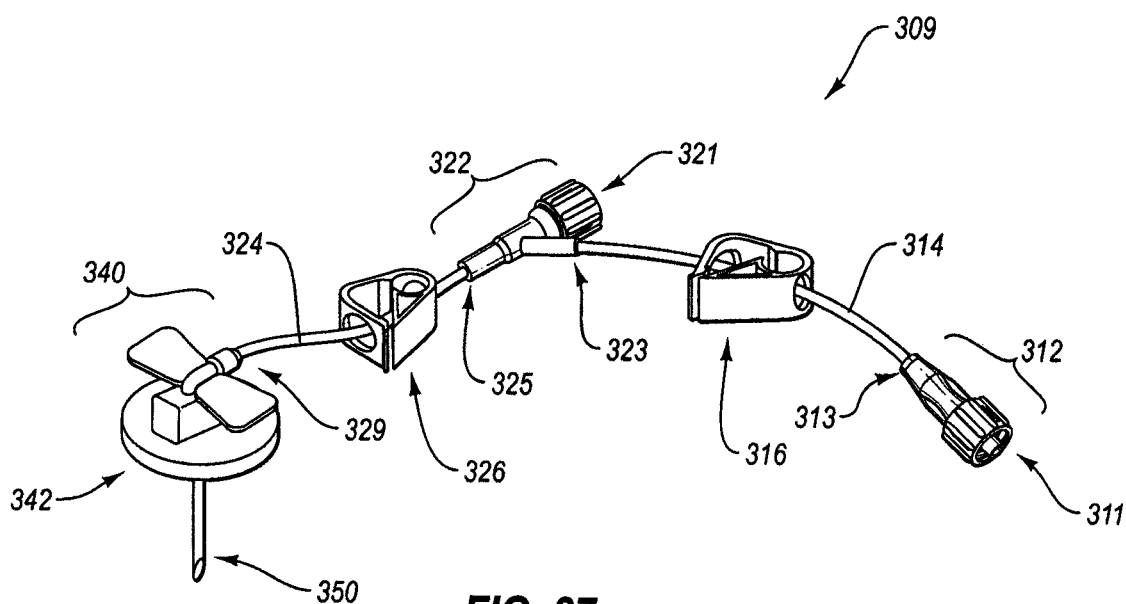
FIG. 37 shows a perspective view of another embodiment of an infusion set according to the instant disclosure.

In another embodiment, an infusion set may include two connectors. In one configuration, one connector may be structured for performing power injection and another connector may be structured for allowing syringe access. For example, FIG. 37 shows an infusion set 309 including a base member 340, a cannula 350, a tubing section 324, an intermediate connector 322, a tubing section 314, and an end connector 312. Tubing 314 may be affixed or otherwise coupled to connector 312 and connector 322 generally at joints 313 and 323, respectively. Similarly, tubing 324 may be affixed or otherwise coupled to connector 322 and base member 340 generally at joints 325 and 329, respectively.

Infusion set 309 may be structured for fluid flow rates and pressures as discussed above in relation to infusion set 310. Accordingly, tubing sections 314 and 324 may comprise materials (e.g., a polymer, such as TECOTHANE® and sizes as discussed above in relation to infusion set 310, without limitation. Similarly, connectors 312 and 322 may comprise any materials (e.g., PVC) discussed above in relation to infusion set 310, without limitation. As shown in FIG. 37, a clamp device 316 may be suitably configured for allowing or preventing fluid flow through tubing 314. Likewise, clamp device 326 may be suitably configured for allowing or preventing fluid flow through tubing 324. In addition, connector 312 may include a fastening structure 311 (e.g., a luer connection, another threaded connection, or any other fastening structure as known in the art) for releasably affixing or coupling the connector 312 to an injection apparatus. Also, connector 322 may include a fastening structure 321 (e.g., a luer connection, another threaded connection, or any other fastening structure as known in the art) for releasably affixing or coupling the connector 322 to an injection apparatus.

Generally, the instant disclosure contemplates that, in one embodiment, connector 312 may be used for power injection, while connector 322 is capped. In another embodiment, a valve mechanism may selectively allow flow through tubing sections 314 and 324 via fluid flow through connector 312, while preventing leakage from connector 322. In addition, if infusion set 309 is not being used for power injection, a cap including a septum may be coupled to connector 322, connector 312, or both. Such a configuration may allow for a syringe to puncture the septum and infuse medication or remove a blood sample. Such a configuration may provide a convenient infusion set with separate connectors for power injection and syringe access, respectively.

In a further aspect contemplated by the instant disclosure, tubing that is used in connection with power injection may be structured for withstanding a selected pressure during use (e.g., power injection) and, optionally, may be configured to resist kinking. Generally, the instant disclosure contemplates that tubing may comprise a plurality of layers. In one embodiment, tubing may comprise a relatively high strength layer and at least one relatively flexible layer. Thus, any layers of tubing may comprise PTFE, polypropylene, polyetheretherketone ("PEEK"), polyimide silicone, fluorinated ethylenepropylene (FEP), perfluoroalkoxy (PFA), ethylenetetrafluoroethylene (ETFE), polyurethane (e.g., thermoplastic polyurethanes, including ISOPLAST®, TECOFLEX®, TECOTHANE®, CARBOTHANE®, TECOPLAST®, or TECOPHILIC® type polyurethanes), or combinations of the foregoing. In one embodiment, the layers may be bonded to one or more adjacent layers. In another embodiment, each of the layers may be movable or slidable relative to one or more adjacent layers.

Figure 39:
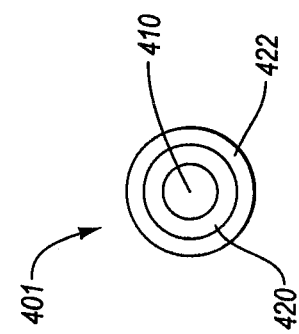
FIGS. 38 and 39 show a side cross-sectional view and an end cross-sectional view of one embodiment of tubing including an inner layer and an outer layer.
Figure 38:
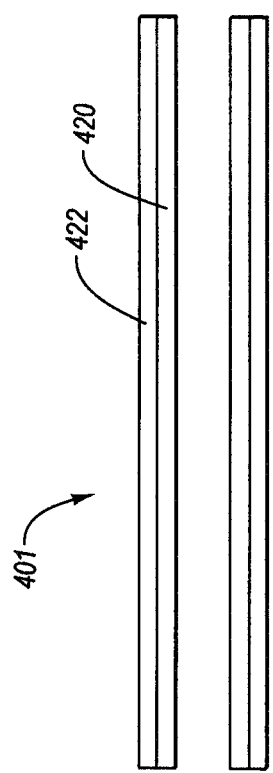

For example, FIGS. 38 and 39 show a side cross-sectional view and an end cross-sectional view of tubing 401 including an inner layer 420 and an outer layer 422. Generally, at least one of inner layer 420 and outer layer 422 may exhibit relatively high strength and the other of inner layer 420 and outer layer 422 may be relatively flexible or vice versa. In one embodiment, inner layer 420 may exhibit relatively high strength and may comprise, for example, PEEK, ULTEM®, polyimide, or the like. Further, outer layer 422 may be relatively flexible and may comprise, for example, FEP, PTFE, PEBAX®, ETFE, silicone or the like. Conversely, outer layer 422 may exhibit relatively high strength and may comprise, for example, PEEK, ULTEM®, polyimide, or the like, while inner layer 420 may be relatively flexible and may comprise, for example, FEP, PTFE, PEBAX®, ETFE, silicone, or the like. Further, optionally, tubing may comprise a first layer exhibiting a modulus of elasticity and at least another layer exhibiting a modulus of elasticity that is less than the modulus of elasticity of the first layer. For example, a relatively high strength material may exhibit a modulus of elasticity of at least about 400,000 psi. Furthermore, a relatively flexible material may exhibit a modulus of elasticity below about 390,000 psi. In another embodiment, at least one of layers 420 and 422 may comprise a composite material (e.g., a composite including particulate or fiber reinforcement). For example, in one embodiment, tubing may comprise polyurethane or PTFE including glass or carbon reinforcing fibers or particles. In one embodiment, each of the layers 420 and 422 may be movable or slidable relative to one or more adjacent layers. Such a configuration may withstand a selected internal pressure without damage to the tubing and may also resist kinking.

In another embodiment, a reinforcing element may be incorporated within at least one of the plurality of layers comprising tubing. For example, FIG. 40 shows a schematic side cross-sectional view of tubing 403 including inner layer 430 and outer layer 432, wherein at least one reinforcing element 434 is incorporated within outer layer 432. Optionally, at least one reinforcing element 434 may be incorporated within any layer or layers of a plurality of layers comprising tubing, without limitation. As shown in FIG. 40, reinforcing element 434 may comprise a coil, in one embodiment. One of ordinary skill in the art will appreciate that many variations are possible, for example, at least one reinforcing element may comprise a mesh (e.g., a wire mesh, a fabric, a fiber mesh, etc.). In another embodiment, at least one reinforcing member may comprise one or more elongated members extending longitudinally within at least one layer comprising tubing (e.g., aligned with the direction of extension of the tubing). In another embodiment, at least one reinforcing member may comprise one or more rings. Such a configuration may provide radial stiffness, strength, or both to a tubing section.

Referring to FIG. 40, in one embodiment, inner layer 430 may exhibit relatively high strength and may comprise, for example, PEEK or polyimide. Further, outer layer 432 may be relatively flexible and may comprise, for example, FEP, PTFE, ETFE, silicone, or polyurethane. Further, layers 430 and 432 may have a thickness (e.g., a radial thickness) of between about 0.005 inches and about 0.001 inches. As mentioned above, layers 430 and 432 may be bonded to one another or may be movable (slidable, twistable, etc.) with respect to one another. Optionally, a coating 433 may be applied to at least a portion of exterior surface of layer 432. Such a coating 433, in one embodiment, may comprise a polymer, such as TEFLON® and may have a thickness of between about 0.001 inches and about 0.002 inches.

In a further embodiment, FIG. 41 shows a schematic side cross-sectional view of tubing 405, including inner layer 440 and outer layer 442, wherein at least one reinforcing element 444 is incorporated within inner layer 440. As shown in FIG. 41, reinforcing element 444 may comprise a coil, in one embodiment. In other embodiments, reinforcing element may comprise any structure discussed above in relation to reinforcing element 434, without limitation. In addition, in one embodiment, inner layer 440 may be relatively flexible and may comprise, for example, FEP, PTFE, ETFE, or polyurethane. Further, outer layer 442 may exhibit relatively high strength and may comprise, for example, PEEK or polyimide. Further, layers 430 and 432 may have a thickness (e.g., a radial thickness) of between about 0.005 inches and about 0.010 inches. Optionally, a coating 443 may be applied to at least a portion of exterior surface of layer 442. Such a coating 443, in one embodiment, may comprise a polymer, such as TEFLON® and may have a thickness of between about 0.001 inches and about 0.002 inches.

Figure 43:
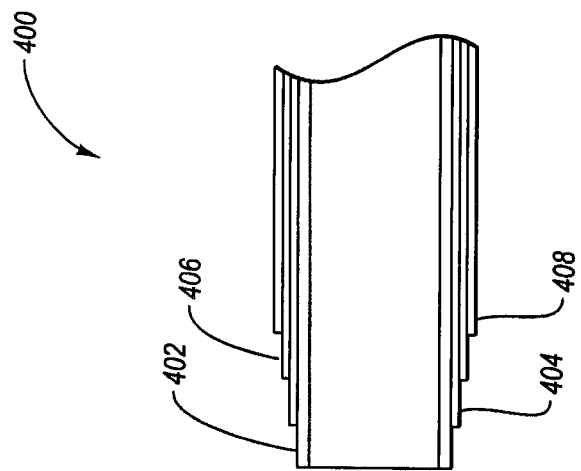
FIGS. 42 and 43 show an end cross-sectional view and a schematic, side cross-sectional view, respectively, of tubing including four layers.
Figure 42:
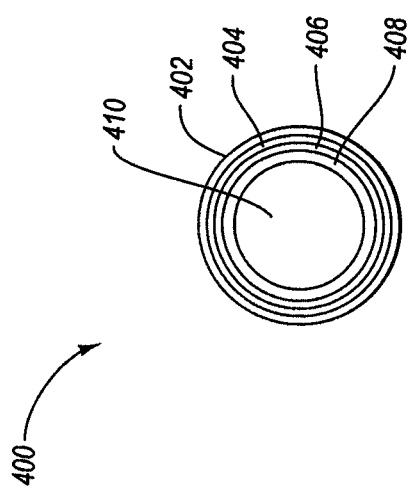

In an additional embodiment, tubing may include four layers. For example, FIGS. 42 and 43 show a cross-sectional end view and a side cross-sectional view of another embodiment of tubing 400. More particularly, as shown in FIGS. 42 and 43, tubing 400 includes layers 402, 404, 406, and 408. As shown in FIG. 42, layer 402 defines a lumen 410. In one embodiment, lumen 410 may have a substantially circular cross-sectional shape and may exhibit a diameter of about 0.024 inches. In another embodiment, each of the layers 402, 404, 406, and 408 may be movable or slidable relative to one or more adjacent layers. In addition, layer 402 may comprise a material exhibiting a relatively high tensile strength. Such a configuration may withstand relatively high pressures within lumen 410. For example, layer 402 may comprise PEEK, polyimide, etc. Typically, such relatively high strength materials may exhibit a modulus of elasticity of at least about 400,000 psi. Furthermore, each of layers 404, 406, and 408 may comprise a material that is relatively flexible. Such layers 404, 406, and 408 may each exhibit a tensile strength that is less than the tensile strength of layer 402. For example, each of layers 404, 406, and 408 may comprise a fluoropolymer, PEBAX®, polyethylene terephthalate ("PET"), silicone, etc. Typically, such relatively flexible materials may exhibit a modulus of elasticity below about 390,000 psi. However, any layers may comprise PTFE, polypropylene, silicone, FEP, PFA, ETFE, polyurethane (e.g., thermoplastic polyurethanes, including ISOPLAST®, TECOFLEX®, TECOTHANE®, CARBOTHANE®, TECOPLAST®, or TECOPHILIC® type polyurethanes), or combinations of the foregoing, without limitation.

Figure 44:
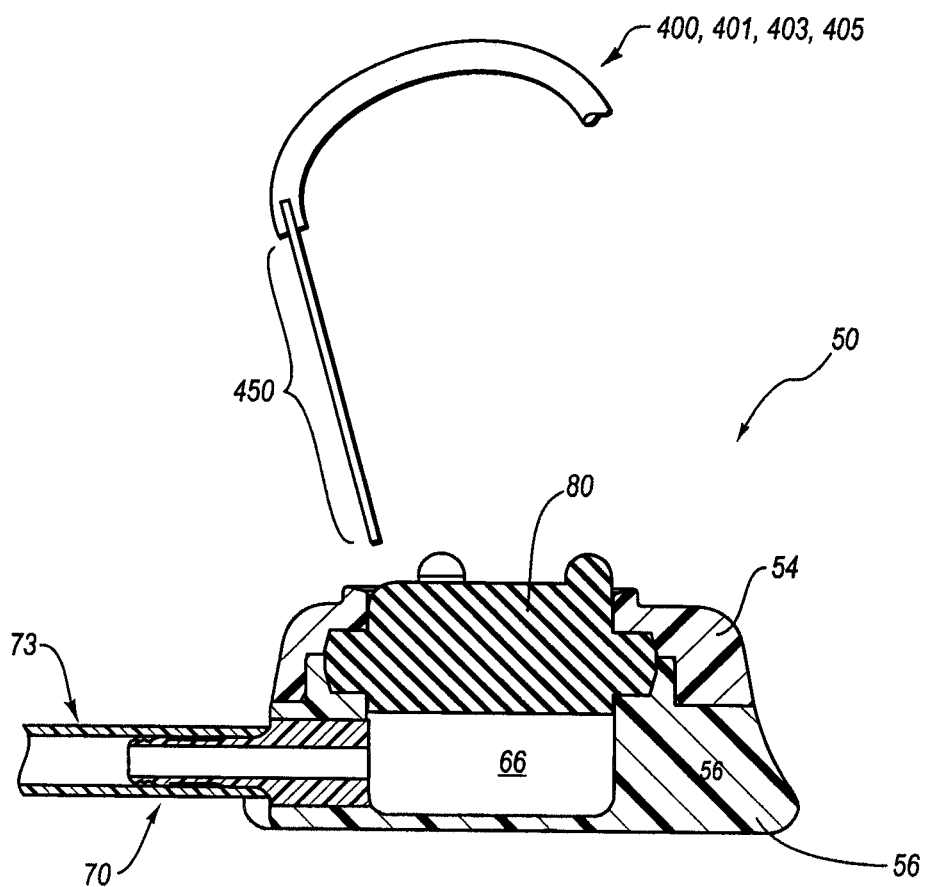
FIGS. 44 and 45 show schematic, side cross-sectional views of a tubing section including a plurality of layers, wherein at least one layer of the plurality of layers extends from a distal end of the tubing to form a slender hollow region for insertion through a septum of an access port.
Figure 45:
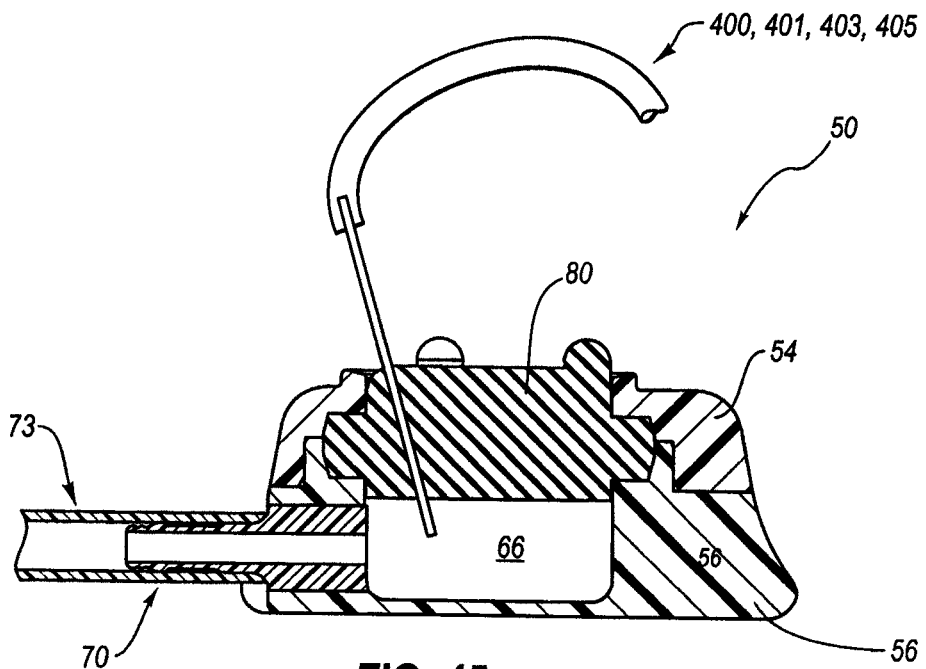

In a further aspect of the instant disclosure, at least one layer comprising a tubing section may extend distally from a slender hollow structure for accessing a reservoir of an access port through a septum. Put another way, at least one layer may extend from a tubing section and may be structured for puncturing a septum of an access port. For instance, FIGS. 44 and 45 show a schematic side cross-sectional view of tubing 400, 401, 403, 405, and an access port 50. Tubing 400, 401, 403, 405 (as described above) includes a slender hollow region 450. Further, slender hollow region 450 may be relatively stiff and suited for penetrating a septum 80 of an access port 50, as shown in FIG. 45. Thus, a slender hollow region 450 extending from a distal end of tubing 400, 401, 403, 405 (which comprises a plurality of layers) may form a needle or cannula for fluid communication between a lumen of tubing 400, 401, 403, 405, and a reservoir 66 of access port 50. More particularly, a slender hollow region 450 may comprise one or more layers exhibiting a relatively high strength of relatively high-strength layers (e.g., PEEK) forming tubing 400, 401, 403, 405. In one embodiment, an innermost layer of tubing 400, 401, 403, 405 may form slender hollow region 450. Such a configuration may be advantageous and may, for example, reduce the complexity of manufacturing an infusion set.

Many different embodiments of vascular access apparatuses or infusion systems may incorporate one or more aspects of the instant disclosure. Some embodiments of a vascular access apparatuses or infusion systems are disclosed in U.S. Patent Application No. 60/675,309, filed Apr. 27, 2005, the disclosure of which is incorporated, in its entirety, by this reference. Any of the infusion systems, apparatuses, or methods, taken alone or in combination, described in U.S. Patent Application No. 60/675,309, may be structured or otherwise suited for performing power injection (e.g., accommodating a fluid flow rate of at least about 1 milliliter per second, without limitation).

For example, the instant disclosure contemplates that an infusion system configured for establishing fluid communication between a flexible tube and a reservoir of an access port may be structured for power injection. Such an infusion system may include a slender pointed element that facilitates placement of the flexible tube through a septum of the access port and is removable from the infusion system once the flexible tube is appropriately positioned.

Figure 46:
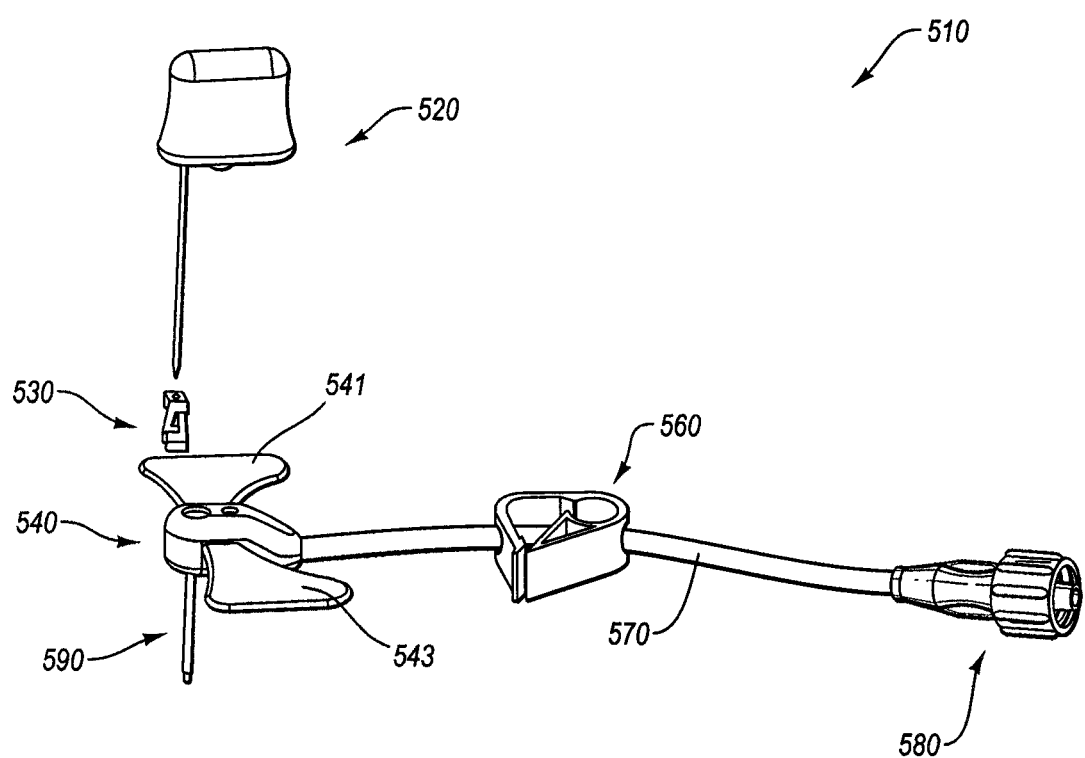
FIG. 46 shows a perspective view of one embodiment of an infusion system configured for inserting a flexible catheter through a septum of an access port.
Figure 47:
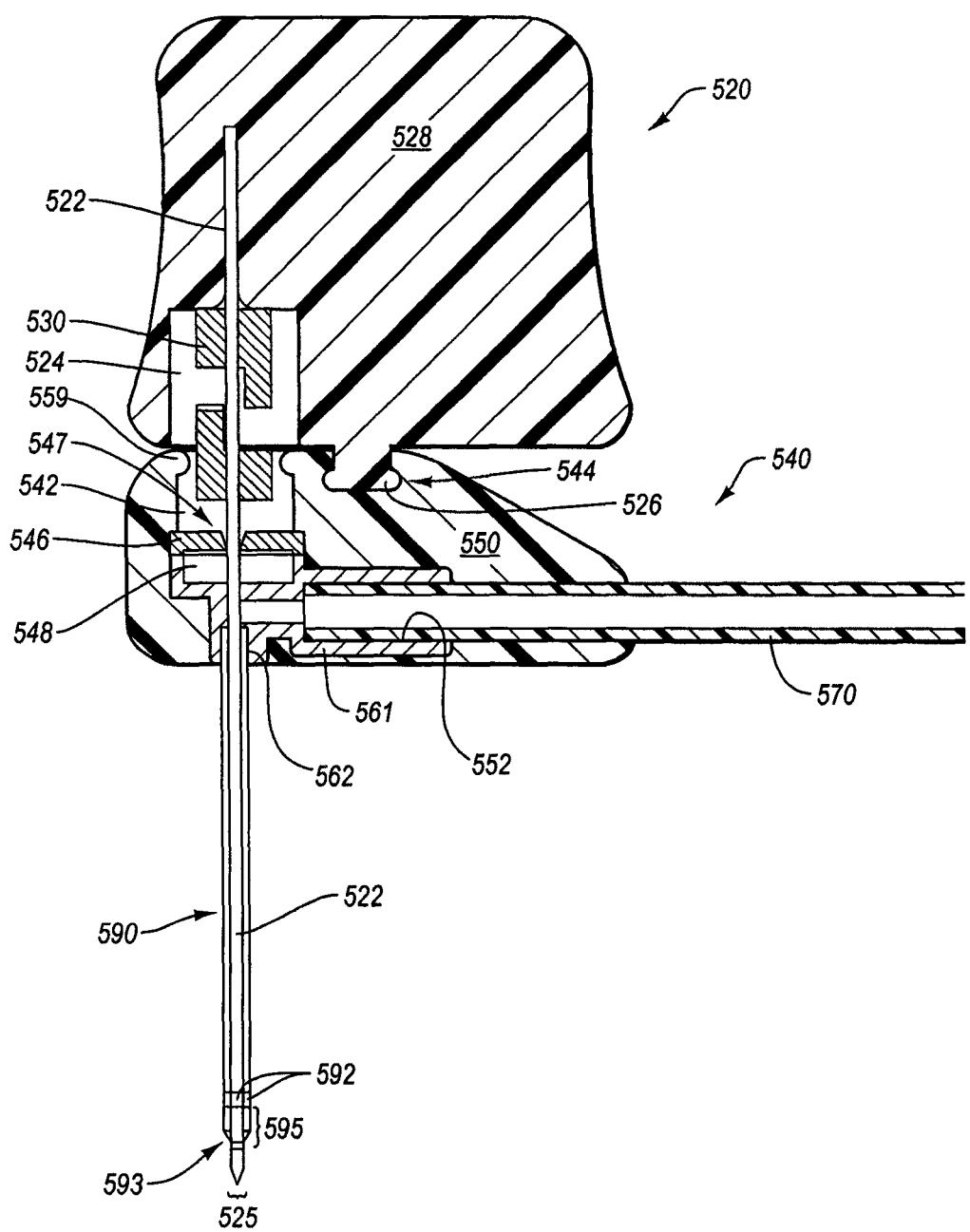
FIG. 47 shows a schematic, partial, side cross-sectional view of the infusion system shown in FIG. 46.

Particularly, FIG. 46 shows in one embodiment an infusion system 510 in an exploded assembly view, including an insertion assembly 520, a safety clip 530, a hub 540 flexible tubing 590, extension tube 570, clamp device 560, and tube connector 580. In further detail, FIG. 47 shows a partial side cross-sectional view of infusion system 510. As shown in FIG. 47, insertion assembly 520 comprises a base 528 and a slender pointed element 522 (e.g., a needle, a trocar, or a cannula) secured thereto. As shown in FIG. 47, slender pointed element 522 includes a pointed end 525. In a particular embodiment, the instant disclosure may utilize a slender pointed element having a "non-coring" pointed end (i.e., pointed end 525 is not "open" or hollow) to avoid damaging a septum of a port into which the slender pointed element is inserted. The slender pointed element 522 may comprise any conventional needle, trocar, or cannula material, such as a stainless steel (e.g., AISI 304 stainless steel), or may, in another embodiment, comprise a relatively hard plastic. In one embodiment, base 528 may be injection molded or otherwise formed about slender pointed element 522 to capture a portion of the slender pointed element within the base 528, as best seen in FIG. 47. Further, base 528 may optionally include a recess 524 structured for accommodating other mechanisms (e.g., safety clip 530), if such a recess is desirable. Base 528 may also, optionally, include a coupling feature 526 (e.g., a protrusion) structured for coupling to a coupling feature 544 (e.g., a recess) formed in hub 540. Hub 540, as shown in FIG. 47, may generally include hub body 550, manifold element 561, septum 548 and cap 546. In one embodiment, hub body 550 may comprise TECOFLEX® (e.g., such as TECOFLEX® 85A-B20). Further, hub body 550 may define wing structures 541 and 543 (FIG. 46), which may be configured for affixing the hub to skin of a patient (e.g., by taping wing structures 541 and 543 to a patient, adhesively affixing wing structures 541 and 543 to a patient, or otherwise affixing wing structures 541 and 543 to a patient). Wing structures 541 and 543 may be employed for manipulation of the hub, such as, for example, when inserting the slender pointed element 522 and flexible catheter 590 into an implanted port or when removing the slender pointed element 522 from an implanted port. Hub body 550 may optionally include a recess 542, if such a recess is desirable. As shown in FIG. 47, recess 542 may have a retaining lip 559 for retaining safety clip 530 therein, while long slender element 522 is positioned through the safety clip, as discussed in further detail hereinbelow.

Hub 540 may be structured for allowing the slender pointed element 522 of insertion assembly 520 to pass through the hub 540 and through septum 548, which is positioned within the hub 540. Put another way, manifold element 561 may define a plurality of passageways and at least one septum 548 through which fluid communication with the plurality of passageways may be accomplished.

Explaining further, a manifold element 561 may be configured for housing septum 548 to provide a seal a port or opening of a plenum defined by manifold element 561. Optionally, a cap element 546 may be positioned to capture septum 548 between cap element 546 and manifold element 561. Cap 546 may include an aperture 547 for allowing a slender pointed element to pass therethrough and through septum 548. Thus, slender pointed element 522 (e.g., an appropriately sized trocar, non-coring needle, or non-coring cannula) may be inserted through and removed from septum 548 without compromising the ability of septum 548 to seal. Further, the presence of cap 546 may allow for so-called "power injection" to occur via manifold element 561, wherein pressures within manifold element 561, tubing 570, and flexible catheter 590 may reach at least about 200 psi or higher. Septum 548 may be structured according to any septum embodiments disclosed herein (e.g., including at least one structured element, for performing power injection, etc.), without limitation.

As shown in FIG. 47, flexible catheter 590 may be affixed to manifold element 561 and extension tube 570 may be affixed to manifold element 561. In one example, extension tube 570 and flexible catheter 590 may be chemically bonded to manifold element 561. In another example, an adhesive may affix extension tube 570 to surface 552 a part of manifold element 561. Similarly, an adhesive may affix flexible catheter 590 to inner surface 562 another port of manifold element 561. Further, the hub body 550 may be formed (e.g., injection molded, cured, or otherwise over-molded) over the manifold element 561 (and, optionally the septum 548, the cap 546, or both) and at least a portion of the extension tube 570 as shown in FIG. 47. In another embodiment, the hub body 550 may be formed over at least a portion of the flexible catheter 590, if desired.

Generally, as mentioned above, any tubing disclosed in the instant disclosure may comprise a portion of infusion system 510. Further, tubing clamps and connection devices as known in the art, may be employed for extension tubing 570, clamp device 560, and tube connector 580.

Flexible catheter 590 may comprise any material that is suitable for power injection. For example, in one embodiment, flexible catheter 590 may comprise a polymer, such as TECOTHANE® (e.g., TECOTHANE® TT1055 D). As shown in FIG. 47, flexible catheter 590 may include an elongated lumen therein. Further, flexible catheter 590 may have, proximate to opening 593 thereof, a transition region 595 wherein a cross-sectional size (transverse to the lumen 594) of the flexible catheter 590 increases as a function of increasing distance from opening 593. Optionally, transition region 595 may include two distinct tapers, although the instant disclosure contemplates more generally that at least one taper, at least one arcuate surface, or combinations thereof may define transition region 595. Generally, at least one aperture (e.g., one or more than one) may be provided proximate opening 593 that extends through the tubular body of flexible catheter 590 and communicates with lumen 594. As shown in FIG. 47, flexible catheter 590 may include two apertures 592 in fluid communication with lumen 594.

As shown in FIG. 47, slender pointed element 522 may extend through safety clip 530, through aperture 547 of cap 546, and into flexible catheter 590. Slender pointed element 522 may be structured for allowing fluid communication within flexible catheter 590. More particularly, slender pointed element 522 may be sized so as to allow for clearance between the exterior of the slender pointed element 522 and the interior (i.e., the lumen) of the flexible catheter 590. In one embodiment, slender pointed element 522 may include at least one longitudinally extending indentation (with respect to a nominal cross-sectional shape of the slender pointed element 522). For example, slender pointed element 522 may have a pointed end 525 and may include longitudinally extending indentations extending along (i.e., along a longitudinal axis of) slender pointed element 522. In another embodiment, slender pointed element 522 may be generally circular, and longitudinally extending indentations may form a substantially triangular cross section of the slender pointed element 522 over the portion of the slender pointed element that they are formed.

Figure 48:
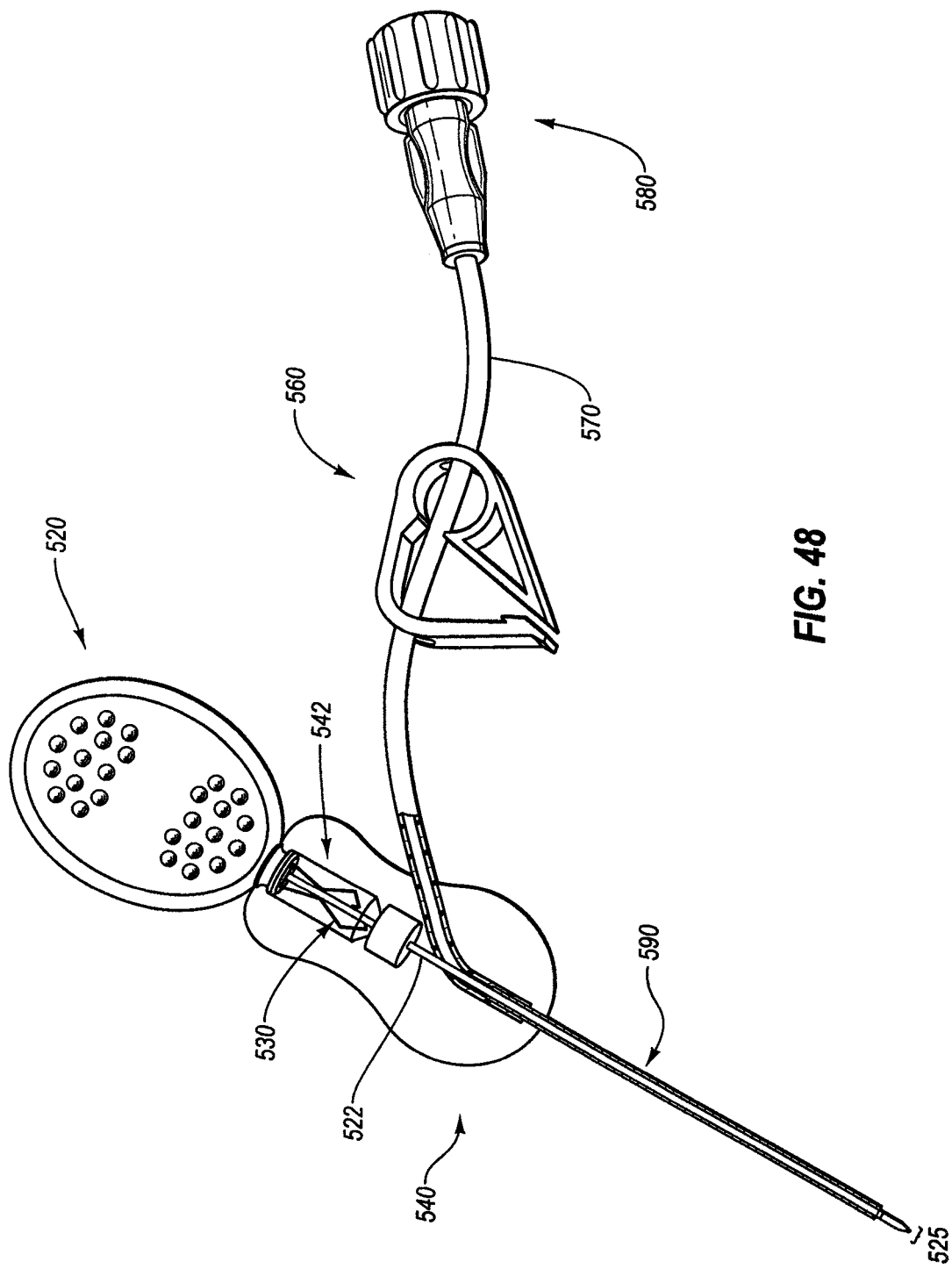
FIG. 48 shows a perspective view of another embodiment of an infusion system configured for inserting a flexible catheter through a septum of an access port.
Figure 49:
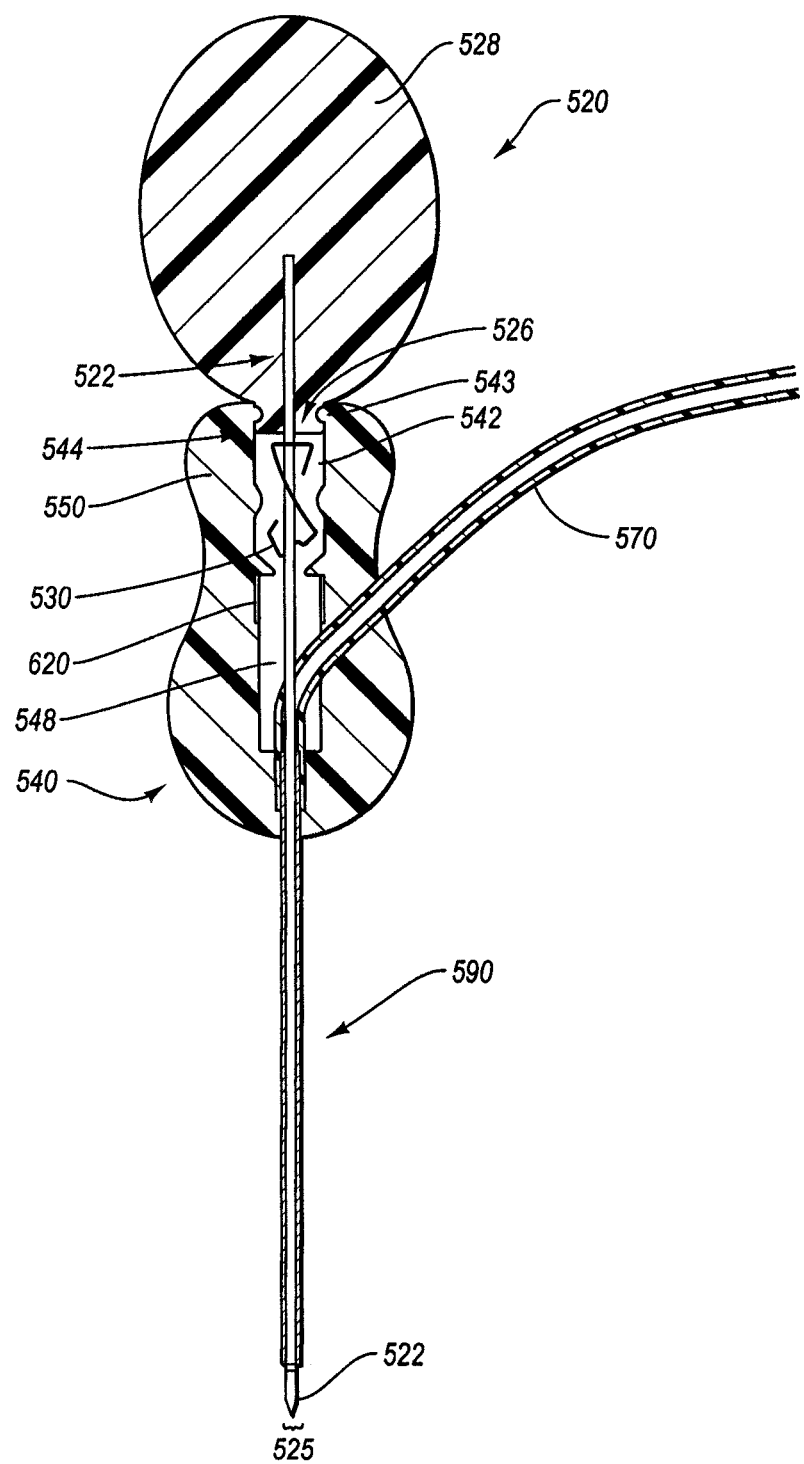
FIG. 49 shows a schematic, partial, side cross-sectional view of the infusion system shown in FIG. 48.

In a further embodiment, an infusion system may be structured so that a slender pointed element passes through an extension tube, a flexible catheter, or both. Explaining further, appropriate placement and configuration of a septum may allow for a slender pointed element to pierce or pass into an extension tube, a flexible catheter, or both. FIGS. 48 and 49 show another embodiment of a hub 540 including recess 542, sleeve 620, and septum 548. In addition, at least a portion of each of extension tube 570 and flexible catheter 590 may extend partially within hub body 550. Further, flexible catheter 590 extends partially within extension tube 570. Put another way, flexible catheter 590 may at least partially overlap with extension tube 570 and vice versa. In another embodiment, a single tubular element may extend through hub 540 and function as both the flexible catheter 590 and extension tube 570, if desired. Further, optionally, septum 548 may at least partially surround a portion of extension tubing 570. Such a configuration may facilitate sealing of septum 548 upon removal of slender pointed element 522 therefrom. Sleeve 620 may compress septum 548 so as to facilitate sealing of septum 548 upon removal of slender pointed element 522 from the region of the septum 620 that the sleeve 620 surrounds. Septum 548 may be structured according to any septum embodiments disclosed herein (e.g., including at least one structured element, etc.) for performing power injection, without limitation.

Figure 50:
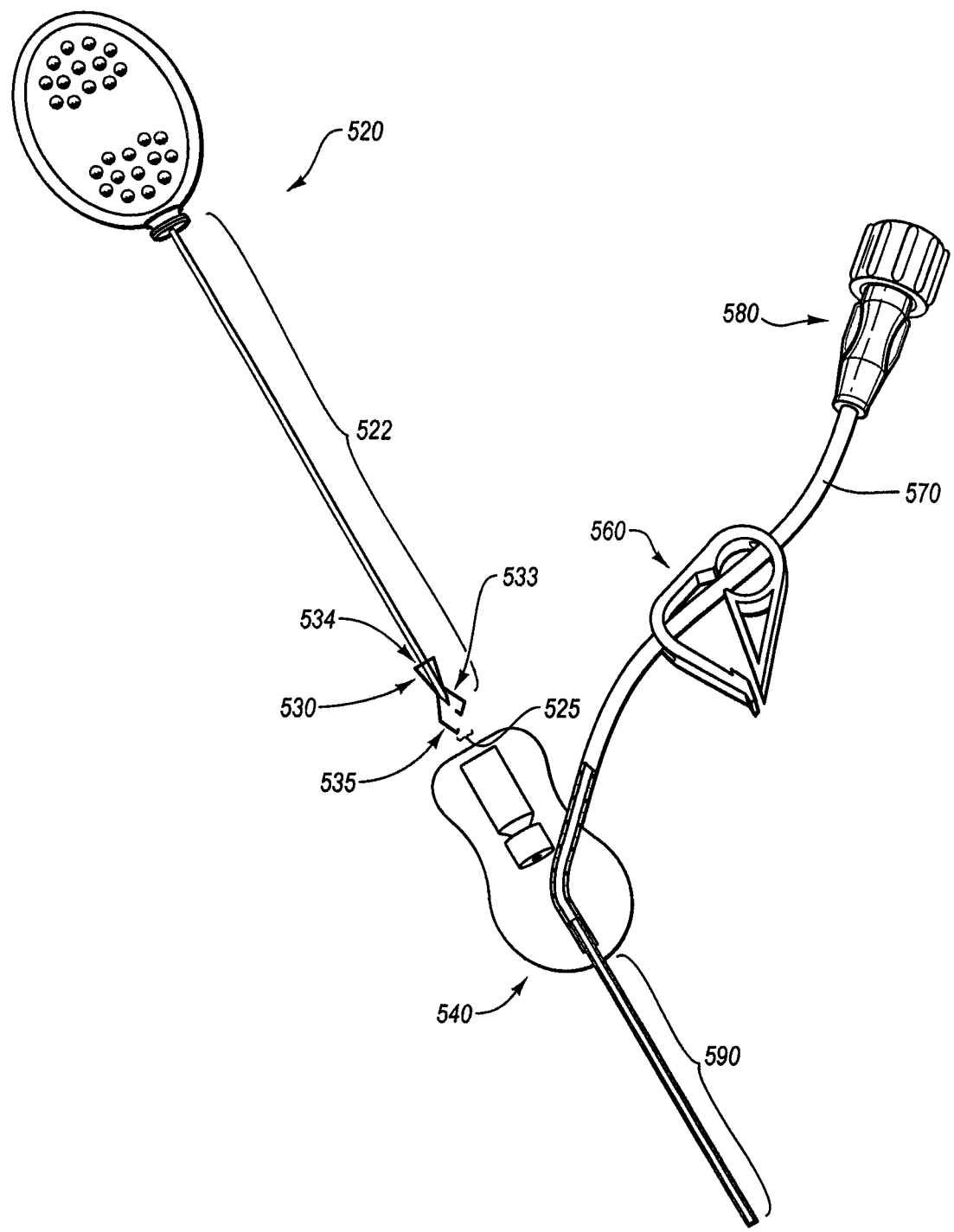
FIG. 50 shows a perspective view of the infusion system shown in FIG. 48, wherein the insertion assembly is removed from the hub.

Further, FIG. 50 shows a perspective view of safety clip 530 positioned generally about pointed end 525 of slender pointed element 522. Safety clip 530 includes legs 533 and 535 each having a curved end region, respectively, and a hole 534 sized for passing there through slender pointed element 522. In further detail, initially slender pointed element 522 may be passed through hole 534 and between legs 533 and 535 may be positioned and configured so as to allow the slender pointed element 522 to extend there past. Further, when the slender pointed 522 element is positioned therein and safety clip 530 is positioned within recess 542, safety clip 530 may be sized so that it will fit within the retaining lip 543 (FIG. 49) of recess 542 (FIG. 49). However, legs 533 and 535 may be biased so that if the pointed end 525 of the slender pointed element 522 is moved toward hole 534 and does not extend past the curved end regions of the legs 533 and 535, legs 533 and 535 will move toward one another to effectively capture the pointed end 525 of the slender pointed element 522. Safety clip 530 may comprise any self-actuating device for capturing a pointed end 525 of a slender pointed element 522. Such a safety clip 530 may reduce the chance of inadvertent insertion of the slender pointed element 522 into another person, particularly the medical practitioner that is installing and removing the slender pointed element 522.

The instant disclosure further recognizes that because the consequences of improperly pressurizing an access port (and a catheter affixed to the access port, if any) or an infusion set may be problematic, it may be advantageous to provide at least one identification attribute to components of an infusion system so that all of such components may be suitable for withstanding an anticipated maximum flow rate and pressure associated with a selected infusion process. Put another way, an access port that is configured for accommodating a flow rate of at least about 1 milliliter per second may include at least one identification attribute. Such an at least one identification attribute may be observed (e.g., visually, by palpation, ultrasonically, radiographically, etc.) or otherwise detected. The term, "identification," as used herein and in connection with any infusion devices (an access port, infusion set, etc.), means the ability to correlate selected information of interest with a perceivable feature.

The instant disclosure contemplates that any of the identification features or attributes, taken alone or in combination, described in U.S. Patent Application No. 60/658,518, filed 4 Mar. 2005, may identify an access port as being structured for power injection. Also, embodiments of an access port including at least one identification attribute are disclosed in U.S. Pat. No. 8,177,762, filed 28 Dec. 2005, the disclosure of which is incorporated, in its entirety, by this reference. The instant disclosure contemplates that any of the identification features or attributes, taken alone or in combination, described in U.S. Pat. No. 8,177,762 may identify an access port as being structured for power injection. Further, an access port may be identified by a maximum rate at which fluid may safely be infused. For example, at least one identification attribute may indicate that an access port is configured for accommodating a fluid flow rate of at least about 1 milliliter per second, without limitation.

Referring to an access port encompassed by the instant disclosure, at least one attribute of a housing of an access port may provide at least one identification attribute for identifying the access port as being structured for power injection at a rate of at least about 1 milliliter per second. In one embodiment, at least one physical attribute (e.g., size, shape, etc.) of an access port may identify the access port as suitable for power injection or may identify a maximum flow rate or pressure that may be safely accommodated by the access port.

Thus, one aspect of the instant disclosure relates to a method of identifying an access port (e.g., subcutaneously implanted or otherwise situated, without limitation) as being suited for power injection. More particularly, an access port including a septum may be provided. Further, at least one attribute of the access port may be perceived. In addition, the subcutaneously implanted access port may be identified as being suitable for power injection in response to perceiving the at least one attribute of the access port.

Figure 51:
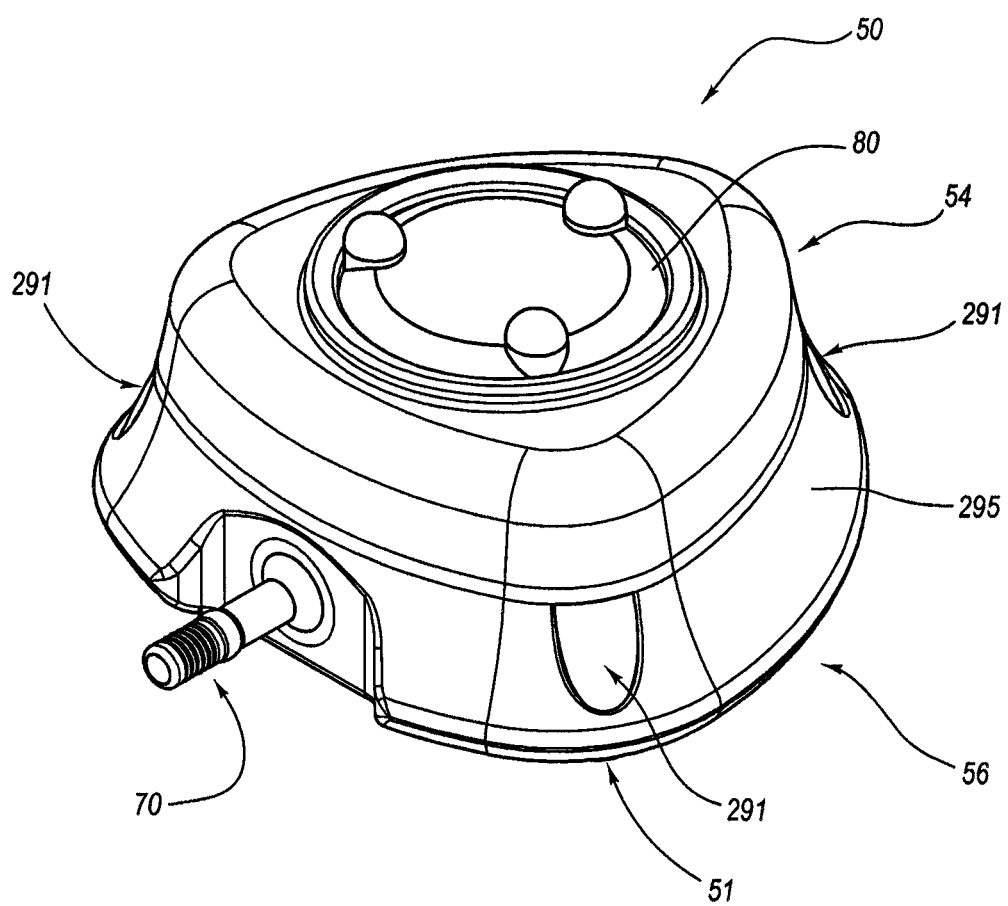
FIG. 51 shows a perspective view of one embodiment of an access port according to the instant disclosure.
Figure 52:
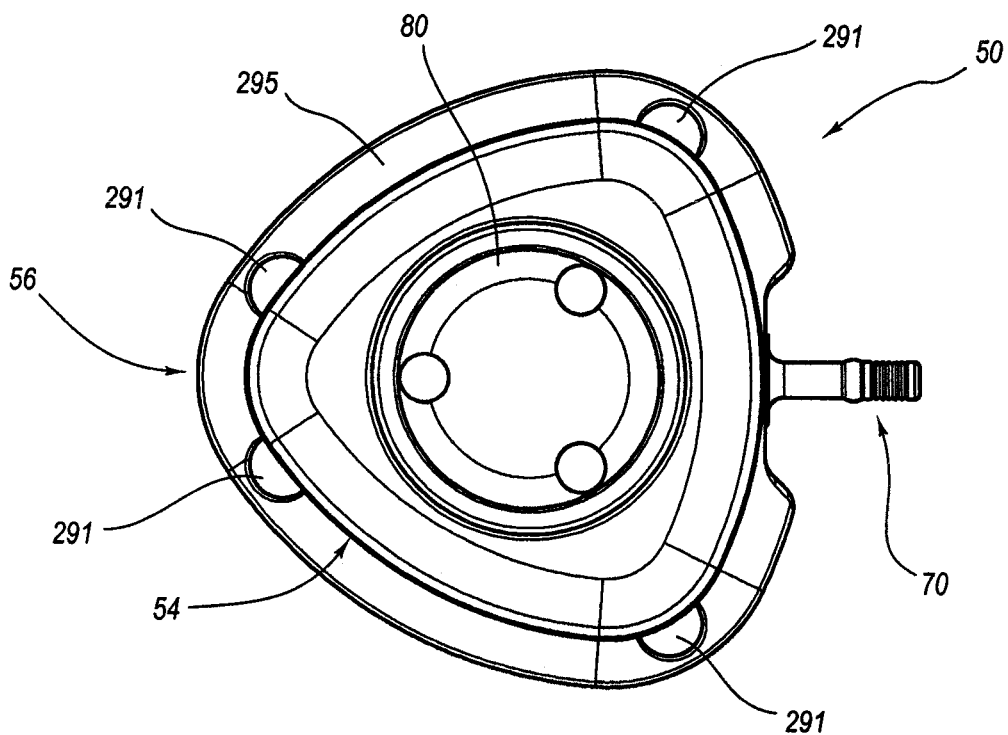
FIG. 52 shows a top elevation view of the access port shown in FIG. 51.
Figure 53:
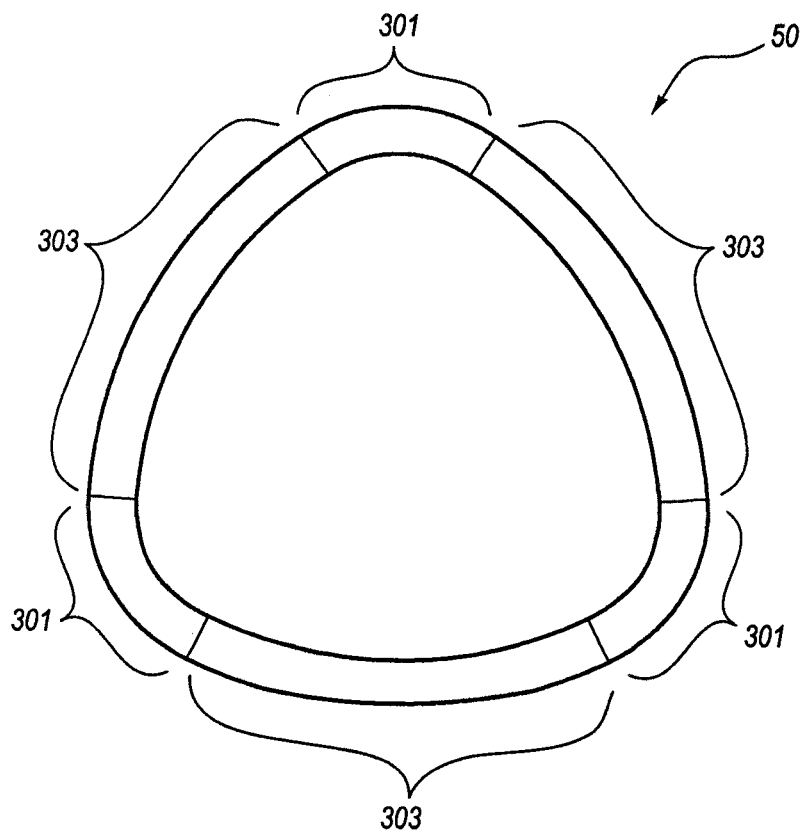
FIG. 53 shows a simplified representation of a transverse cross-section of the access port shown in FIGS. 51 and 52.

In one embodiment, at least one attribute for identification may comprise at least one feature of an access port housing. In further detail, FIG. 51 shows a perspective view of an assembled access port 50. As shown in FIG. 51, a side periphery 295 (e.g., one or more side walls and, optionally, exposed surfaces of suture plugs 291) of access port 50 may be generally triangular. Thus, cap 54 and base 56 may collectively form a generally triangular housing 60 of access port 50. Also, the instant disclosure contemplates that side periphery 295 may taper or arcuately extend between an upper surface 61 of cap 54 and lower surface 51 of base 56. As shown in FIG. 51, a transverse cross section (taken in a selected plane substantially parallel to lower surface 51, if planar, of base 56) of access port 50 may be larger proximate to lower surface 51 of base 56 and may be relatively smaller proximate to an upper surface of cap 54. FIG. 52 shows a top elevation view of the access port 50 shown in FIG. 52 and illustrates a generally triangular shape defined by side periphery 295. Additionally, FIG. 53 shows a simplified representation of a transverse cross section of access port 50. As shown in FIG. 53, side periphery 295 of access port 50 may define three side regions 303 that extend between associated vertex regions 301. In addition, in one embodiment and as shown in FIG. 53, side periphery 295 may define a substantially equilateral generally triangular shape. As may be appreciated, side regions 303 may arcuately extend between associated vertex regions 301; thus, side regions 303 may form "sides" of a generally triangular shape. Further, although vertex regions 301 are rounded, it will be appreciated that such vertex regions 301 form an intersection between adjacent side regions 303. Accordingly, it will be appreciated that the phrase "generally triangular," as used herein, encompasses any generally three-sided geometry wherein adjacent sides intersect at or within vertex regions, without limitation. For example, "generally triangular" encompasses three-sided polygons, circular triangles, equilateral triangles, etc., without limitation.

Furthermore, in a further embodiment, at least one attribute for identification may comprise a radiographic marker. More particularly, an access port may exhibit an observable pattern, symbol, marker, or other indicium that indicates that the access port is structured for accommodating a particular flow rate, pressure, or both. In another embodiment, at least one attribute for identification may comprise a perceptible aspect, such as a visually perceivable feature. For example, at least one color, at least one symbol, at least one typographical character (e.g., a letter, a number, etc.), a pattern, or any other indicium that may be visually perceivable or otherwise perceptible may be used. In a yet additional embodiment, an ultrasound detectable feature may be incorporated within an access port. In a further additional embodiment, an access port may comprise an RFID tag.

It will be appreciated that other equipment and devices (e.g., infusion sets, tubing, injectors, etc.) may be identifiable in relation to a suitable maximum flow rate or maximum pressure. For example, particular infusion apparatuses may include one or more of the above-mentioned identification attributes or features. Such a configuration may allow for different components (e.g., tubing, needles, access ports, mechanical injectors, etc.) to be matched with one another. For example, substantially similar or matching identification attributes shared by a power injection apparatus, an infusion set, and an access port may indicate suitability for use with one another to perform a selected power injection process.

Another aspect of identification of an access port may relate to identification of a patient within which an access port is implanted. More specifically, a patient may be provided with an identification card that carries perceptible (e.g., visually, via magnetic strip, bar code, manually, or by other suitable mechanisms) information regarding an implanted port. Thus, such an identification card may be presented to a health care worker, the information carried by the identification card may be perceived, and the access port may be identified. Upon identifying the access port, characteristics of the access port may be ascertained, such as, for instance, a maximum flow rate, a maximum pressure, suitability for a particular procedure or procedures, etc. In another embodiment, a wristband or bracelet may be provided to a patient within whom an access port is implanted. In a further embodiment, a key chain including an information carrying device, such as, for example, a magnetic strip, a bar code, a computer readable media or device (e.g., a compact disk, "flash" memory, a disk drive, etc.), or any other suitable information carrying device. In another embodiment, a sticker containing the port information can be applied to the chart of the patient. In further embodiments, labeling on the infusion set can be used to identify the set as power injection compatible.

A further aspect of the instant disclosure relates to a septum comprising a gel or viscous liquid. The term "gel," as used herein, means a colloid with at least one solid component suspended within at least one liquid component, wherein the solid particles (e.g., polymer particles) are attracted or otherwise linked to one another (e.g., entangled or cross-linked) by covalent, ionic, or dispersion (physical) forces. Thus, in one embodiment, a gel may be a colloid in which the solid disperse phase forms a network in combination with the fluid continuous phase to produce a viscous or semi-rigid sol. A gel may exhibit stress-strain behavior that is elastic, viscoelastic, or plastic, without limitation. The term "viscous liquid," as used herein, means a liquid exhibiting a viscosity of about 20,000 centipoises or higher.

One or more passageways formed through a septum positioned within a housing to form an access port may allow for leaking of fluid through the one or more passageways if the reservoir of the access port is pressurized. The instant disclosure contemplates that a gel region may be generally positioned between an upper surface of a septum and a lower surface of a septum, to facilitate a cannula extending through the septum from the upper surface to the lower surface to also pass through at least a portion of the gel region.

Figure 54:
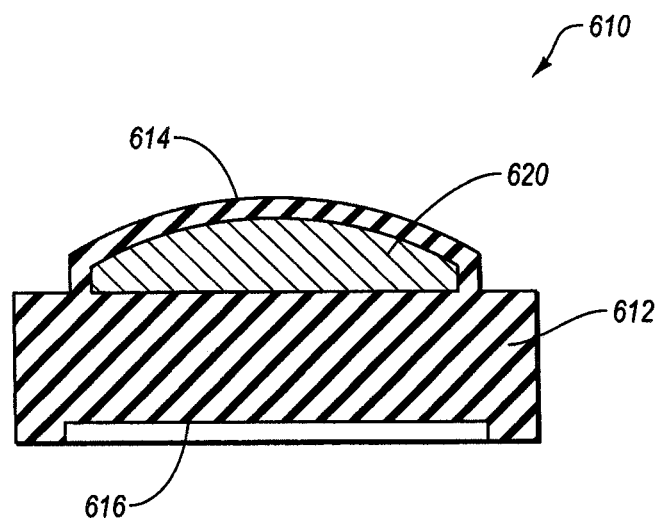
FIG. 54 shows a schematic, side cross-sectional view of one embodiment of a septum including at least one gel region.

For example, in one embodiment, a septum may include a gel that is at least substantially surrounded by a body material. For instance, FIG. 54 shows a schematic, side cross-sectional view of a septum 610 including a body 612 and a gel region 620 positioned within body 612. Gel region 620 may be structured so that a cannula inserted through upper surface 614 and extending through lower surface 616 will pass through a portion of gel region 620. In one embodiment, gel region 620 may comprise a silicone gel. In another embodiment, a gel region may comprise an initially an uncured liquid (i.e., has a relatively low viscosity) that may be cured to cause the liquid to form a gel. In a further embodiment, gel region 620 may comprise a viscous liquid, or a viscoelastic material.

In one example, gel region 620 may comprise an elastomer, such as, DOW CORNING® 7-9600 Soft Filling Elastomer, Parts A & B, which is commercially available from DOW CORNING Corporation of Midland, Mich. In another embodiment, gel region 620 may comprise Silicone Gel MED-6340, which is commercially available from NuSil Technology of Carpinteria, Calif. In yet a further embodiment, gel region 620 may comprise an elastomer exhibiting a Shore A hardness of about 20 to about 30, such as, for instance, DOW CORNING® C6-515 Liquid Silicone Rubber, Parts A & B or DOW CORNING® C6-530 Liquid Silicone Rubber Parts A & B, either of which is available from DOW CORNING Corporation of Midland, Mich. Further, optionally, body 612 of septum 610 may comprise a silicone material with a Shore A hardness of about 50 to about 60. In another embodiment, body 612 and/or upper surface 614 of septum 610 may comprise a silicone material with a Shore A hardness of about 60 to about 80. Optionally, body 612 and/or upper surface 614 of septum 610 may comprise a fluoropolymer (e.g., PTFE, etc.) or polyurethane.

One of ordinary skill in the art will understand that, upon removal of a cannula extending through at least a portion of gel region 620, a passageway or channel formed through gel region 620 may rebound, recover, seal, or heal. Further, gel region 620 may seal passageways formed through body 612 and upper surface 614. For example, gel region 620 may inhibit or prevent fluid leakage from a reservoir of an access port through the septum 610 when a pressure within the reservoir exceeds an ambient pressure external to the access port (e.g., during a power injection process, any process for flowing a fluid through an access port as described above, or any process for flowing a fluid through an access port as known in the art, without limitation). In addition, gel region 620 may be formulated and/or body 612 may be structured so that a cannula passing through septum 610 will resist transferring or removing any of the material comprising gel region 620 outside of a selected boundary or envelope. In one embodiment, body 612 may be structured to remove a material comprising gel region 620 from a cannula passing through the body 612.

Figure 55:
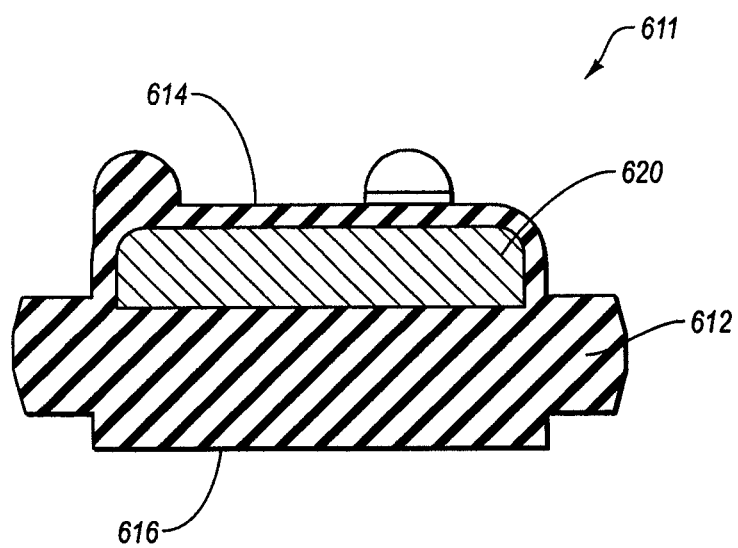
FIG. 55 shows a schematic, side cross-sectional view of another embodiment of a septum including at least one gel region.
Figure 56:
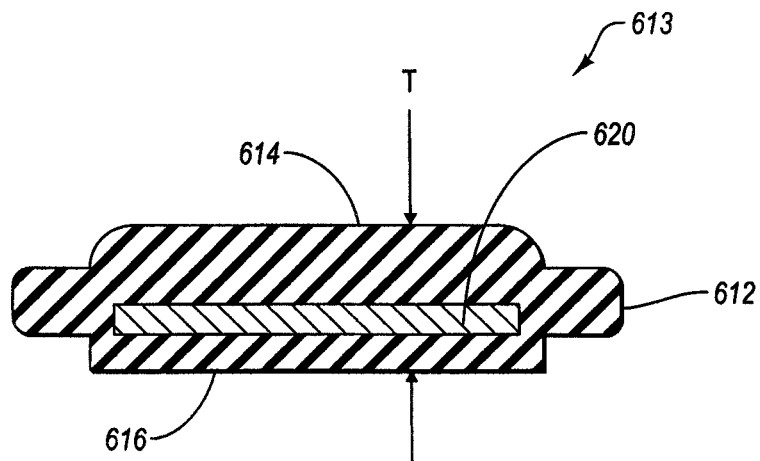
FIG. 56 shows a schematic, side cross-sectional view of a further embodiment of a septum including at least one gel region.

Any of the septum embodiments discussed herein may include at least one gel region. For example, FIG. 55 shows a schematic, side cross-sectional view of a septum 611 including a body 612 and a gel region 620. As discussed above, gel region 620 may be structured so that a cannula inserted through upper surface 614 and extending through lower surface 616 will pass through a portion of gel region 620. Such a configuration may provide a robust septum that resists leaking even if a multitude of passages are formed through the septum with a cannula. Furthermore, providing a septum comprising a gel may improve a sealing ability or quality of the septum. Accordingly, a septum including a gel material may exhibit a reduced thickness (i.e., from an upper surface to a lower surface) in comparison to a conventional septum. For example, FIG. 56 shows a septum 613 including a body 612 and a gel region 620, wherein a thickness T is less than a conventional thickness of a conventional septum. In one embodiment, a thickness T of septum 613 may be about 0.500 inches or less.

Figure 57:
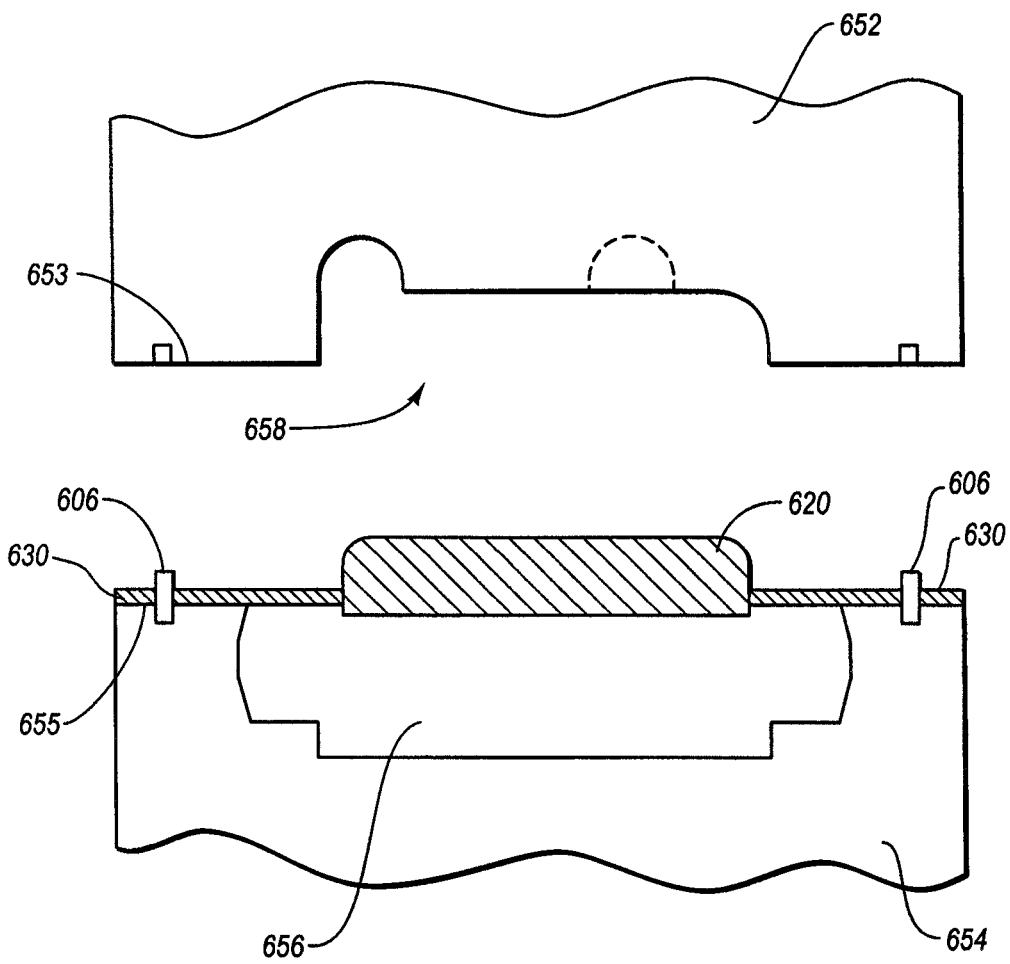
FIG. 57 shows a side cross-sectional view of a first mold and a second mold, wherein a gel region is positioned between the first mold and the second mold.

The instant disclosure contemplates a variety of different manufacturing methods may be employed for forming a septum comprising a gel. For example, generally, a body of a septum may be formed to substantially surround at least one gel region or a recess or chamber may be formed by a septum body that is filled with a gel. In one embodiment, a gel region may be suspended within a mold for forming a body of a septum. More particularly, FIG. 57 shows a schematic, side cross-sectional view of a first mold 652 and a second mold 654, wherein gel region 620 is positioned between (e.g., suspended) first mold 652 and second mold 654. As shown in FIG. 57, gel region 620 is positioned by a frame element 630, which abuts parting surface 655 of second mold 654. As shown in FIG. 57, frame element 630 may be positioned by pins 606. In other embodiments, frame element 630 may be suitably positioned, without limitation. In a particular embodiment, parting surface 653 of first mold 652 may be positioned proximate to parting surface 655 of second mold 654 (i.e., parting surfaces 653 and 655 may be separated by frame element 630) to form a chamber defined by cavity 658 and cavity 656. Further, a hardenable material (e.g., a curable material, such as a curable silicone, a thermoplastic, a resin, etc.) may be injected into the chamber and hardened. Thus, the hardenable material may surround or encapsulate gel region 620 and may exhibit a geometry that is complimentary to cavities 656 and 658.

Generally, frame element 630 may be coupled to or affixed to gel region 620. In one embodiment, frame element 630 may couple or engage at least a portion of a periphery of gel region 620. In another embodiment, frame element 630 may be substantially planar and gel region 620 may rest upon or may be formed upon frame element 630. Further, in one embodiment, frame element 630 may extend at least partially through gel region 620. Optionally, frame element 630 may cover or extend across mold cavity 656 of second mold 654. In one example, frame element 630 may comprise a mesh (e.g., a metal or polymer mesh, a fabric, a fiber mesh, etc.). In another example, frame element 630 may comprise a sheet or layer of silicone and may be, optionally, perforated. If frame element 630 comprises a mesh or is perforated, fluid communication (of a hardenable material) between cavity 658 and cavity 656 may occur, which may be desirable for avoiding shifting of gel region 620 and/or frame element 630 during encapsulation. Once gel region 620 is encapsulated, selected portions of frame element 630 may be trimmed or cut, if desired.

Figure 58:
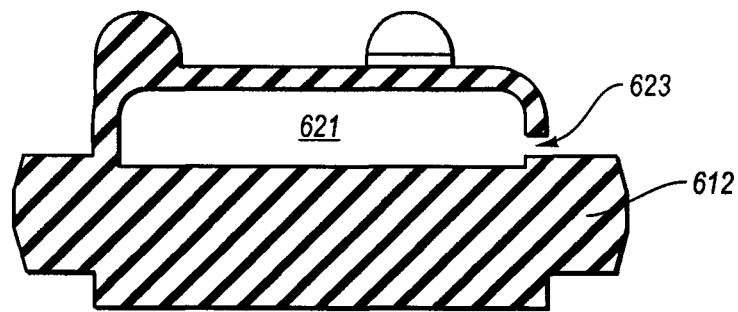
FIG. 58 shows a schematic, side cross-sectional view of an embodiment of a septum including at least one chamber to capture a gel.

In another method of forming a septum including at least one gel region, a septum body may be formed to include at least one chamber, which may be filled with a gel. For example, FIG. 58 shows a septum body 612 defining chamber 621. Optionally, opening 623 may be defined by body 612. Accordingly, a gel may be introduced within chamber 621 via the opening 623 and the opening, optionally, may be closed. For example, an uncured gel may be introduced within chamber 621. Further, the uncured gel may be cured by heating or by other suitable methods. Such a configuration may form a gel region as described above in relation to FIG. 55. In one embodiment, chamber 621 may be formed by an air injection molding process, a blow molding process or any other process known in the art for creating a chamber 621 within body 612. In another embodiment, body 612 may be formed about a removable plug or filler (e.g., a silicone plug, steel, or aluminum insert). Such a plug or filler may be coated with a nonstick coating (e.g., TEFLON®, silicone, or any nonstick coating known in the art). Thus, chamber 621 may be formed upon removal of the plug or filler. In other embodiments, portions of a septum may be formed, filled with a gel (or a liquid precursor to a gel), and bonded to one another to form a septum. In a further embodiment, body 612 may be initially formed and may enclose chamber 621 within body 612. In addition, body 612 may be cut to form an opening to allow chamber 621 to be filled with a gel. Such an opening of body 612 may be closed or sealed to capture or form a gel region. In yet a further embodiment, a solid body may be formed and a chamber may be formed by slicing the solid body. In such a configuration, filling the chamber may cause the solid body to deform to form a domed or raised region, if desired. It will be appreciated that many different approaches may be employed for forming a chamber 621 within body 612 and subsequently filling the chamber with a gel.

Figure 59:
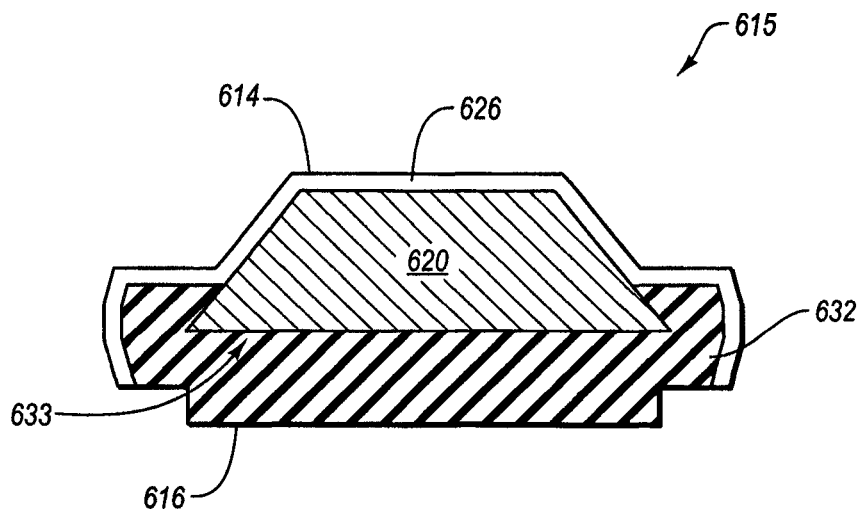
FIG. 59 shows a schematic, side cross-sectional view of an additional embodiment of a septum including at least one gel region.

In an additional embodiment, a septum may include a gel region positioned between a body and a layer of material bonded to or formed over at least a portion of the gel region and at least a portion of the body. For example, FIG. 59 shows a schematic, side cross-sectional view of a septum 615 including a body 632, a gel region 620, and a layer 626. As shown in FIG. 59, gel region 620 may be positioned within a recess 633 formed in the body 632 and layer 626 may extend over a portion of gel region 620 and a portion of body 632. One of ordinary skill in the art will understand that gel region 620 may be positioned or formed within recess 633 of body 632 and then layer 626 may be formed or positioned over gel region 620 and body 632. Further, layer 626 may be bonded (e.g., adhesively bonded, bonded via curing, bonded via welding, or as otherwise known in the art) or otherwise affixed to body 632 to capture gel region 620. In one embodiment, septum 615 may be formed by a multiple head (e.g., a two head) injection molding apparatus. More particularly, such a molding apparatus may be capable of forming the body 632, forming the gel region 620 within the body 632, and forming (e.g., over molding) the layer 626 over the gel region 620 and body 632 by suitable mold configurations and material injections. Layer 626, in one embodiment, may comprise a silicone-based material exhibiting a Shore A hardness of between about 60 and about 80. Body 632, in one embodiment, may comprise a silicone-based material exhibiting a Shore A hardness of between about 40 and about 50. Accordingly, during use of septum 615 (installed within a housing to form an access port) a cannula may pass through layer 626, at least a portion of gel region 620, and body 632. Such a configuration may facilitate positioning of a cannula extending through layer 626, at least a portion of gel region 620, and body 632.

While certain representative embodiments and details have been shown for purposes of illustrating aspects of the instant disclosure, it will be apparent to those skilled in the art that various changes in the methods and apparatus disclosed herein may be made without departing form the scope of the instant disclosure, which is defined in the appended claims. For example, other access port sizes and shapes may be employed; and various other embodiments and structures may be employed for forming at least one identifiable feature of an access port of the instant disclosure. The words "including" and "having," (including their variants) as used herein including the claims, shall have the same meaning as the word "comprising."

What is claimed is:

1. A method of using a power-injectable access port, comprising:
    obtaining the power-injectable access port,
        the power-injectable access port comprising:
            a housing;
            a septum;
            a reservoir; and
            an outlet stem in fluid communication with the reservoir,
        the power-injectable access port rated for injection of contrast media at a flow rate of at least 1 milliliter per second,
        the power-injectable access port structured for operation at a pressure in the reservoir of at least 35 psi;
    attaching a catheter to the outlet stem;
    implanting the power-injectable access port and the catheter into a patient;
    identifying the power-injectable access port following the implanting;
    inserting a distal end of a needle through the septum and into the reservoir; and
    injecting the contrast media through the needle at a rate of at least one milliliter per second.

2. The method according to claim 1, wherein the power-injectable access port further comprises a radiopaque feature, the identifying step including using X-ray to detect the radiopaque feature.

3. The method according to claim 2, wherein the radiopaque feature is provided by a radiopaque material in the septum.

4. The method according to claim 1, further comprising providing an identification feature separate from the power-injectable access port, the identifying step including visually perceiving the identification feature.

5. The method according to claim 4, wherein the injecting the contrast media includes using an infusion apparatus, and wherein the identification feature is provided on one or more components of the infusion apparatus.

6. The method according to claim 4, wherein the identification feature is provided on an element selected from the group consisting of a key chain, a bracelet, a wrist band, a sticker provided on a patient's chart, a patient ID card, a label provided on packaging of the power-injectable access port, and combinations thereof.

7. The method according to claim 1, wherein the step of injecting the contrast media through the needle includes inducing a pressure within the reservoir in a range of about 37 psi to about 65 psi.

8. The method according to claim 1, wherein the needle is constructed to have a burst pressure of at least 100 psi.

9. The method according to claim 8, wherein the needle is constructed to have a burst pressure of at least 400 psi.

10. The method according to claim 1, wherein the power-injectable access port is rated for injection of contrast media at a flow rate of between 2 milliliters per second and 5 milliliters per second.

11. The method according to claim 1, wherein the step of identifying the power-injectable access port is performed prior to, and as a precondition for, the step of injecting the contrast media through the needle.

12. The method according to claim 11, wherein the power-injectable access port further comprises a radiopaque feature, the identifying step including using X-ray to detect the radiopaque feature.

13. The method according to claim 12, wherein the radiopaque feature is provided by a radiopaque material in the septum.

14. The method according to claim 11, further comprising providing an identification feature separate from the power-injectable access port, the identifying step including visually perceiving the identification feature.

15. The method according to claim 14, wherein the step of injecting the contrast media includes using an infusion apparatus, and wherein the identification feature is provided on one or more components of the infusion apparatus.

16. The method according to claim 14, wherein the identification feature is provided on an element selected from the group consisting of a key chain, a bracelet, a wrist band, a sticker provided on a patient's chart, a patient ID card, a label provided on packaging of the power-injectable access port, and combinations thereof.

17. The method according to claim 11, wherein the step of injecting the contrast media through the needle includes inducing a pressure within the reservoir in a range of about 37 psi to about 65 psi.

18. The method according to claim 11, wherein the needle is constructed to have a burst pressure of at least 100 psi.

19. The method according to claim 18, wherein the needle is constructed to have a burst pressure of at least 400 psi.

20. The method according to claim 11, wherein the power-injectable access port is rated for injection of contrast media at a flow rate of between 2 milliliters per second and 5 milliliters per second.

21. The method according to claim 1, wherein as a result of the implanting step, an implanted power-injectable access port is inside of the patient, wherein the step of identifying the power-injectable access port following the implanting step comprises confirming that the implanted port is the power-injectable access port, and wherein the injecting step is performed subsequent to the confirming step.

22. The method according to claim 21, wherein the power-injectable access port further comprises a radiopaque feature, the identifying step including using X-ray to detect the radiopaque feature.

23. The method according to claim 22, wherein the radiopaque feature is provided by a radiopaque material in the septum.

24. The method according to claim 21, further comprising providing an identification feature separate from the power-injectable access port, the identifying step including visually perceiving the identification feature.

25. The method according to claim 24, wherein the step of injecting the contrast media includes using an infusion apparatus, and wherein the identification feature is provided on one or more components of the infusion apparatus.

26. The method according to claim 24, wherein the identification feature is provided on an element selected from the group consisting of a key chain, a bracelet, a wrist band, a sticker provided on a patient's chart, a patient ID card, a label provided on packaging of the power-injectable access port, and combinations thereof.

27. The method according to claim 21, wherein the step of injecting the contrast media through the needle includes inducing a pressure within the reservoir in a range of about 37 psi to about 65 psi.

28. The method according to claim 21, wherein the needle is constructed to have a burst pressure of at least 100 psi.

29. The method according to claim 28, wherein the needle is constructed to have a burst pressure of at least 400 psi.

30. The method according to claim 21, wherein the power-injectable access port is rated for injection of contrast media at a flow rate of between 2 milliliters per second and 5 milliliters per second.

31. The method according to claim 1, wherein based on the step of identifying the power-injectable access port following the implanting step, the injecting step is performed.

32. The method according to claim 31, wherein the power-injectable access port further comprises a radiopaque feature, the identifying step including using X-ray to detect the radiopaque feature.

33. The method according to claim 32, wherein the radiopaque feature is provided by a radiopaque material in the septum.

34. The method according to claim 31, further comprising providing an identification feature separate from the power-injectable access port, the identifying step including visually perceiving the identification feature.

35. The method according to claim 34, wherein the step of injecting the contrast media includes using an infusion apparatus, and wherein the identification feature is provided on one or more components of the infusion apparatus.

36. The method according to claim 34, wherein the identification feature is provided on an element selected from the group consisting of a key chain, a bracelet, a wrist band, a sticker provided on a patient's chart, a patient ID card, a label provided on packaging of the power-injectable access port, and combinations thereof.

37. The method according to claim 31, wherein the step of injecting the contrast media through the needle includes inducing a pressure within the reservoir in a range of about 37 psi to about 65 psi.

38. The method according to claim 31, wherein the needle is constructed to have a burst pressure of at least 100 psi.

39. The method according to claim 38, wherein the needle is constructed to have a burst pressure of at least 400 psi.

40. The method according to claim 31, wherein the power-injectable access port is rated for injection of contrast media at a flow rate of between 2 milliliters per second and 5 milliliters per second.

* * * * *